(12) United States Patent
Ohashi et al.

(10) Patent No.: US 8,394,570 B2
(45) Date of Patent: *Mar. 12, 2013

(54) SULFONIUM SALT, ACID GENERATOR, RESIST COMPOSITION, PHOTOMASK BLANK, AND PATTERNING PROCESS

(75) Inventors: Masaki Ohashi, Joetsu (JP); Takeshi Kinsho, Joetsu (JP); Satoshi Watanabe, Joetsu (JP); Youichi Ohsawa, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 433 days.

This patent is subject to a terminal disclaimer.

(21) Appl. No.: 12/630,559

(22) Filed: Dec. 3, 2009

(65) Prior Publication Data

US 2010/0143830 A1    Jun. 10, 2010

(30) Foreign Application Priority Data

Dec. 4, 2008 (JP) ................. 2008-309566

(51) Int. Cl.
  *G03F 1/00* (2006.01)
  *G03F 7/00* (2006.01)
  *C07C 309/00* (2006.01)
(52) U.S. Cl. .......... 430/270.1; 430/322; 430/325; 430/913; 430/914; 558/44
(58) Field of Classification Search .......... 522/1–189; 430/5, 296, 322, 325, 270.1, 913, 914; 552/526
See application file for complete search history.

(56) References Cited

U.S. PATENT DOCUMENTS

| 5,238,781 A | 8/1993 | Schadell |
| 5,635,332 A | 6/1997 | Nakano et al. |
| 5,650,483 A | 7/1997 | Malik et al. |

(Continued)

FOREIGN PATENT DOCUMENTS

| EP | 0 473 547 A1 | 3/1992 |
| EP | 1199603 A1 * | 4/2002 |

(Continued)

OTHER PUBLICATIONS

Anderson, K. K. et al "The Chemistry of the sulphonium group Part 1" John Wiley and Sons, 1981, pp. 267-312.
Arimitsu, Koji "Sensitivity Enhancement of Chemical-Amplification-Type Photoimaging Materials by Acetoacetic Acid Derivatives", Journal of Photopolymer Science and Technology, vol. 8, No. 1, 1995, pp. 43-44.
Arimitsu, Koji et al. "Effect of Phenolic Hydroxyl Residues on the Improvement of Acid-Proliferation-Type Photoimaging Materials", Journal of Photopolymer Science and Technology, vol. 9, No. 1, 1996, pp. 29-30.

(Continued)

*Primary Examiner* — Cynthia Kelly
*Assistant Examiner* — Connie P Johnson
(74) *Attorney, Agent, or Firm* — Birch, Stewart, Kolasch & Birch, LLP

(57) ABSTRACT

A sulfonium salt has formula (1) wherein $R^1$ is a monovalent hydrocarbon group except vinyl and isopropenyl, $R^2$, $R^3$, and $R^4$ are alkyl, alkenyl, oxoalkyl, aryl, aralkyl or aryloxoalkyl or may bond together to form a ring with the sulfur atom, and n is 1 to 3. A chemically amplified resist composition comprising the sulfonium salt is capable of forming a fine feature pattern of good profile after development due to high resolution, improved focal latitude, and minimized line width variation and profile degradation upon prolonged PED.

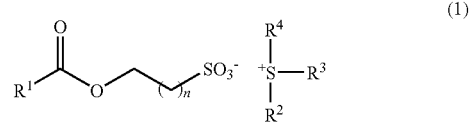

(1)

12 Claims, 7 Drawing Sheets

U.S. PATENT DOCUMENTS

| | | | |
|---|---|---|---|
| 5,705,702 | A | 1/1998 | Osawa et al. |
| 5,731,364 | A | 3/1998 | Sinta et al. |
| 5,880,169 | A | 3/1999 | Osawa et al. |
| 5,945,250 | A | 8/1999 | Aoai et al. |
| 6,306,555 | B1 | 10/2001 | Schulz et al. |
| 6,312,867 | B1 | 11/2001 | Kinsho et al. |
| 6,440,634 | B1 | 8/2002 | Ohsawa et al. |
| 6,448,430 | B1 | 9/2002 | Hembre |
| 6,723,483 | B1 | 4/2004 | Oono et al. |
| 6,830,866 | B2 | 12/2004 | Kobayashi et al. |
| 7,537,880 | B2 | 5/2009 | Harada et al. |
| 7,569,326 | B2 | 8/2009 | Ohsawa et al. |
| 2002/0102491 | A1* | 8/2002 | Kodama et al. ............ 430/270.1 |
| 2004/0033440 | A1 | 2/2004 | Maeda et al. |
| 2004/0260031 | A1 | 12/2004 | Takeda et al. |
| 2007/0212619 | A1* | 9/2007 | Yoshikawa et al. ............... 430/5 |
| 2007/0231738 | A1 | 10/2007 | Kaneko et al. |
| 2008/0026331 | A1 | 1/2008 | Hasegawa et al. |
| 2008/0318160 | A1 | 12/2008 | Ohsawa et al. |

FOREIGN PATENT DOCUMENTS

| | | | |
|---|---|---|---|
| JP | 4-230645 | A | 8/1992 |
| JP | 5-222257 | A | 8/1993 |
| JP | 7-25846 | A | 12/1995 |
| JP | 8-311018 | A | 2/1996 |
| JP | 9-15848 | A | 1/1997 |
| JP | 9-323970 | A | 12/1997 |
| JP | 10-39500 | A | 2/1998 |
| JP | 2000-336121 | A | 12/2000 |
| JP | 2001-106651 | A | 4/2001 |
| JP | 2001-122850 | A | 5/2001 |
| JP | 2001-181221 | A | 7/2001 |
| JP | 2002-193887 | A | 7/2002 |
| JP | 2002-193925 | A | 7/2002 |
| JP | 2003-66612 | A | 3/2003 |
| JP | 2004-115630 | A | 4/2004 |
| JP | 2004-133393 | A | 4/2004 |
| JP | 3613491 | B2 | 11/2004 |
| JP | 2005-8766 | A | 1/2005 |
| JP | 2005-84365 | A | 3/2005 |
| JP | 2006-58842 | A | 3/2006 |
| JP | 2007-145797 | A | 6/2007 |
| JP | 2007-297590 | A | 11/2007 |
| JP | 2007-304528 | A | 11/2007 |
| JP | 2008-31298 | A | 2/2008 |
| JP | 2008-111103 | A | 5/2008 |
| JP | 2008-133448 | A | 6/2008 |

OTHER PUBLICATIONS

Dammel, R. Ralph et al "193 nm Immersion Lithography—Taking the Plunge", Journal of Photopolymer Science and Technology, vol. 17, No. 4, 2004, pp. 587-601.

Devoe, Robert J. et al. "Photochemistry and Photophysics of 'Onium Salts", Advances in Photochemistry, vol. 17, John Wiley and Sons 1992. pp. 313-321.

Kudo, Kazuaki et al. "Enhancement of the Sensitivity of Chemical-Amplification-Type Photoimaging Materials by β-Tosyloxyketone Acetals", Journal of Photopolymer Science and Technology vol. 8, No. 1, 1995, pp. 45-46.

Miller, R. D. et al, "Deoxygenation of Sulfoxides Promoted by Electrophilic Silicon Reagents; Preparation of Aryl-Substituted Sulfonium Salts", Journal of Organic Chemistry., vol. 53, No. 23, 1988, pp. 5571-5573.

* cited by examiner

SULFONIUM SALT, ACID GENERATOR, RESIST COMPOSITION, PHOTOMASK BLANK, AND PATTERNING PROCESS

CROSS-REFERENCE TO RELATED APPLICATION

This non-provisional application claims priority under 35 U.S.C. §119(a) on Patent Application No. 2008-309566 filed in Japan on Dec. 4, 2008, the entire contents of which are hereby incorporated by reference.

TECHNICAL FIELD

This invention generally relates to chemically amplified resist compositions which are sensitive to such radiation as ultraviolet (UV), deep UV, electron beam, x-ray, excimer laser, gamma-ray and synchrotron radiation and suitable for the microfabrication of integrated circuits. More particularly, it relates to a sulfonium salt and an acid generator, especially photoacid generator, for use in such resist compositions. It also relates to a chemically amplified resist composition comprising the acid generator, a photomask blank using the same, and a pattern forming process using the same.

BACKGROUND ART

While a number of efforts are currently being made to achieve a finer pattern rule in the drive for higher integration and operating speeds in LSI devices, deep UV lithography is thought to hold particular promise as the next generation in microfabrication technology.

One technology that has recently attracted a great deal of attention utilizes as the deep UV light source a high-intensity KrF excimer laser and an ArF excimer laser featuring a shorter wavelength. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004). There is a desire to have a microfabrication technique of finer definition by combining exposure light of shorter wavelength with a resist material having a higher resolution.

In this regard, the recently developed, acid-catalyzed, chemically amplified resist materials are expected to comply with the deep UV lithography because of their many advantages including high sensitivity, resolution and dry etching resistance. The chemically amplified resist materials include positive working materials that leave the unexposed areas with the exposed areas removed and negative working materials that leave the exposed areas with the unexposed areas removed.

In chemically amplified, positive working, resist compositions to be developed with alkaline developers, a resin and/or compound in which alkali-soluble phenol or carboxylic acid is partially or entirely protected with acid-labile protective groups (acid labile groups) is catalytically decomposed by an acid which is generated upon exposure, to thereby generate the phenol or carboxylic acid in the exposed area which is removed by an alkaline developer. Also, in similar negative working resist compositions, a resin and/or compound having alkali-soluble phenol or carboxylic acid and a compound (acid crosslinking agent) capable of bonding or crosslinking the resin or compound under the action of an acid are crosslinked with an acid which is generated upon exposure whereby the exposed area is converted to be insoluble in an alkaline developer and the unexposed area is removed by the alkaline developer.

On use of the chemically amplified positive resist compositions, a resist film is formed by dissolving a resin having acid labile groups as a binder and a compound capable of generating an acid upon exposure to radiation (to be referred to as photoacid generator or PAG) in a solvent, applying the resist solution onto a substrate by a variety of methods, and evaporating off the solvent optionally by heating. The resist film is then exposed to radiation, for example, deep UV through a mask having a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

The chemically amplified positive resist compositions adapted for KrF excimer laser generally use phenolic resins, for example, polyhydroxystyrene in which some or all of the hydrogen atoms of phenolic hydroxyl groups are protected with acid labile protective groups. Typical PAGs used therein are iodonium salts, sulfonium salts, bissulfonyldiazomethane compounds, N-sulfonyloxydicarboxylmide compounds, and O-arenesulfonyloxime compounds. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

PAGs capable of generating 10-camphorsulfonic acid and 2,4,6-triisopropylbenzenesulfonic acid, whether they are sulfonium and iodonium salts or O-arenesulfonyloxime compounds, are low diffusible and very useful in providing high resolution resist materials. See JP-A 5-222257, JP-A 9-323970, JP-A 10-39500, and JP-A 2004-133393.

As the requisite pattern size is reduced, however, even the use of these PAGs encounters problems including low resolution and low stability to the environment. Improvements in resolution may be made by incorporating an acid labile group which is more scissile to acid in the base resin, by using a basic additive, or by controlling processing conditions.

The environmental stability is generally divided into two categories. One stability problem is that the acid generated upon exposure is deactivated with airborne bases on the resist film or bases on the substrate beneath the resist film. This phenomenon is often found when a photoacid generator capable of generating an acid having a high acid strength is used. This problem is addressed by rendering the acid labile groups in the resin more scissile to acid or by reducing (or weakening) the acid strength of the acid generated. The other problem of environmental stability is that when the duration between exposure and post-exposure bake (PEB) is prolonged, that is, in the case of post-exposure delay (PED), the acid generated diffuses through the resist film so that acid deactivation occurs if acid labile groups are less scissile or acid decomposition reaction occurs if acid labile groups are more scissile, often leading to variations of the pattern profile. In chemically amplified positive resist compositions having acid labile groups including primarily acetal groups, for example, the line width of unexposed areas is often narrowed.

JP 3613491 discloses an anion-bound PAG polymer having PAG combined with a non-acid-labile group-containing monomer. Since the effect of PAG is weakened by the non-acid-labile group-containing monomer, the composition is unsatisfactory in resolution or the like.

As discussed above, in order to gain a higher resolution, an acid labile group which is more scissile must be incorporated in the base resin and the PAG is desired to generate a low diffusible acid. JP-A 2006-58842 and JP-A 2007-304528 describe as the agent for deactivating fluorinated alkanesulfonic acid generated by a PAG upon exposure, a sulfonium salt capable of generating 1-adamantanesulfonic acid having lower acid strength than the fluorinated alkanesulfonic acid. In these patents, the sulfonium salt is used as adjuvant rather than the PAG.

The electron beam (EB) lithography is not only of interest as the micropatterning technology capable of processing to a feature size of 0.1 μm or less, but also becomes indispensable to form mask patterns. However, EB imagewise drawing takes a longer time than the conventional block exposure process. To increase the throughput, resists are thus required to have a higher sensitivity. The stability with time of resist in vacuum during and after imagewise drawing is also one of crucial performance factors. Some coatings on substrates, for example, coatings of $SiO_2$, TiN or $Si_3N_4$ on silicon wafers and chromium oxide on mask blanks can affect the resist profile after development (e.g., forming a footing profile) depending on the particular type of substrate. For achieving high resolution and maintaining a profile after etching, it is one of important performance factors that the pattern profile of resist is kept rectangular independent of the substrate type.

CITATION LIST

Patent Document 1: JP-A H05-222257
Patent Document 2: JP-A H10-39500
Patent Document 3: JP-A 2004-133393
Patent Document 4: JP-A H09-323970
Patent Document 5: JP 3613491
Patent Document 6: JP-A 2006-58842
Patent Document 7: JP-A 2007-304528
Non-Patent Document 1: Journal of Photopolymer Science and Technology, Vol. 17, No. 4, p 587 (2004)

SUMMARY OF INVENTION

The acid generator for use in resist materials must meet the requirements including a high solubility in or compatibility with the resist solvent and resin, storage stability enough to form a pattern of satisfactory profile, PED stability, high sensitivity and resolution, and wider depth of focus. None of prior art PAGs meet all the requirements. In processing of a photomask blank, degradation of pattern profile on the mask blank is regarded serious because such degradation can cause pattern collapse under the current technical trend toward further miniaturization of the integrated circuit pattern.

An object of the present invention is to provide a novel sulfonium salt and acid generator for use in chemically amplified resist material, a chemically amplified resist composition comprising the same which has solved the aforementioned problems and is improved in pattern profile, a photomask blank and a patterning process using the composition.

The inventors have found that a sulfonium salt having the general formula (1), shown below, can be readily prepared, and that a resist composition comprising the salt is improved in many properties including PED stability, pattern profile, resolution, and sensitivity and very useful in precise micropatterning.

Accordingly the invention provides a sulfonium salt, acid generator, resist composition, photomask blank, and pattern forming process as defined below.

In a first aspect, the invention provides a sulfonium salt having the general formula (1).

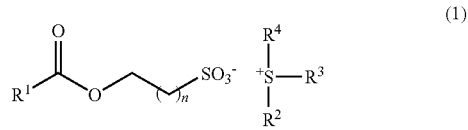

(1)

Herein $R^1$ is a straight, branched or cyclic monovalent hydrocarbon group of 1 to 50 carbon atoms which may contain a heteroatom, except vinyl and isopropenyl, $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$, and $R^4$ may bond together to form a ring with the sulfur atom, and n is an integer of 1 to 3.

The preferred sulfonium salt has the general formula (2).

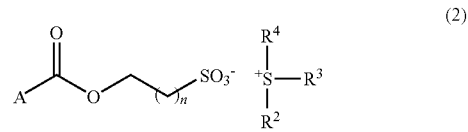

(2)

Herein A is a monovalent hydrocarbon group having an aromatic ring or alicyclic hydrocarbon structure of at least 5 carbon atoms, $R^2$, $R^3$, $R^4$ and n are as defined above.

Also provided is an acid generator comprising the sulfonium salt defined above.

In a second aspect, the invention provides a chemically amplified resist composition comprising an acid generator capable of generating a sulfonic acid having the general formula (1a) in response to high-energy radiation or heat.

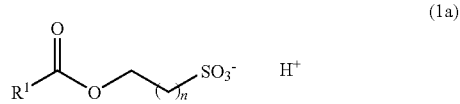

(1a)

Herein $R^1$ is a straight, branched or cyclic monovalent hydrocarbon group of 1 to 50 carbon atoms which may contain a heteroatom, except vinyl and isopropenyl, and n is an integer of 1 to 3.

The preferred sulfonic acid has the general formula (2a).

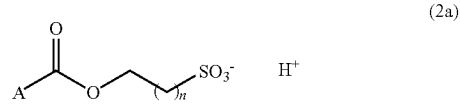

(2a)

Herein A is a monovalent hydrocarbon group having an aromatic ring or alicyclic hydrocarbon structure of at least 5 carbon atoms, and n is an integer of 1 to 3.

Also provided is a chemically amplified resist composition comprising the sulfonium salt of formula (1), preferably formula (2).

The chemically amplified resist composition is subject to patternwise exposure to high-energy radiation selected from KrF laser radiation, ArF laser radiation, EUV and electron beam.

In a third aspect, the invention provides a process for forming a pattern on a processable substrate using the chemically amplified resist composition defined above.

In a fourth aspect, the invention provides a photomask blank comprising a chromium compound film and the chemically amplified resist composition defined above applied thereon.

In a fifth aspect, the invention provides a pattern forming process comprising the steps of heat treating the photomask blank, subjecting the photomask blank to patternwise exposure to high-energy radiation through a photomask or patternwise exposure to high-energy beam, optionally heat treating, and developing the exposed photomask blank with a developer.

ADVANTAGEOUS EFFECTS OF INVENTION

A chemically amplified resist composition comprising a specific PAG capable of generating an acid upon exposure to high-energy radiation is improved in focal latitude, minimized in line width variation and pattern profile degradation even on prolonged PED, improved in pattern profile after development, and high in resolution enough for precise micropatterning. When the PAG is combined with a resin having an acid labile group which is more scissile to acid, like the acetal type, the composition is endowed with an increased dissolution contrast between exposed and unexposed areas and an enhanced resolution capability. The composition is effective particularly when processed by the deep UV and EB lithography.

DESCRIPTION OF EMBODIMENTS

Figure 1:
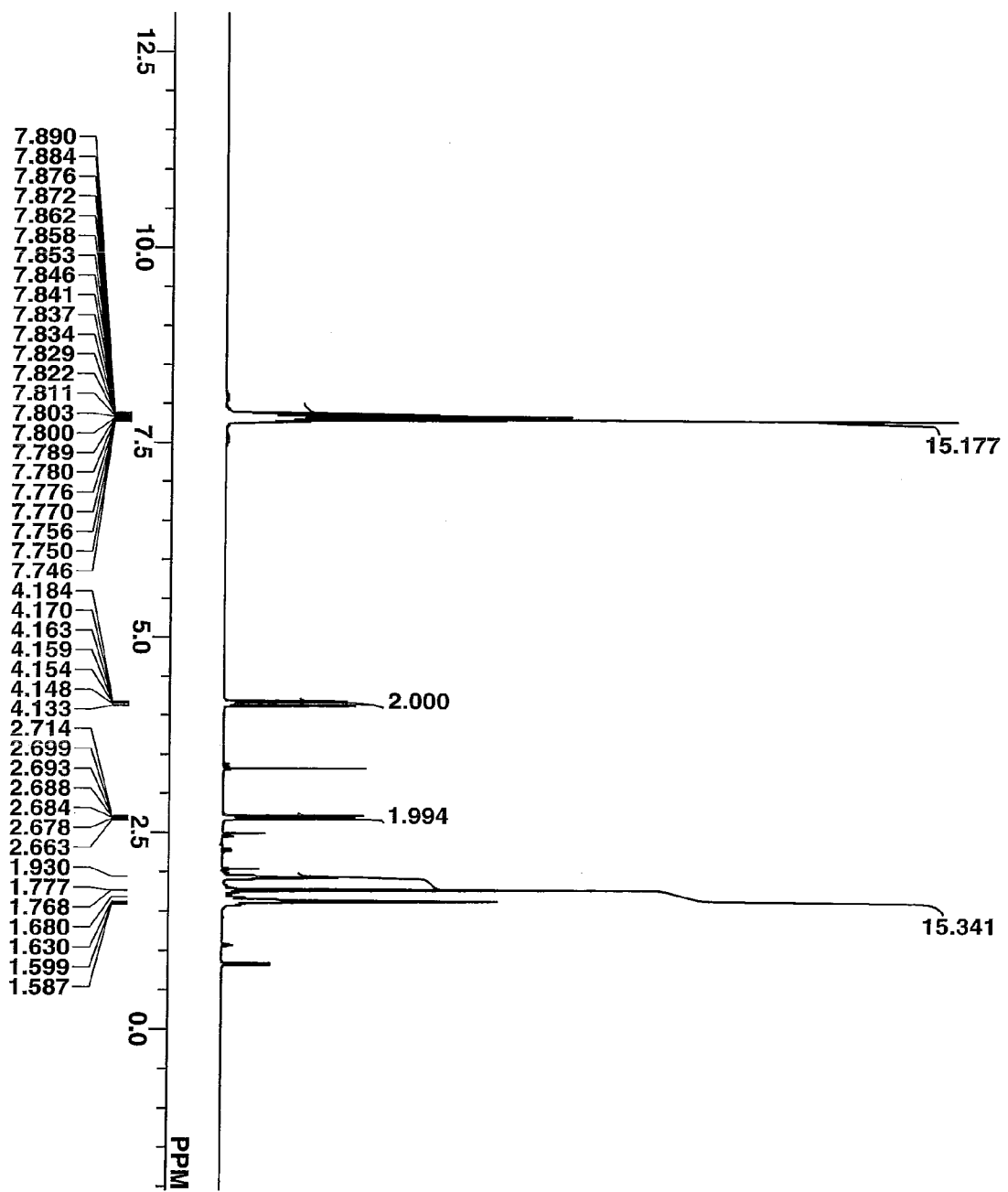
FIG. 1 is a diagram showing the $^1$H-NMR spectrum of PAG-1 in Synthesis Example 1-9.

The singular forms "a", "an" and "the" include plural references unless the context clearly dictates otherwise.

The notation (Cn-Cm) means a group containing from n to m carbon atoms per group.

Sulfonium Salt

In the first aspect, the invention provides a sulfonium salt having the general formula (1) and a photoacid generator (PAG) comprising the sulfonium salt.

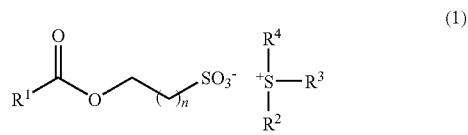

Herein $R^1$ is a straight, branched or cyclic monovalent hydrocarbon group of 1 to 50 carbon atoms which may contain a heteroatom, except vinyl and isopropenyl. $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or any two or more of $R^2$, $R^3$, and $R^4$ may bond together to form a ring with the sulfur atom. The subscript n is an integer of 1 to 3.

In formula (1), $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group. Alternatively, any two or more of $R^2$, $R^3$, and $R^4$ may bond together to form a ring with the sulfur atom in the formula. Specifically, suitable alkyl groups include, but are not limited to, methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include, but are not limited to, vinyl, allyl, propenyl, butenyl, hexenyl, and cyclohexenyl. Suitable oxoalkyl groups include, but are not limited to, 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include, but are not limited to, phenyl, naphthyl and thienyl; 4-hydroxylphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include, but are not limited to, benzyl, 1-phenylethyl, and 2-phenylethyl. Suitable aryloxoalkyl groups include, but are not limited to, 2-aryl-2-oxoethyl groups such as 2-phenyl-2-oxoethyl, 2-(1-naphthyl)-2-oxoethyl, and 2-(2-naphthyl)-2-oxoethyl. When any two or more of $R^2$, $R^3$ and $R^4$ bond together to form a cyclic structure with the sulfur atom, exemplary cyclic structures are shown below.

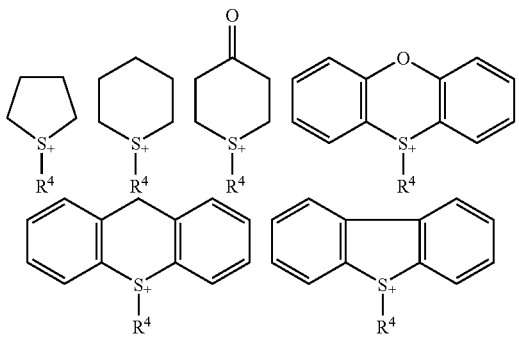

Herein $R^4$ is as defined above.

Illustrative examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, tris(4-tert-butoxyphenyl)sulfonium, and dimethylphenylsulfonium.

In formula (1), $R^1$ is a straight, branched or cyclic monovalent hydrocarbon group of 1 to 50 carbon atoms which may contain a heteroatom. It is excluded that $R^1$ is vinyl and isopropenyl. As the monovalent hydrocarbon group, suitable alkyl groups include, but are not limited to, methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, adamantyl, and steroid structure-containing groups. Suitable oxoalkyl groups include, but are not limited to, 2-oxocyclopentyl, 2-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl, and 4-oxa-tricyclo[4.2.1.0$^{3,7}$]nonan-5-on-9-yl. Suitable aryl groups include, but are not limited to, phenyl, naphthyl, anthranyl, and thienyl; 4-hydroxylphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include, but are not limited to, benzyl, 1-phenylethyl, and 2-phenylethyl. Suitable aryloxoalkyl groups include, but are not limited to, 2-aryl-2-oxoethyl groups such as 2-phenyl-2-oxoethyl, 2-(1-naphthyl)-2-oxoethyl, and 2-(2-naphthyl)-2-oxoethyl.

Of the structures having formula (1), those structures having formula (2) are preferred.

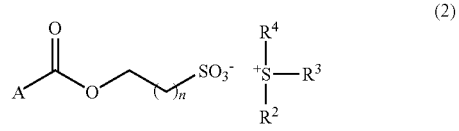

Herein A is a monovalent hydrocarbon group having an aromatic ring or alicyclic hydrocarbon structure of at least 5 carbon atoms, $R^2$, $R^3$, $R^4$ and n are as defined above.

In formula (2), A is a monovalent hydrocarbon group having an aromatic ring or alicyclic hydrocarbon structure of at least 5 carbon atoms. By endowing A with a bulky structure and selecting n in the range of 1 to 3, that is, by interposing an ethylene, propylene or butylene group between the bulky acyl group and the sulfo group, the PAG is given an adequate degree of mobility despite the bulky structure. Therefore, the PAG has an adequate acid diffusion ability. As a result, a resist composition comprising the PAG is believed to be improved in focal latitude, pattern profile after development, and resolution so that the composition is suited for micropatterning. Compounds wherein n=0 have short mobility and fail to provide the desired performance. Compounds wherein n is more than 3 are unacceptable because of limited availability of starting reactants and difficulty of synthesis. The synthesis process will be described later.

Illustrative examples of A include, but are not limited to, cyclopentyl, cyclohexyl, cycloheptyl, 4-methylcyclohexyl, cyclohexylmethyl, norbornyl, adamantyl, steroid structure-containing groups, 2-oxocyclopentyl, 2-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl, 4-oxa-tricyclo[4.2.1.0$^{3,7}$]nonan-5-on-9-yl, phenyl, naphthyl, anthranyl, thienyl, 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, methylnaphthyl, ethylnaphthyl, methoxynaphthyl, ethoxynaphthyl, dimethylnaphthyl, diethylnaphthyl, dimethoxynaphthyl, diethoxynaphthyl, benzyl, 1-phenylethyl, 2-phenylethyl, and 2-aryl-2-oxoethyl groups such as 2-phenyl-2-oxoethyl, 2-(1-naphthyl)-2-oxoethyl, and 2-(2-naphthyl)-2-oxoethyl.

In an embodiment wherein A has a cycloalkyl group, resolution and exposure latitude are improved due to controlled acid diffusion as compared with the case wherein A is chain-like. Most preferably A is adamantyl because its robust structure having an appropriate molecular size provides the relevant compound with an adequate acid diffusion control ability. Thus a resist composition comprising the same exhibits a high dissolution contrast after development and a good pattern profile.

In an embodiment wherein A has an aromatic ring such as benzene or naphthalene ring, acid diffusion can be controlled due to the bulky structure like alicyclic hydrocarbons, and transmittance and acid generation efficiency be adjusted due to its light absorption. In an aromatic ring-based polymer matrix such as polyhydroxystyrene, adapted for the KrF or EB lithography, the compound wherein A has an aromatic ring is uniformly dispersible because of its affinity to the polymer. The uniform dispersion of acid ensures that a pattern of rectangular profile is formed after development. In particular, naphthalene ring has no absorption to the ArF excimer laser, and the compound wherein A has a naphthalene ring may be advantageously used as bulky PAG not only in KrF, EUV and EB lithography, but also in ArF lithography.

In an exemplary resist composition comprising a base polymer having acid labile groups wherein the acid labile groups are present in a higher proportion or have a structure capable of facilitating acid diffusion (for example, the protective group is non-alicyclic or non-robust structure), the use of PAG wherein A has a steroid structure leads to a high dissolution contrast. This is attributable to the high acid diffusion controlling ability due to the steroid structure having a very large molecular size. In particular, dehydrocholic acid derivatives are preferred because of availability of starting reactants and ease of purification.

Where A has a carbonyl or hydroxyl group, or a polar group like carboxylic acid, the compound exhibits an excellent exposure latitude and depth of focus. This compound has affinity to polar units contained richly in the base resin in the resist composition, so that the compound or PAG may be uniformly dispersed in the polymer matrix. Particularly when A has a norbornane lactone structure, the compound exhibits a very high diffusion controlling ability and uniform dispersion due to both the advantages of a robust structure and a polar group, leading to a good pattern profile.

Exemplary structures of the anion moiety in formula (2) are shown below, but not limited thereto.

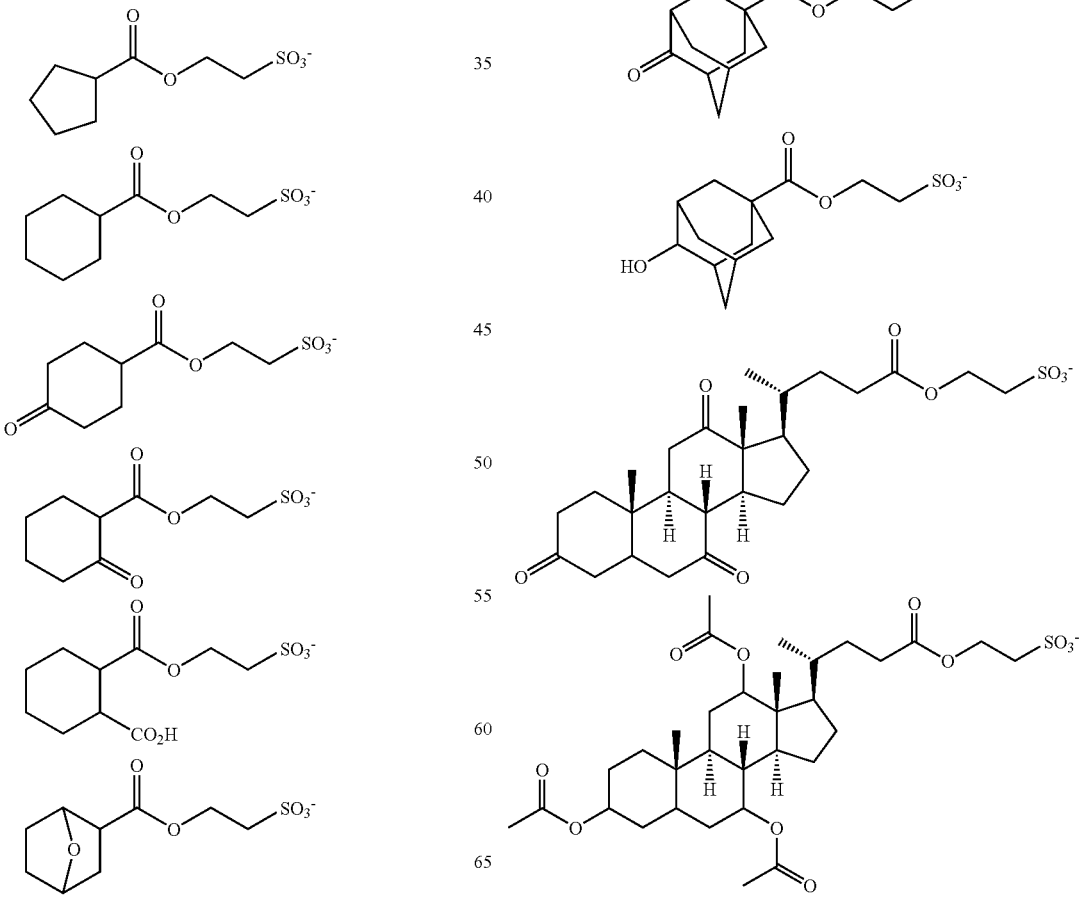

11
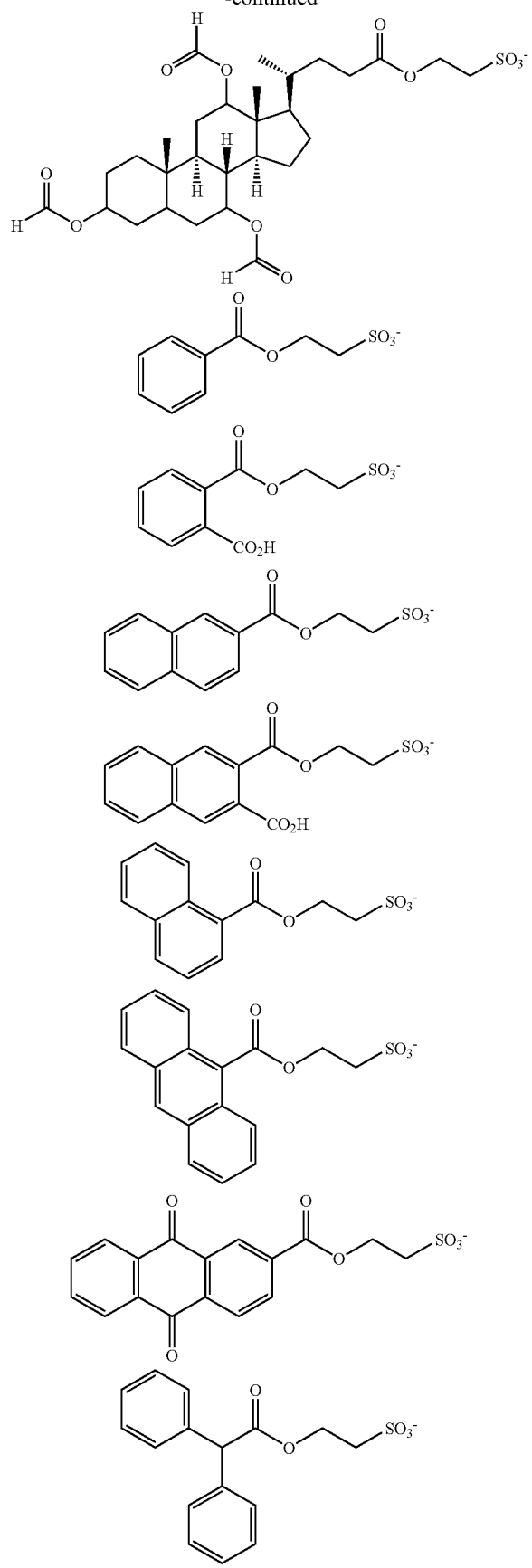
12
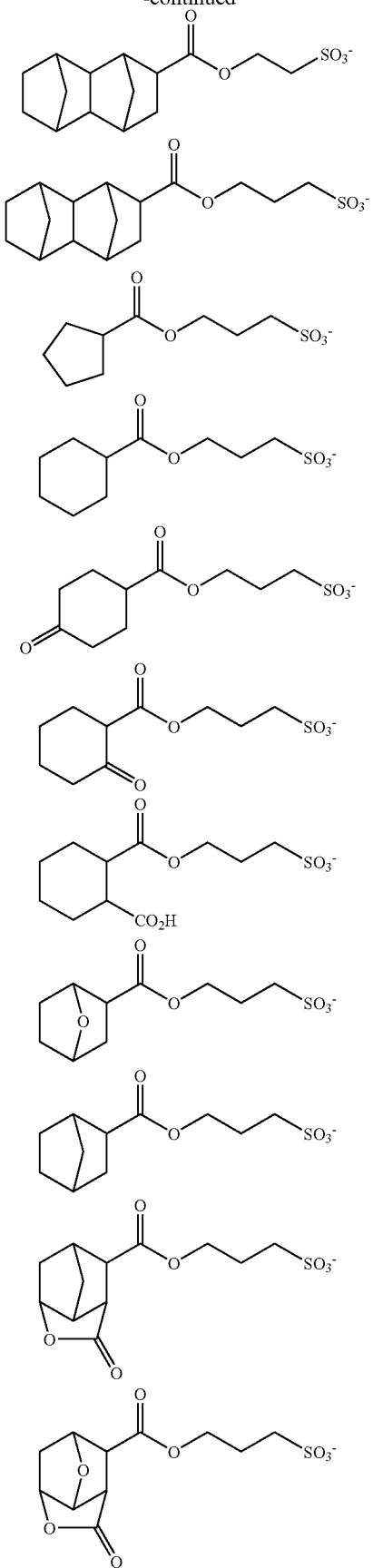

-continued
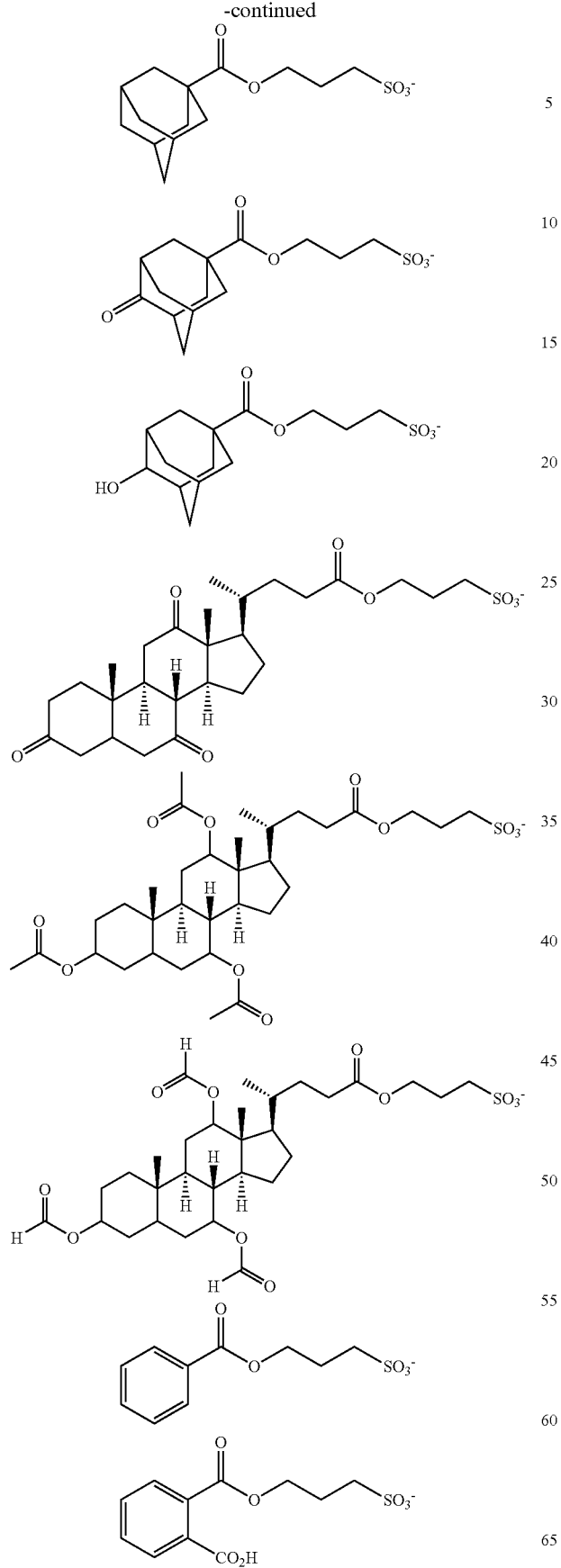
-continued
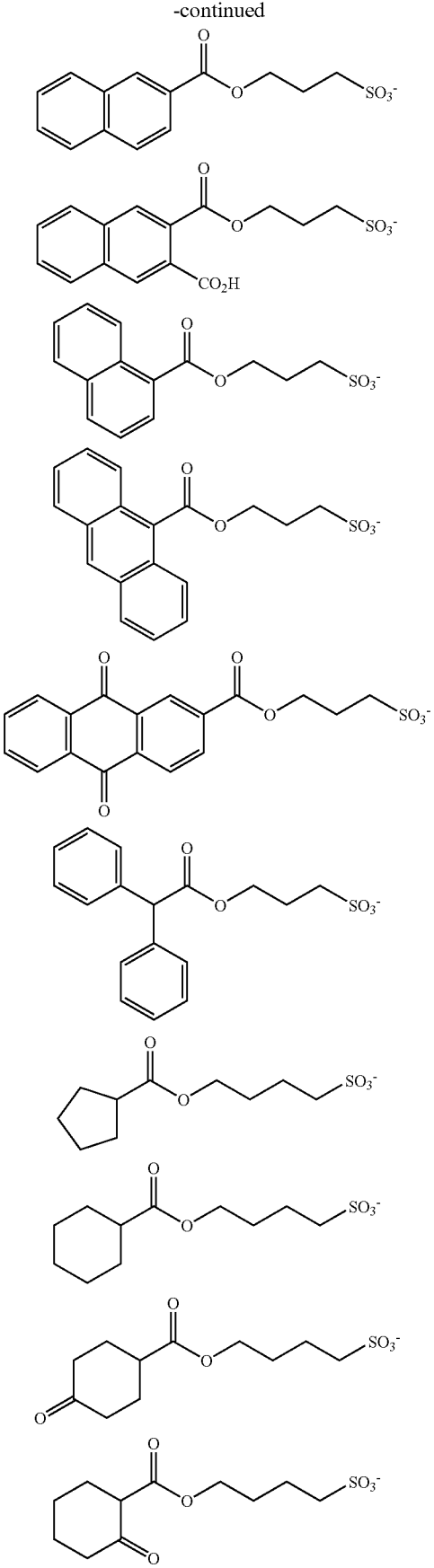

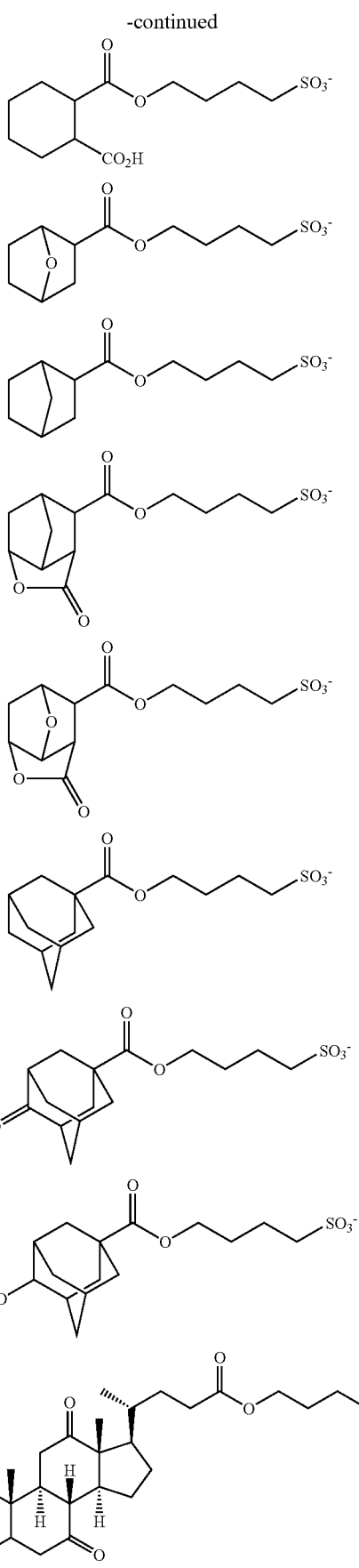
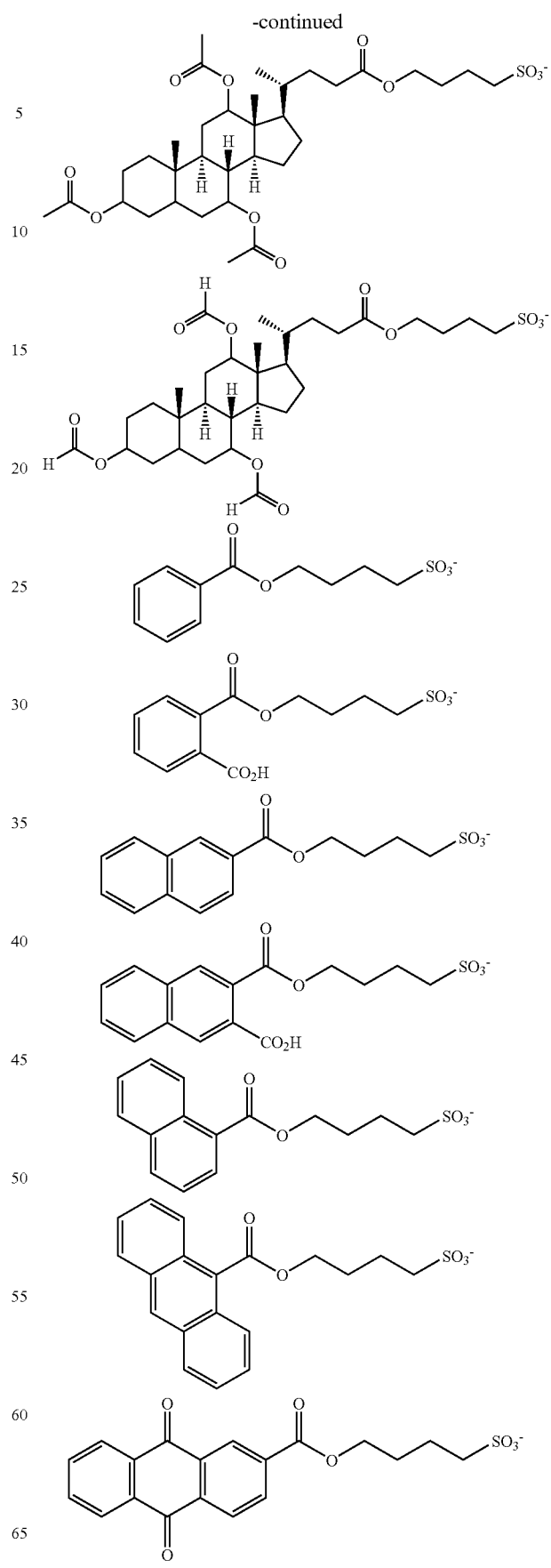

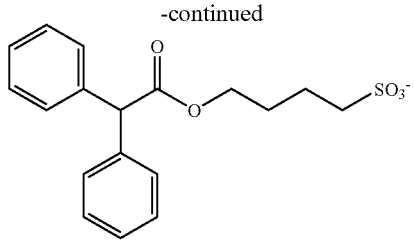

One of the distinguishable features of the invention is that the structure represented by $R^1$ or A can be easily altered by the technique to be described later. Due to high freedom of structural alteration, the desired properties may be easily tailored by alteration of acyl group. This makes it possible to select a PAG wherein $R^1$ or A has an optimum structure in accordance with exposure conditions and the type and construction of polymer.

Understandably, although the sulfonium salts are shown in formula (1) as the cation moiety of the PAG, iodonium salts, ammonium salts and analogous salts can be synthesized by the technique described later, used as the acid generator capable of generating a sulfonic acid having formula (1a), and applied to the resist compositions and patterning process to be described later.

Illustrative examples of iodonium cations include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxy)phenyl)phenyliodonium. Illustrative examples of ammonium salts include tertiary ammonium salts such as trimethylammonium, triethylammonium, tributylammonium, and N,N-dimethylanilinium, and quaternary ammonium salts such as tetramethylammonium, tetraethylammonium, and tetrabutylammonium. The iodonium salt described above may be used as an agent having a photo-acid-generating or thermal acid-generating effect. The ammonium salt may be used as a thermal acid generator.

While the photoacid generator of the invention comprises the sulfonium salt having formula (1), and preferably formula (2), the invention also provides a chemically amplified resist composition comprising an acid generator capable of generating a sulfonic acid having the general formula (1a) in response to radiation such as UV, deep UV, EB, x-ray, excimer laser, γ-ray or synchrotron radiation, or heat.

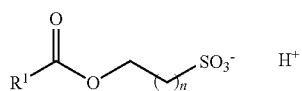
(1a)

Herein $R^1$ and n are as defined above.

In a preferred embodiment, the invention provides a chemically amplified resist composition comprising an acid generator capable of generating a sulfonic acid having the general formula (2a) in response to radiation such as UV, deep UV, EB, x-ray, excimer laser, γ-ray or synchrotron radiation or heat.

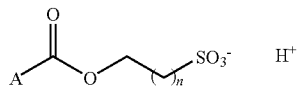
(2a)

Herein A and n are as defined above.

While the acid generators include photoacid generators capable of generating a sulfonic acid having the general formula (1a) or (2a) in response to radiation such as UV, deep UV, EB, x-ray, excimer laser, γ-ray or synchrotron radiation, the photoacid generators are advantageously applicable to the KrF excimer laser, ArF excimer laser, EUV or EB lithography, and more advantageously to the KrF excimer laser or EB lithography.

Now the method for synthesizing the sulfonium salt having formula (1) is described. For example, a sulfonium salt having formula (1) wherein n is 1 may be synthesized through ion exchange between a 2-(acyloxy)ethanesulfonic acid metal salt or 2-(acyloxy)ethanesulfonic acid metal salt to be prepared as described later and a sulfonium salt such as sulfonium halide. For the ion exchange reaction, reference is made to JP-A 2007-145797, for example.

Various 2-(acyloxy)ethanesulfonic acid metal salts may be synthesized by acylating the hydroxyl group of sodium isethionate which is commercially available at reasonable price.

For the acylating reaction, any well-known ester preparation methods including reaction with acylating agents and reaction with carboxylic acid may be applicable. The reaction with acylating agent may preferably be conducted by sequentially or simultaneously adding sodium hydroxyethanesulfonate, an acylating agent (e.g., carboxylic chloride or carboxylic anhydride or mixed acid anhydride of carboxylic acid/trifluoroacetic acid), and a base (e.g., triethylamine, diisopropylethylamine, N,N-dimethylaniline, pyridine or 4-dimethylaminopyridine) to a solvent. Exemplary solvents include chlorinated solvents such as methylene chloride, chloroform and trichloroethylene, hydrocarbons such as hexane, heptane, benzene, toluene, xylene, and cumene, ethers such as dibutyl ether, diethylene glycol diethyl ether, diethylene glycol dimethyl ether, tetrahydrofuran and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide, and hexamethylphosphoric triamide, or a mixture of two or more solvents. Where acid anhydrides are used as the acylating agent, the reaction may be conducted in the presence of an acid catalyst instead of the base, the acid catalyst being selected from mineral acids (e.g., hydrochloric acid, hydrobromic acid, sulfuric acid and nitric acid), and organic acids (e.g., oxalic acid, trifluoroacetic acid, methanesulfonic acid, benzenesulfonic acid and p-toluenesulfonic acid). For the acylation reaction, an appropriate temperature may be selected in accordance with the type of acylating agent and reaction conditions. The reaction temperature usually ranges from −50° C. to around the boiling point of the solvent, and preferably from −20° C. to room temperature. The amount of acylating agent used varies depending on its structure and is usually 1 to 40 moles, and preferably 1 to 5 moles per mole of the alcohol compound.

The reaction with carboxylic acid is dehydration reaction between a corresponding carboxylic acid and hydroxyethanesulfonic acid, which is generally carried out in the presence of an acid catalyst. The amount of carboxylic acid used varies depending on its structure and is usually 1 to 40 moles, and preferably 1 to 5 moles per mole of the alcohol compound. Suitable acid catalysts include mineral acids such as hydrochloric acid, hydrobromic acid, sulfuric acid and nitric acid and organic acids such as oxalic acid, trifluoroacetic acid, methanesulfonic acid, benzenesulfonic acid, and p-toluenesulfonic acid, which may be used alone or in admixture. The acid catalyst may be used in an amount of 0.001 to 1 mole, and preferably 0.01 to 0.05 mole per mole of the alcohol compound. The solvent may be the same as exemplified for the reaction with esterifying agents. Often, the reaction temperature preferably ranges from −50° C. to around the boiling point of the solvent. It is acceptable to carry out the reaction in a solvent containing a hydrocarbon such as hexane, heptane, benzene, toluene, xylene or cumene while azeotroping off the water generated during the reaction. In this embodiment, water may be distilled off while refluxing at the boiling point of the solvent under atmospheric pressure. Water may also be distilled off at a temperature below the boiling point under vacuum.

In the preferred procedure using the acylating agent, a mixed acid anhydride of carboxylic acid/trifluoroacetic acid is prepared from trifluoroacetic anhydride and carboxylic acid in trifluoroacetic acid solvent, and the mixed acid anhydride as the acylating agent is reacted with sodium isethionate, thereby synthesizing the desired sodium salt of sulfoethyl carboxylic acid. In general, sodium isethionate has a low solvent solubility and is difficult to carry out esterifying reaction briefly in high yields. However, since sodium isethionate has a high solubility in trifluoroacetic acid, the esterifying reaction by the above procedure can take place within a short time in high yields. This procedure is described in JP-A 2001-106651.

Besides the above procedure, the following procedure may be employed to produce a sulfonium salt of sulfoethyl carboxylic acid. First, a metal salt of sulfoethyl carboxylic acid which is commercially available is ion exchanged with a sulfonium salt, whereupon the acyl group is subjected to ester hydrolysis or solvolysis to produce a sulfonium salt of isethionic acid. Subsequently, the sulfonium salt of isethionic acid is esterified by the well-known acylating technique described above, thereby synthesizing the desired sulfonium salt of sulfoethyl carboxylic acid. Since the sulfonium salt of isethionic acid has a higher solvent solubility than the sodium salt thereof, reaction smoothly runs even by the well-known acylating technique. An exemplary metal salt of sulfoethyl carboxylic acid which is commercially available is sodium salt of sulfoethyl methacrylic acid. The process is outlined below.

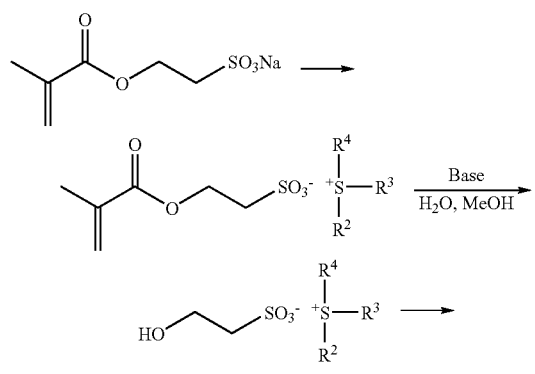

-continued

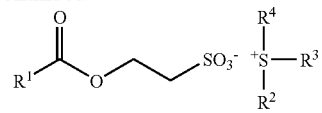

Herein $R^1$, $R^2$, $R^3$, and $R^4$ are as defined above. Me is Methyl.

Where n in formula (1) or (2) is 2, a desired sulfonium salt of sulfopropyl carboxylic acid may be synthesized by a similar procedure. Suitable intermediate reactants are readily available in the market and include sodium 3-hydroxypropanesulfonate and potassium salt of 3-sulfopropyl methacrylate.

Alternatively, a sulfonium salt of sulfopropyl carboxylic acid may be obtained from ring-opening reaction of a sultone with the aid of a metal salt of carboxylic acid. This is followed by cation exchange to form a sulfonium salt having formula (1) or (2). Suitable sultone compounds are readily available in the market and include propanesultone and 1,4-butanesultone. On use of propanesultone, a sulfonium salt having formula (1) or (2) wherein n=2 is eventually obtainable. On use of 1,4-butanesultone, a sulfonium salt having formula (1) or (2) wherein n=3 is eventually obtainable. The process involved is simple and inexpensive.

As is evident from the foregoing, the compounds of the invention are advantageous in that they can be synthesized without undue steps or expensive reactants.

Sulfonium salts other than the triphenylsulfonium and iodonium salts may be synthesized by a similar process.

Sulfonium salts and iodonium salts as the starting reactant may be synthesized in accordance with the teachings of The Chemistry of Sulfonium Group, Part 1, John Wiley & Sons (1981), Advanced Photochemistry, Vol. 17, John Wiley & Sons (1992), J. Org. Chem., 53, 5571-5573, 1988, JP-A H07-25846, JP-A H08-311018, JP-A H09-15848, JP-A 2001-122850, JP-A 2001-181221, JP-A 2002-193887, and JP-A 2002-193925. Also, onium cations having an acryloyloxy or methacryloyloxy group as a polymerizable substituent may be synthesized in accordance with the teachings of JP-A H04-230645 and JP-A 2005-84365 by reacting any existing hydroxyphenyldiphenylsulfonium halide with acryloyl chloride or methacryloyl chloride under basic conditions.

The chemically amplified resist composition in the second aspect of the invention is defined as comprising an acid generator capable of generating a sulfonic acid having the general formula (1a) or (2a) in response to high-energy radiation. The resist composition is sensitive to radiation such as UV, deep UV, EB, x-ray, excimer laser, γ-ray or synchrotron radiation and suited for use in the microfabrication of integrated circuits. The resist composition may be of either positive or negative type. The resist composition of positive type is preferred from the standpoint of resolution or the like.

Broadly stated, the positive resist composition comprises an acid generator in the form of a sulfonium salt having formula (1), and preferably formula (2), or an acid generator capable of generating a sulfonic acid having formula (1a), and preferably formula (2a), to be referred to as "inventive acid generator," hereinafter. In addition to the inventive acid generator, the positive resist composition in a preferred embodiment further comprises:

(A) a base resin having a solubility in alkaline developer which changes under the action of acid,
(B) an organic solvent, and optionally,
(C) an acid generator other than the inventive acid generator,
(D) a quencher, and
(E) a surfactant.

Likewise, the negative resist composition comprises an acid generator in the form of a sulfonium salt having formula (1), and preferably formula (2), or an acid generator capable of generating a sulfonic acid having formula (1a), and preferably formula (2a), to be referred to as "inventive acid generator," hereinafter. In addition to the inventive acid generator, the negative resist composition in a preferred embodiment further comprises:

(A') a base resin which is soluble in alkaline developer, (B) an organic solvent, (F) a crosslinker for inducing crosslinkage under the action of an acid, and optionally, (C) an acid generator other than the inventive acid generator, (D) a quencher, and (E) a surfactant.

Now these components are described in detail.

In the resist composition, the inventive acid generator is preferably used in an amount of 0.1 to 10 parts, and more preferably 0.1 to 5 parts by weight per 100 parts by weight of component (A) or (A').

For the positive resist composition, component (A) is a base resin having a solubility in an alkaline developer that changes under the action of an acid. The preferred base resins are polymers comprising recurring units of one or more types selected from the following general formulae (11) to (15).

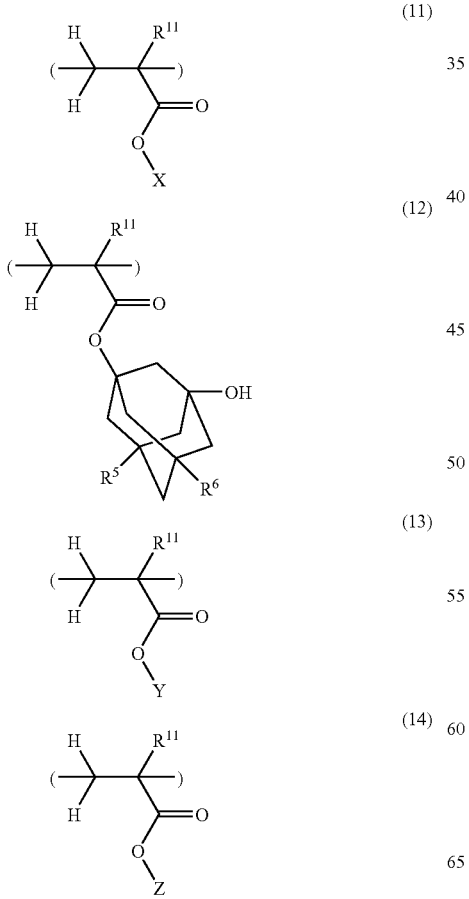

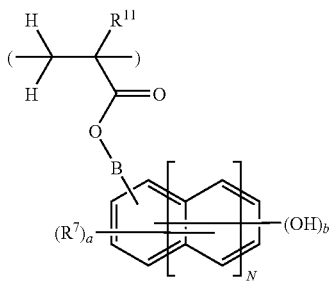

Herein $R^{11}$ is hydrogen, fluorine, methyl or trifluoromethyl. $R^5$ and $R^6$ are each independently hydrogen or hydroxyl. X is an acid labile group. Y is a lactone structure-containing substituent group. Z is hydrogen, $C_1$-$C_{15}$ fluoroalkyl, or $C_1$-$C_{15}$ fluoroalcohol-containing substituent group. N is an integer of 0 to 2. $R^7$ is hydrogen or $C_1$-$C_{10}$ alkyl. B is a single bond or an optionally oxygen-substituted divalent organic group of 1 to 10 carbon atoms. The subscript a is an integer of 0 to 3, and b is an integer of 1 to 3.

Under the action of an acid, a polymer comprising recurring units of formula (11) is decomposed to generate a carboxylic acid and turns into an alkali-soluble polymer.

The acid labile groups represented by X may be selected from a variety of such groups, for example, groups of the following general formulae (L1) to (L4) and (L2-2), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

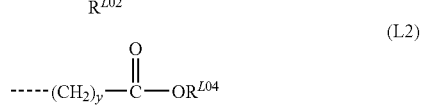

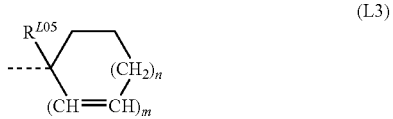

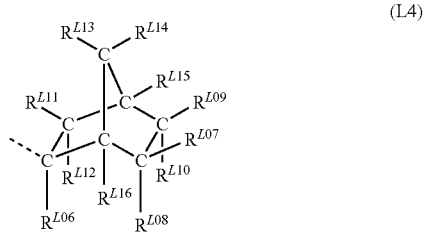

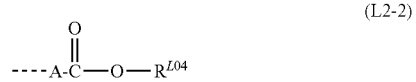

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Examples of the substituted alkyl groups are shown below.

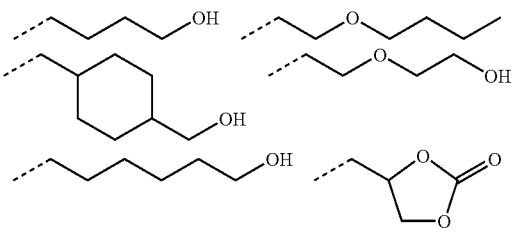

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L2-2), $R^{L04}$ is as defined above, and examples of the moiety of the formula:

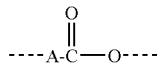

are given below.

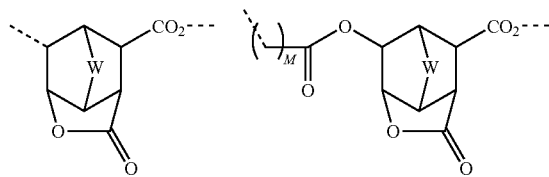

Herein W is an oxygen atom or $CH_2$, and M is an integer of 1 to 3.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m is 0 or 1, n is 0, 1, 2 or 3, and 2 m+n is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

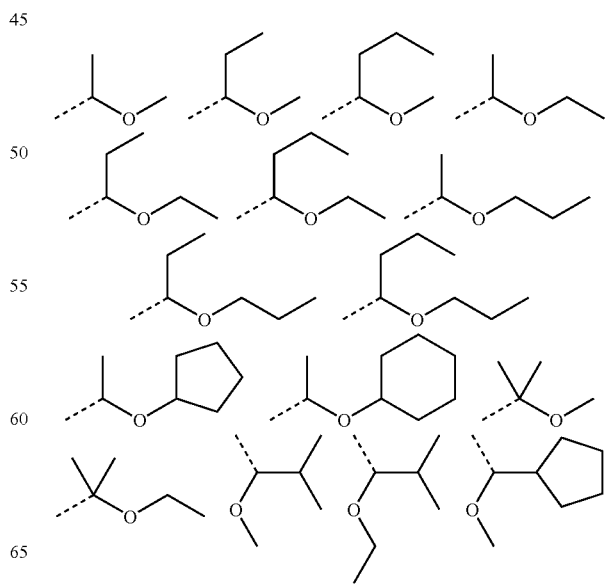

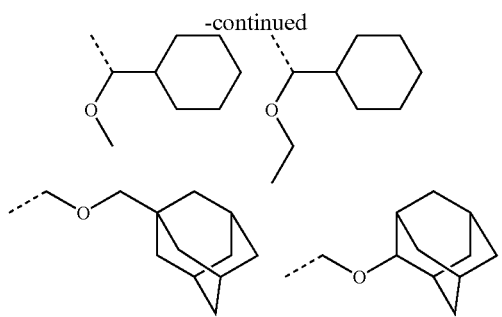

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L2-2) include
9-(tert-butyloxycarbonyl)-5-oxo-4-oxatricyclo[4.2.1.0$^{3,7}$]-nonan-2-yl,
9-(tert-amyloxycarbonyl)-5-oxo-4-oxatricyclo[4.2.1.0$^{3,7}$]nonan-2-yl,
9-(2-(adamantan-1-yl)propan-2-yloxycarbonyl)-5-oxo-4-oxatricyclo[4.2.1.0$^{3,7}$]nonan-2-yl,
9-(1-ethylcyclopentyloxycarbonyl)-5-oxo-4-oxatricyclo-[4.2.1.0$^{3,7}$]nonan-2-yl,
9-(1-butylcyclopentyloxycarbonyl)-5-oxo-4-oxatricyclo-[4.2.1.0$^{3,7}$]nonan-2-yl,
9-(1-ethylcyclohexyloxycarbonyl)-5-oxo-4-oxatricyclo-[4.2.1.0$^{3,7}$]nonan-2-yl,
9-(1-butylcyclohexyloxycarbonyl)-5-oxo-4-oxatricyclo-[4.2.1.0$^{3,7}$]nonan-2-yl,
9-(2-methyl-2-adamantyloxycarbonyl)-5-oxo-4-oxatricyclo-[4.2.1.0$^{3,7}$]nonan-2-yl,
9-(2-ethyl-2-adamantyloxycarbonyl)-5-oxo-4-oxatricyclo-[4.2.1.0$^{3,7}$]nonan-2-yl,
9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yl,
2-(9-(tert-butyloxycarbonyl)-5-oxo-4-oxatricyclo[4.2.1.0$^{3,7}$]-nonan-2-yloxy)-2-oxoethyl,
2-(9-(tert-amyloxycarbonyl)-5-oxo-4-oxatricyclo[4.2.1.0$^{3,7}$]-nonan-2-yloxy)-2-oxoethyl,
2-(9-(2-(adamantan-1-yl)propan-2-yloxycarbonyl)-5-oxo-4-oxatricyclo[4.2.1.0$^{3,7}$]nonan-2-yloxy)-2-oxoethyl,
2-(9-(1-ethylcyclopentyloxycarbonyl)-5-oxo-4-oxatricyclo-[4.2.1.0$^{3,7}$]nonan-2-yloxy)-2-oxoethyl,
2-(9-(1-butylcyclopentyloxycarbonyl)-5-oxo-4-oxatricyclo-[4.2.1.0$^{3,7}$]nonan-2-yloxy)-2-oxoethyl,
2-(9-(1-ethylcyclohexyloxycarbonyl)-5-oxo-4-oxatricyclo-[4.2.1.0$^{3,7}$]nonan-2-yloxy)-2-oxoethyl,
2-(9-(1-butylcyclohexyloxycarbonyl)-5-oxo-4-oxatricyclo-[4.2.1.0$^{3,7}$]nonan-2-yloxy)-2-oxoethyl,
2-(9-(2-methyl-2-adamantyloxycarbonyl)-5-oxo-4-oxatricyclo-[4.2.1.0$^{3,7}$]nonan-2-yloxy)-2-oxoethyl,
2-(9-(2-ethyl-2-adamantyloxycarbonyl)-5-oxo-4-oxatricyclo-[4.2.1.0$^{3,7}$]nonan-2-yloxy)-2-oxoethyl,
2-(9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yloxy)-2-oxoethyl,
4-(9-(tert-butyloxycarbonyl)-5-oxo-4-oxatricyclo[4.2.1.0$^{3,7}$]-nonan-2-yloxy)-4-oxobutyl,
4-(9-(tert-amyloxycarbonyl)-5-oxo-4-oxatricyclo[4.2.1.0$^{3,7}$]nonan-2-yloxy)-4-oxobutyl,
4-(9-(2-(adamantan-1-yl)propan-2-yloxycarbonyl)-5-oxo-4-oxatricyclo[4.2.1.0$^{3,7}$]nonan-2-yloxy)-4-oxobutyl,
4-(9-(1-ethylcyclopentyloxycarbonyl)-5-oxo-4-oxatricyclo-[4.2.1.0$^{3,7}$]nonan-2-yloxy)-4-oxobutyl,
4-(9-(1-butylcyclopentyloxycarbonyl)-5-oxo-4-oxatricyclo-[4.2.1.0$^{3,7}$]nonan-2-yloxy)-4-oxobutyl,
4-(9-(1-ethylcyclohexyloxycarbonyl)-5-oxo-4-oxatricyclo-[4.2.1.0$^{3,7}$]nonan-2-yloxy)-4-oxobutyl,
4-(9-(1-butylcyclohexyloxycarbonyl)-5-oxo-4-oxatricyclo-[4.2.1.0$^{3,7}$]nonan-2-yloxy)-4-oxobutyl,
4-(9-(2-methyl-2-adamantyloxycarbonyl)-5-oxo-4-oxatricyclo-[4.2.1.0$^{3,7}$]nonan-2-yloxy)-4-oxobutyl,
4-(9-(2-ethyl-2-adamantyloxycarbonyl)-5-oxo-4-oxatricyclo-[4.2.1.0$^{3,7}$]nonan-2-yloxy)-4-oxobutyl,
4-(9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yloxy)-4-oxobutyl, etc.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are more preferred.

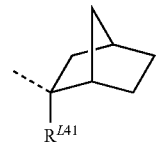

(L4-1)

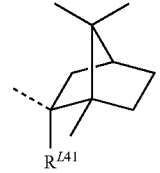

(L4-2)

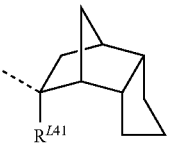

(L4-3)

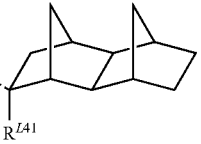

(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

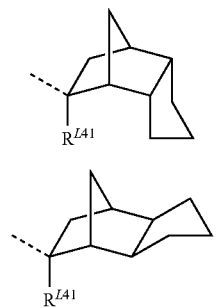

(L4-3-1)

(L4-3-2)

Similarly, the general formula (L4-4) represents one or a mixture of two or more selected from groups having the following general formulas (L4-4-1) to (L4-4-4).

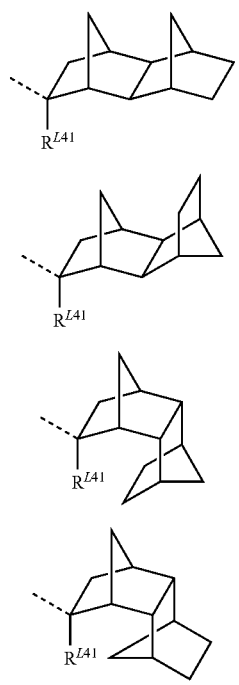

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

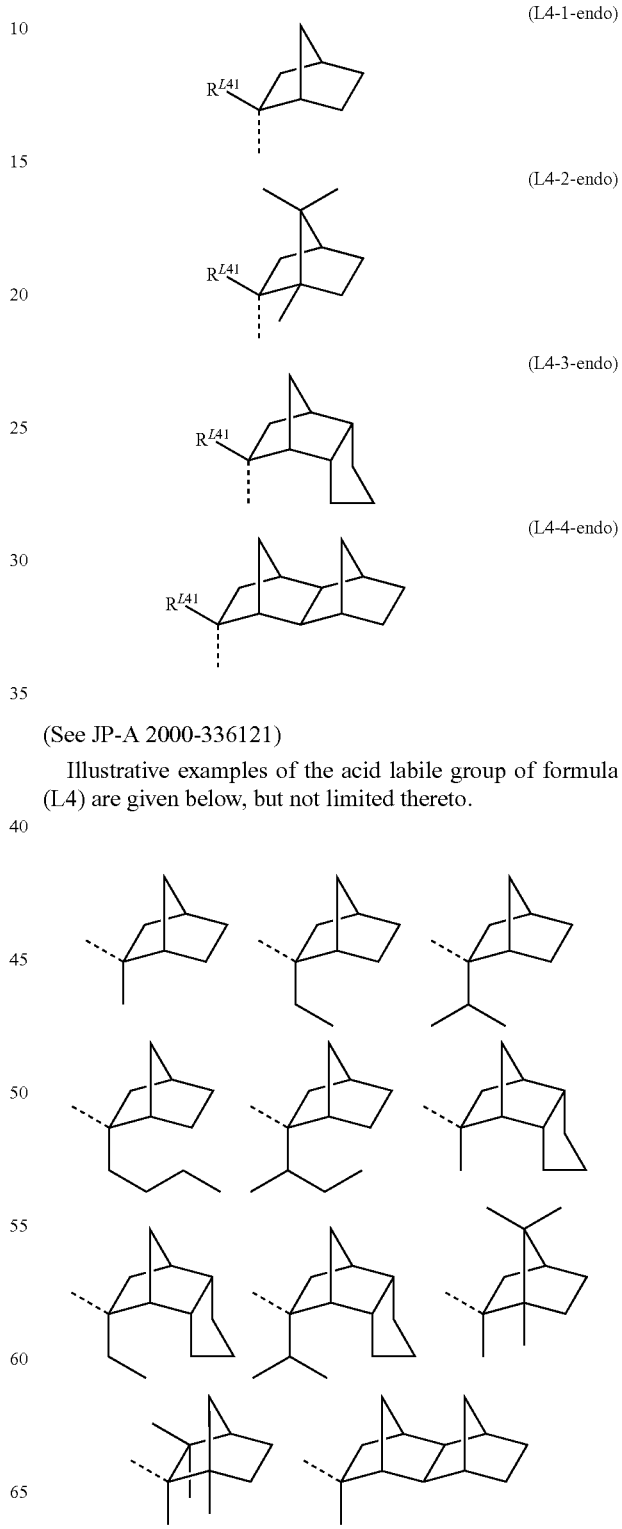

(L4-1-endo)

(L4-2-endo)

(L4-3-endo)

(L4-4-endo)

(See JP-A 2000-336121)

Illustrative examples of the acid labile group of formula (L4) are given below, but not limited thereto.

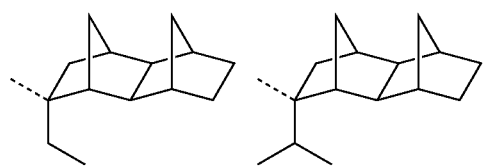
Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.
Illustrative, non-limiting examples of the recurring units of formula (11) are given below. Although only (meth)acrylates are illustrated, those which are separated by a divalent linking group of formula (L2) or (L2-2) are also useful.
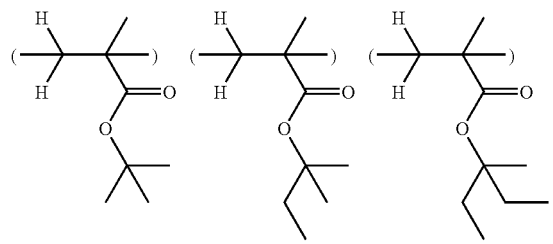
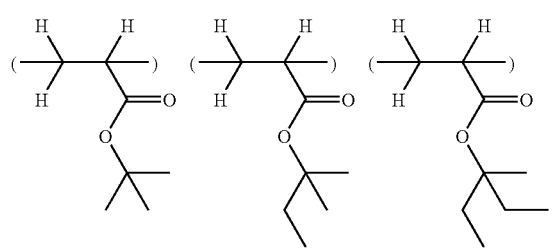
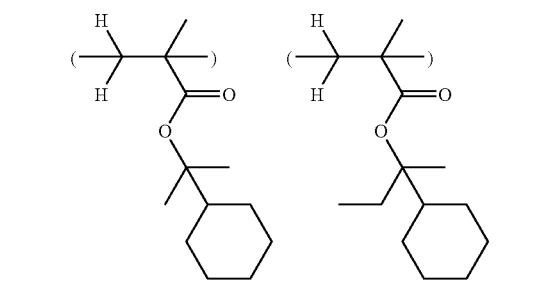
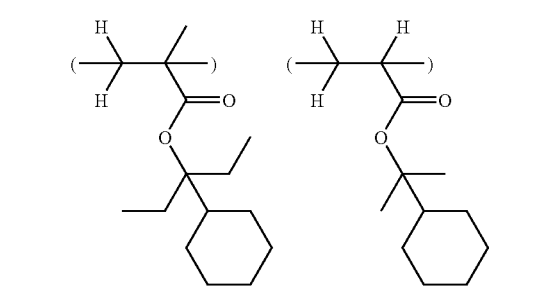
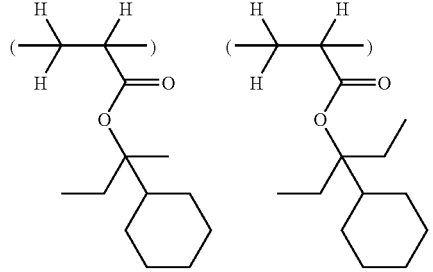
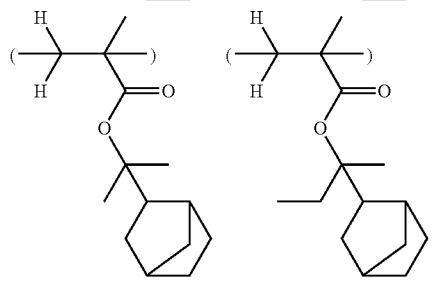
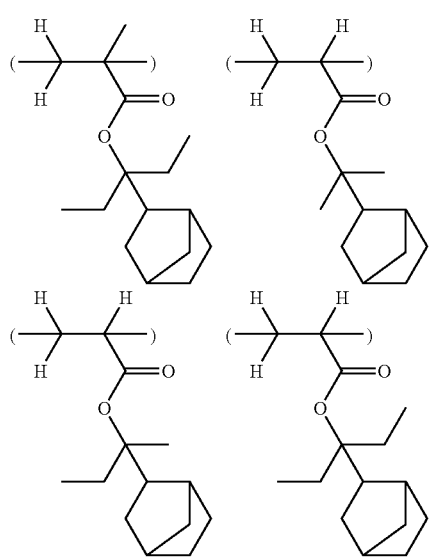
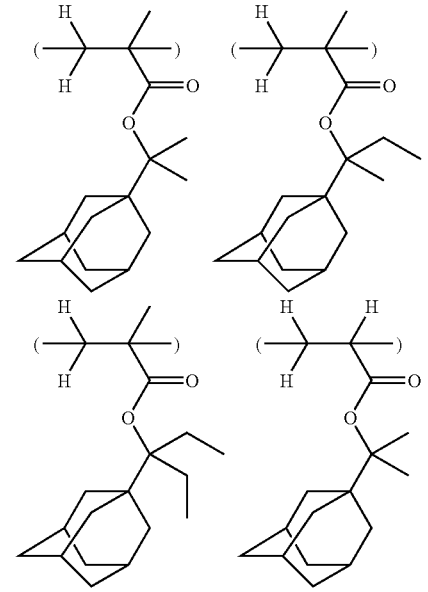

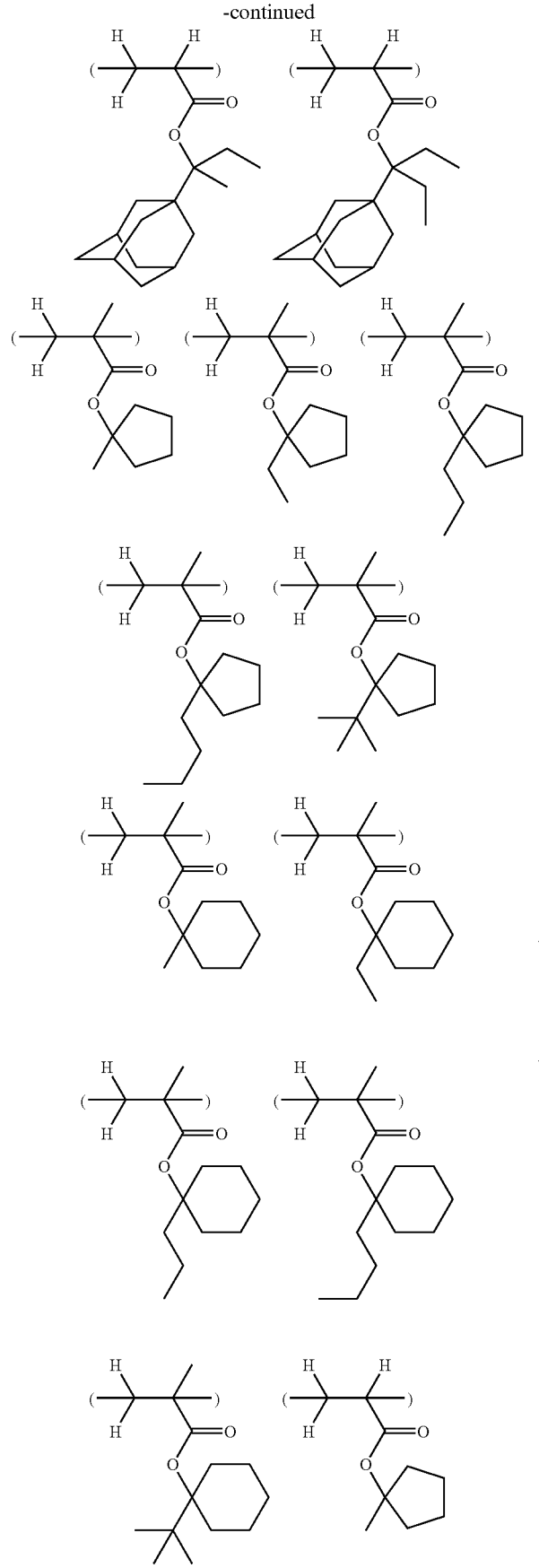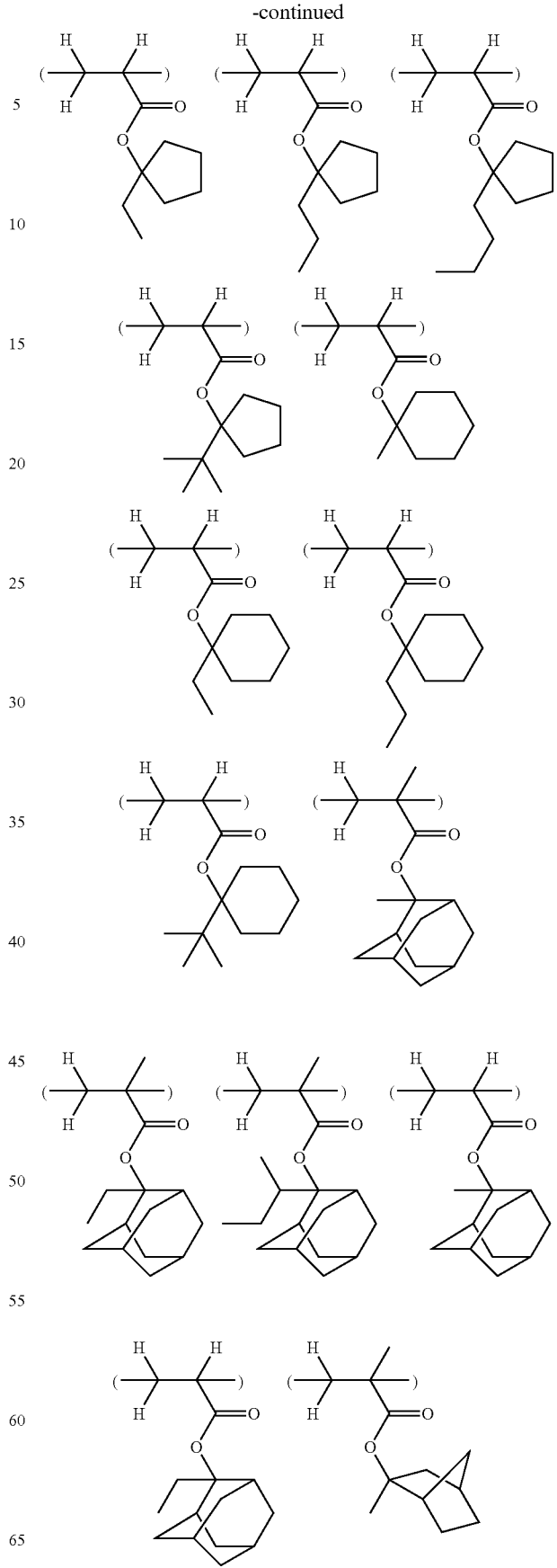

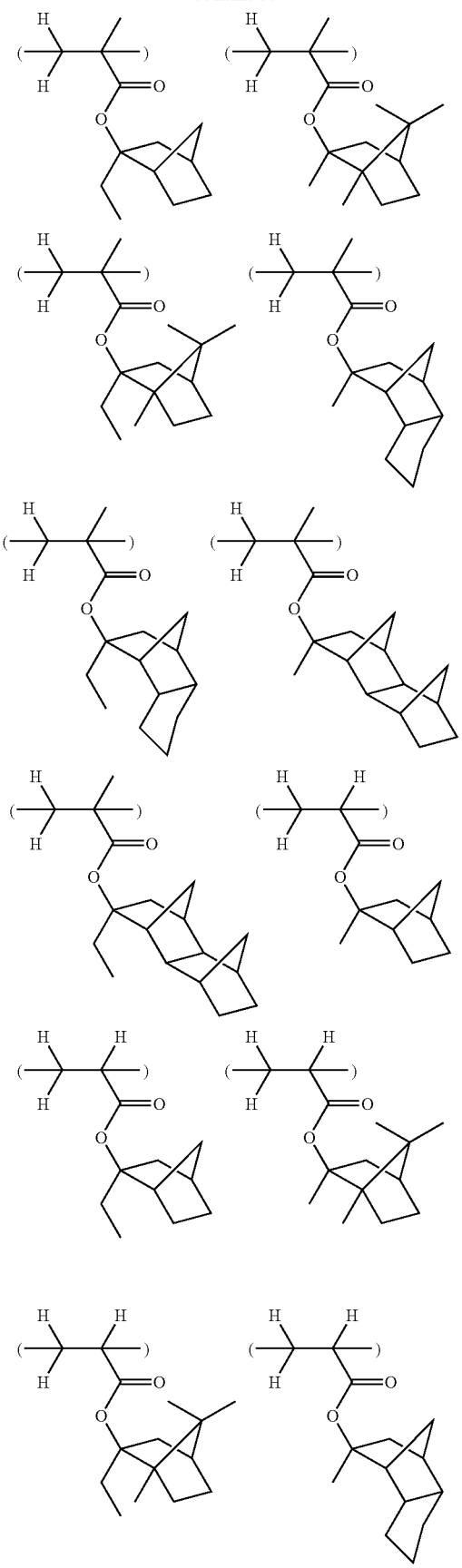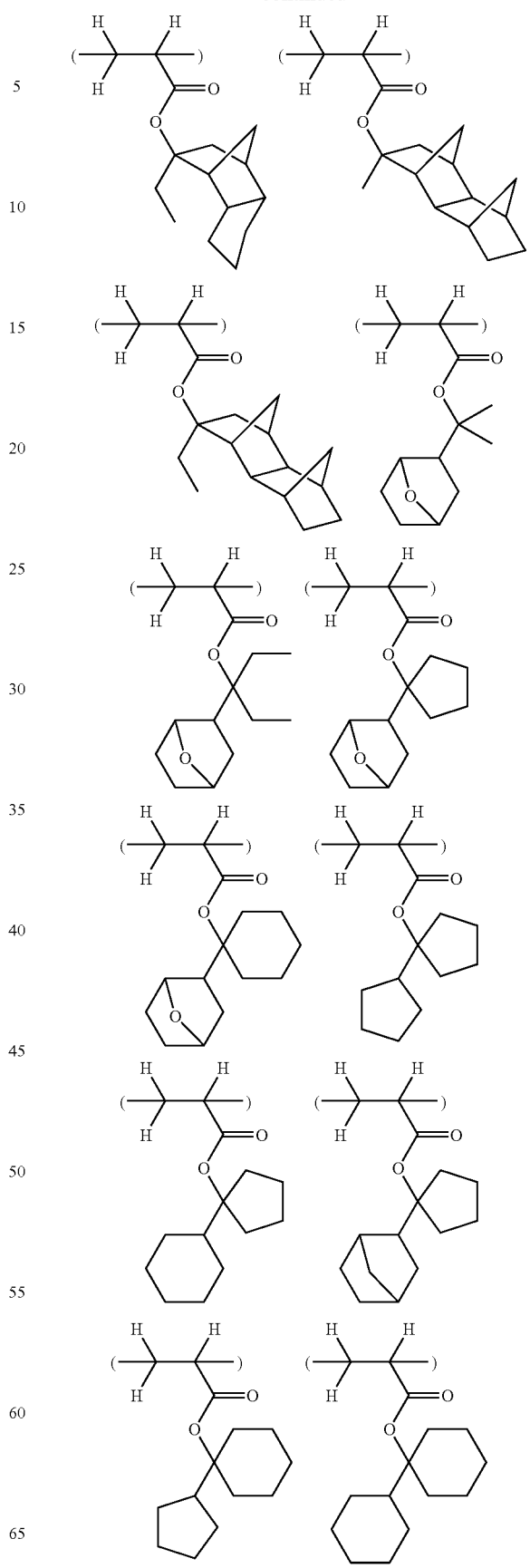

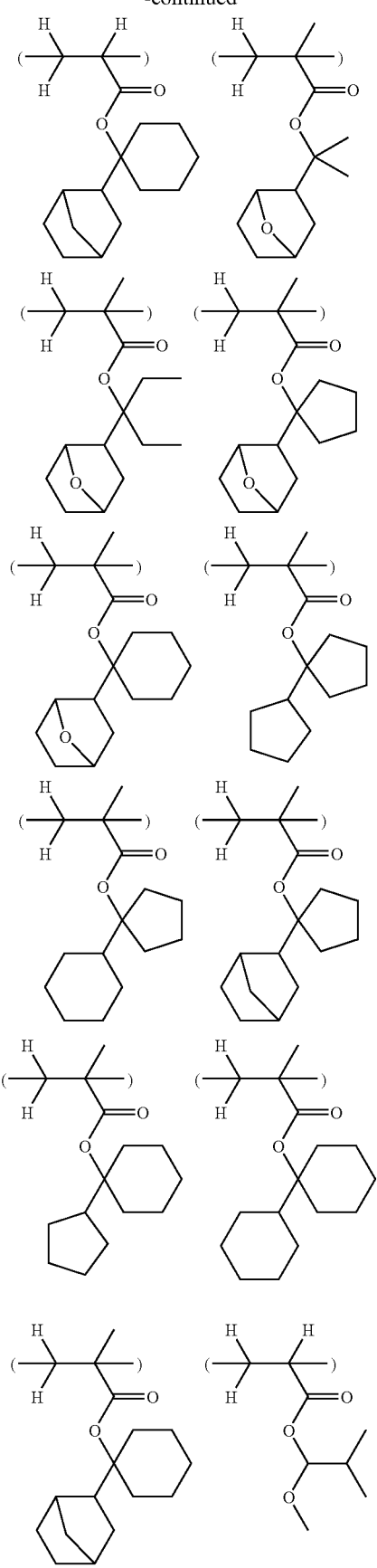
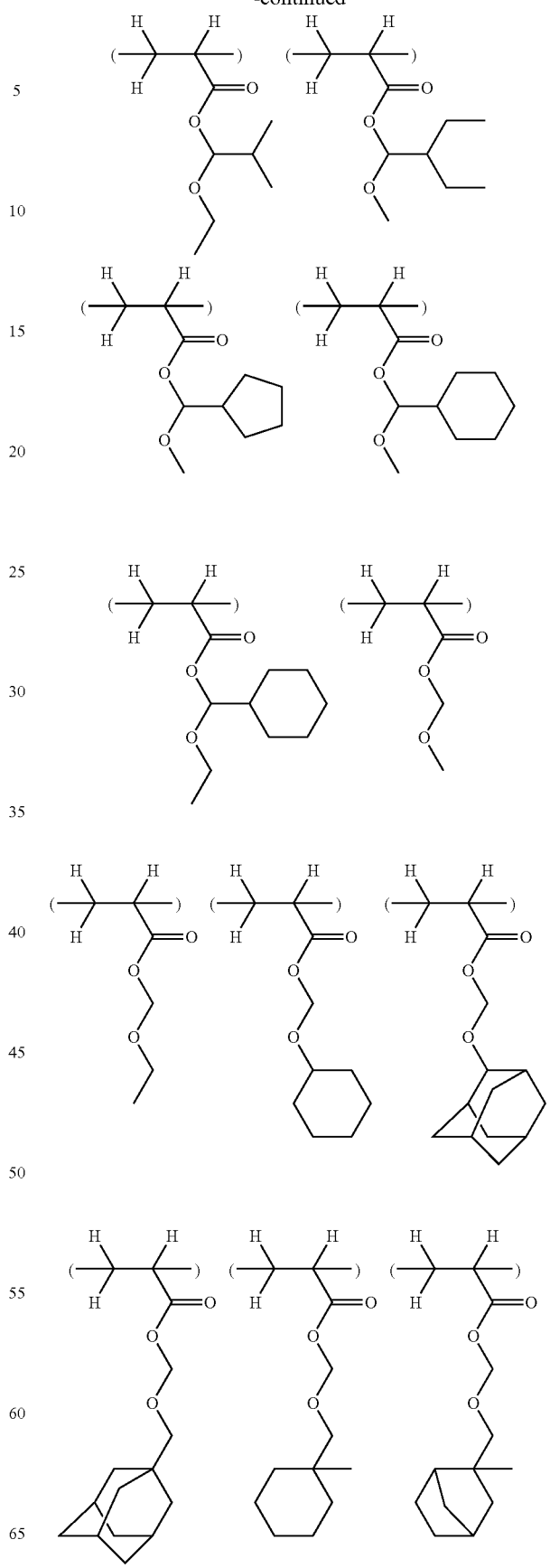

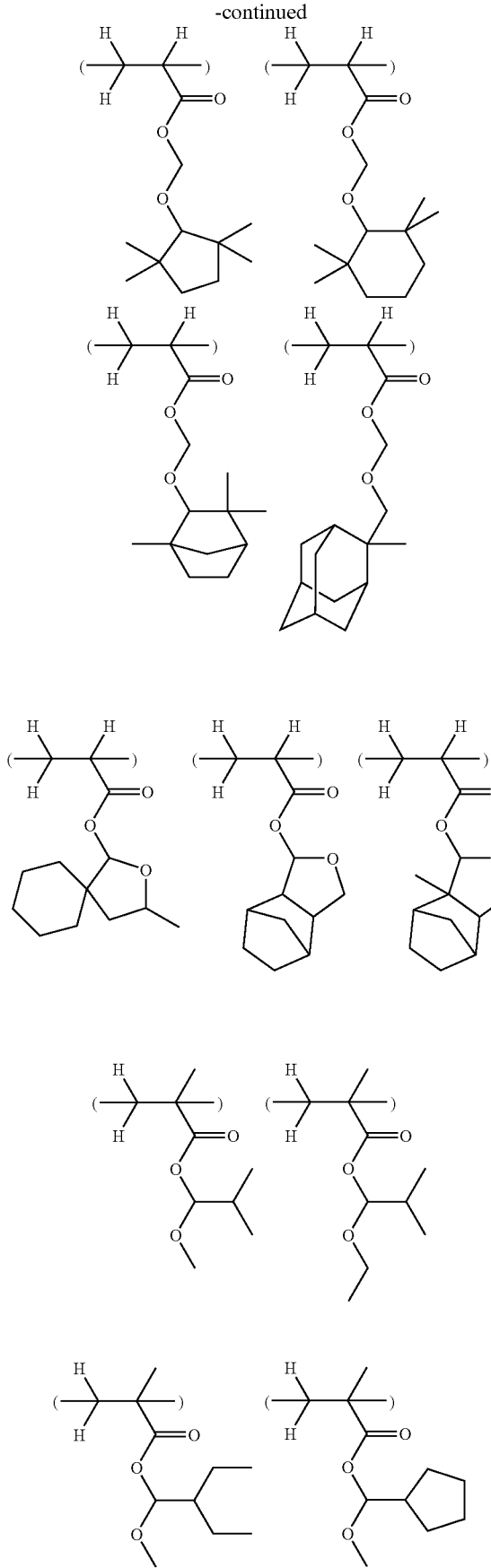
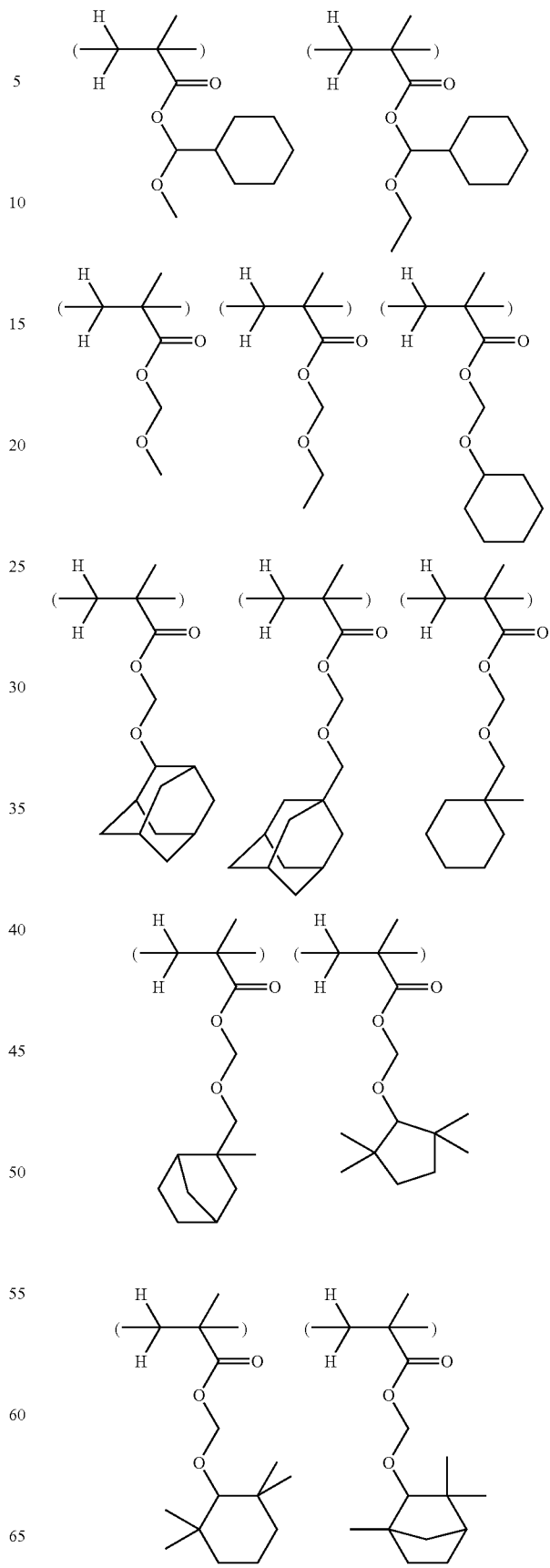

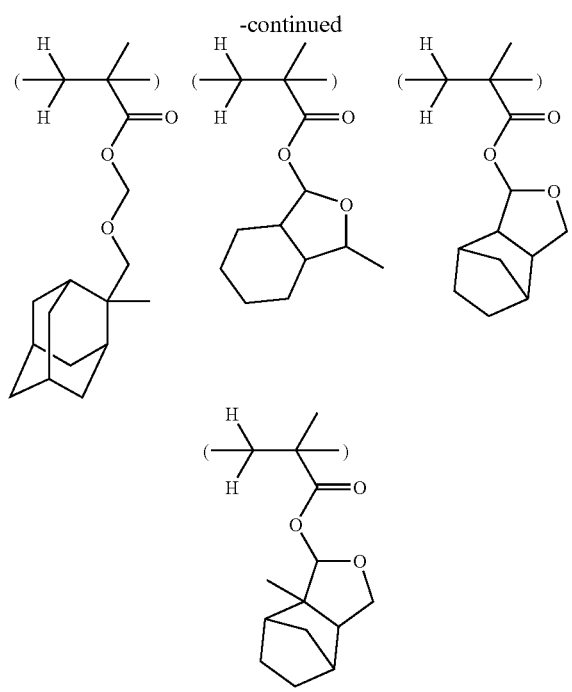

Illustrative, non-limiting examples of the recurring units of formula (12) are given below.

Illustrative examples of the recurring units of formula (13) are given below. Notably, recurring units having an acid labile group are also encompassed. Examples of such units overlap the examples of formula (L2-2) illustrated above as the acid labile group, and they may be used either as the lactone unit or as the acid labile group-containing unit.

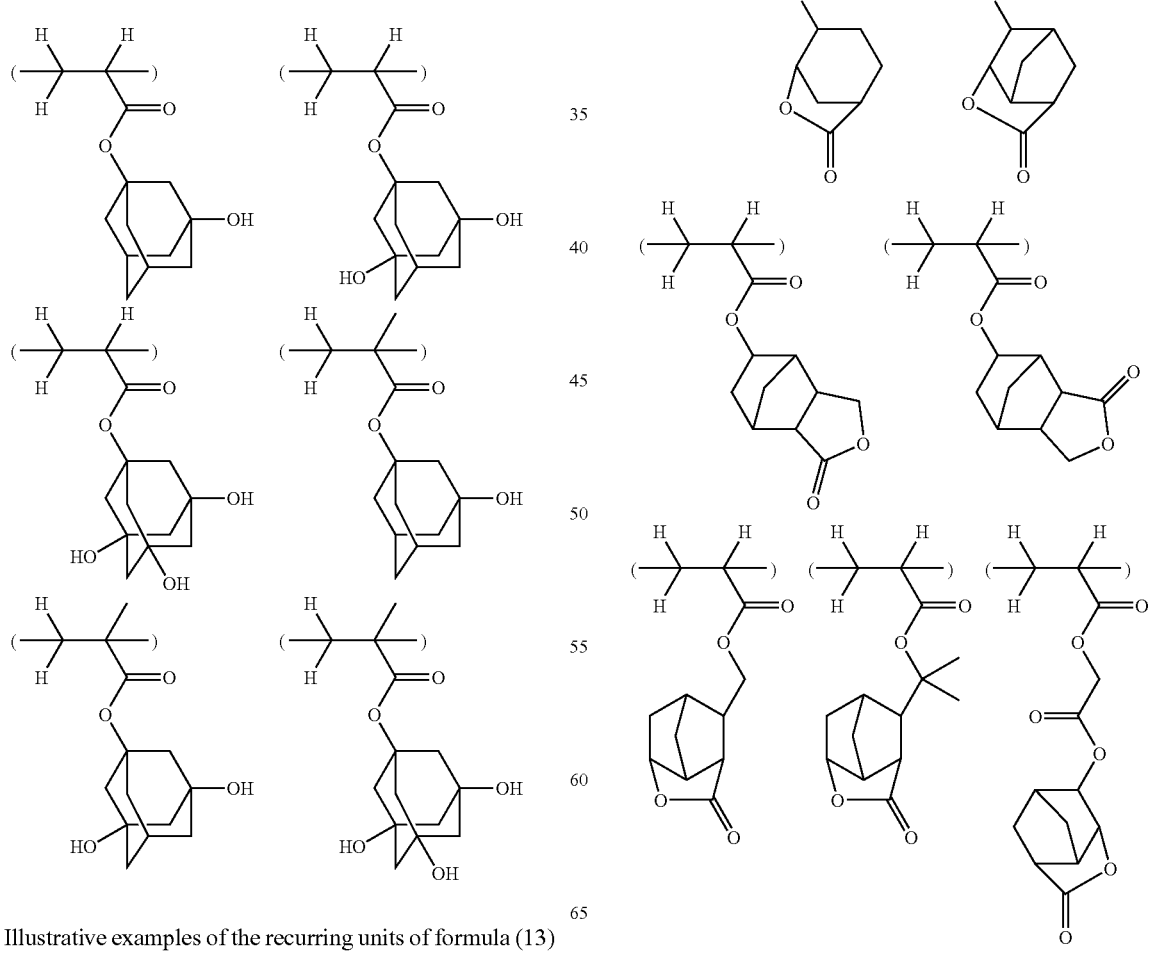

-continued
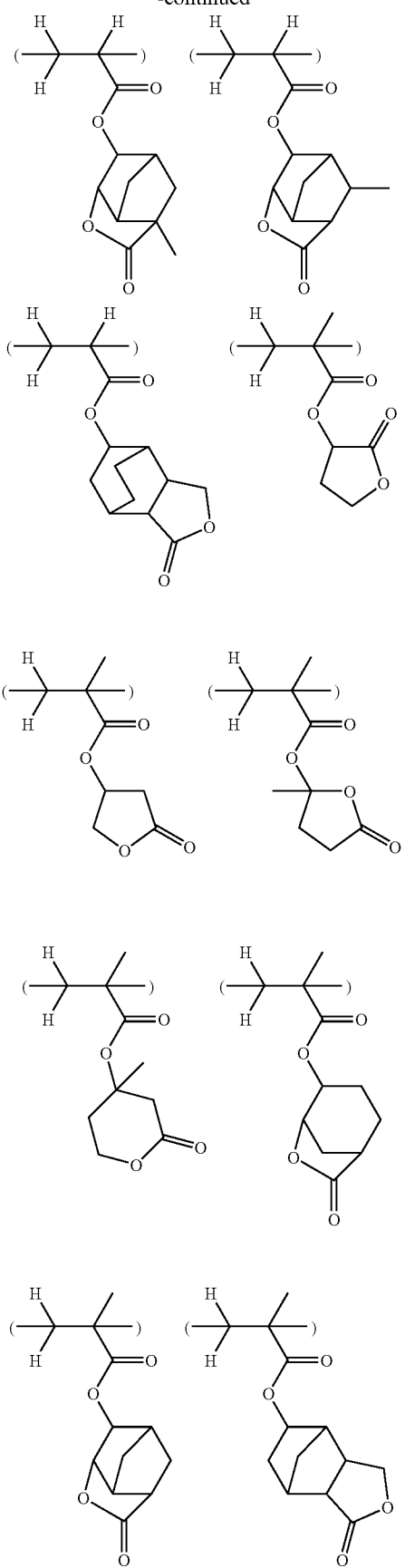
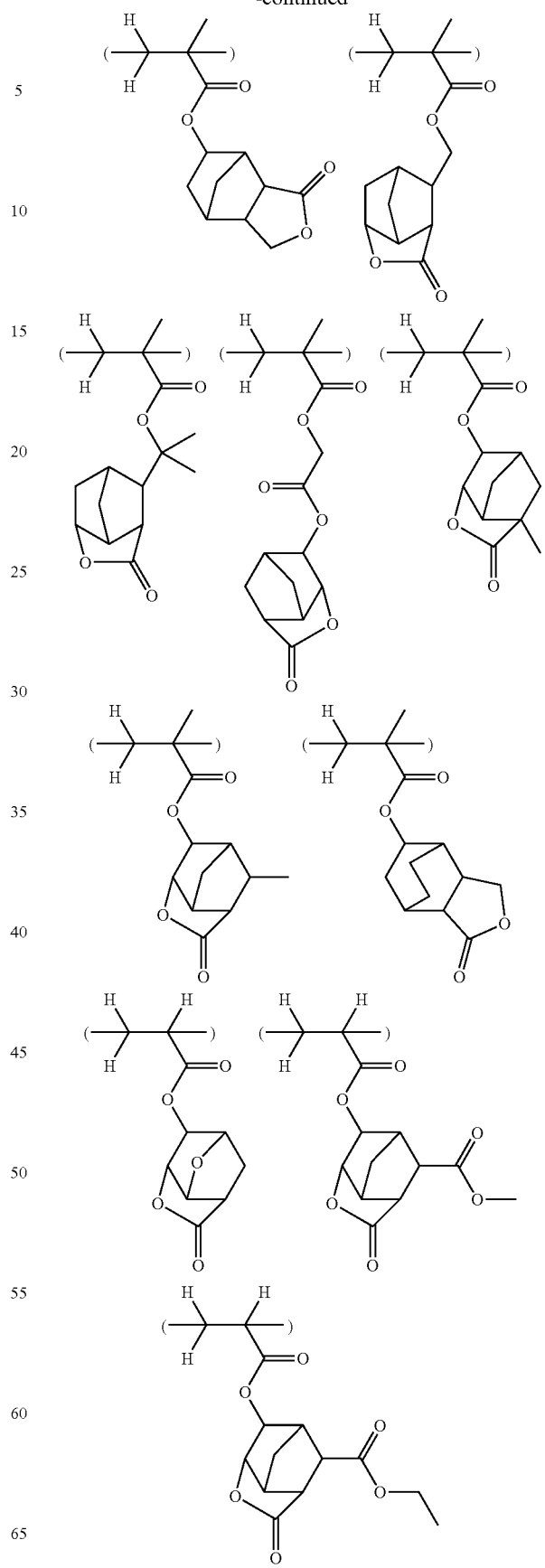

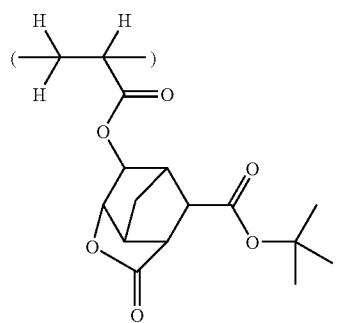
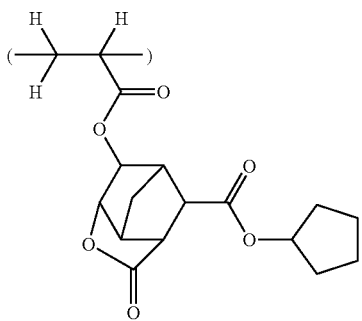
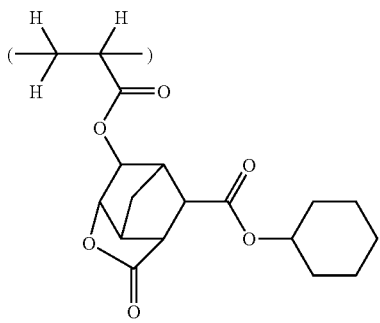
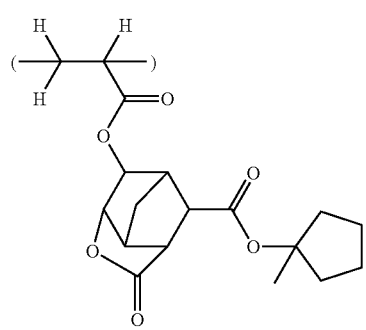
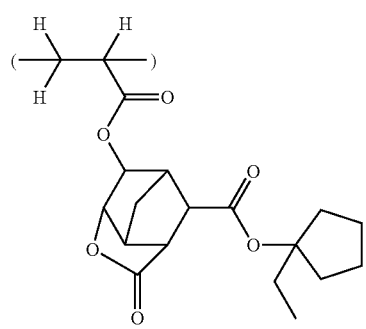
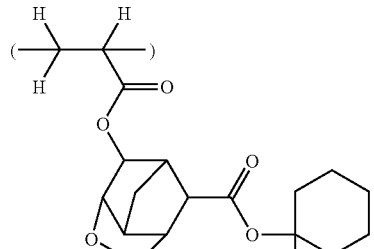
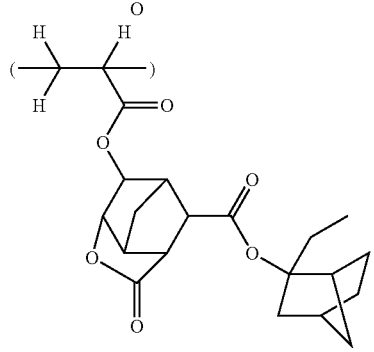
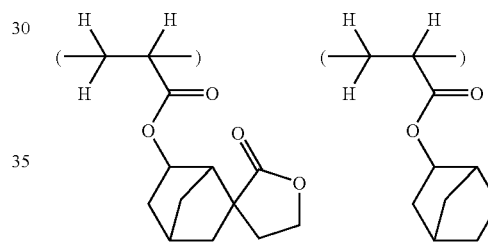
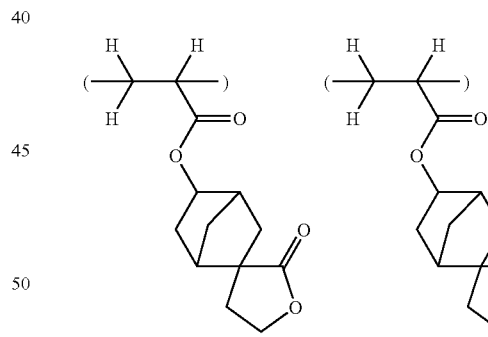
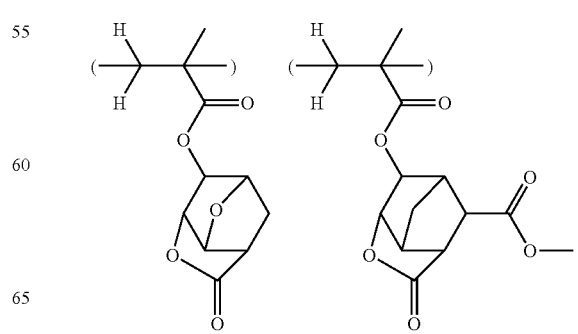

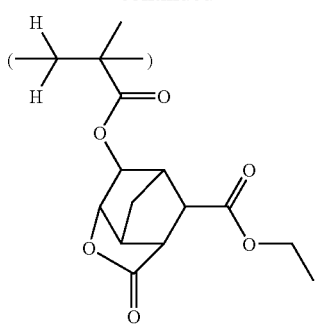
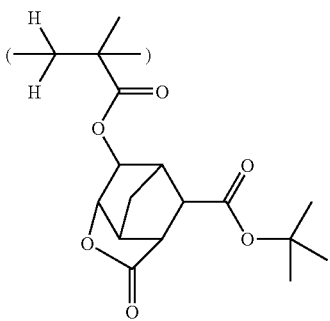
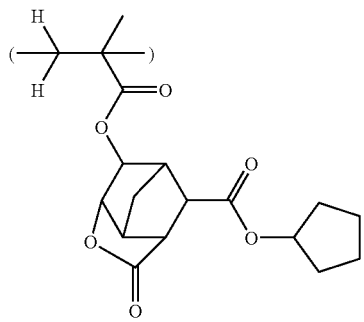
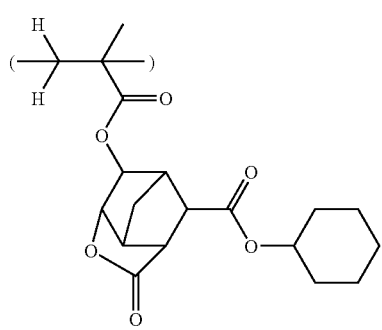
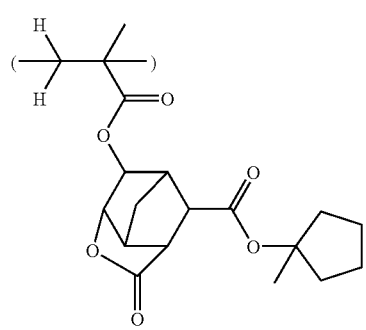
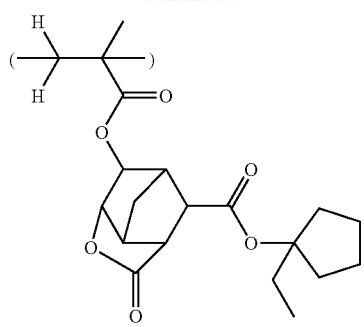
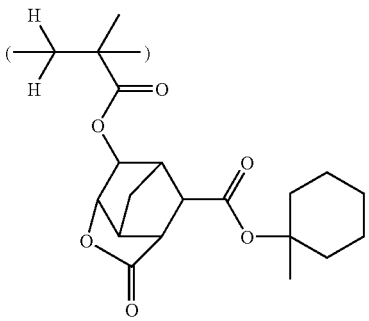
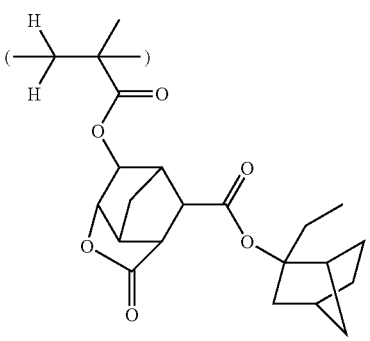
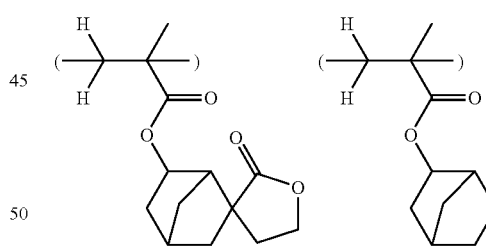
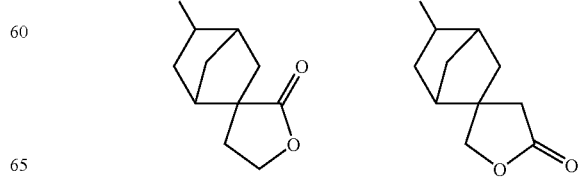

Also included are units of the general formula (5L-1).

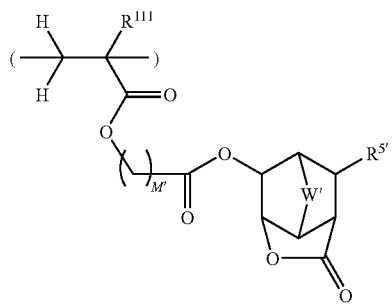

In formula (5L-1), $R^{11}$ is hydrogen, fluorine, methyl or trifluoromethyl, and preferably methyl. $R^{5'}$ is hydrogen or $CO_2R^{5''}$ wherein $R^{5''}$ is hydrogen, halogen or a straight, branched or cyclic $C_1$-$C_{15}$ monovalent hydrocarbon group which may have oxygen. W' is $CH_2$, O or S. M' is an integer of 1 to 3.

Examples of $R^{5''}$ include hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptan-2-yl, 2-ethylbicyclo[2.2.1]heptan-2-yl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-methyltetracyclo[6.2.1.1$^{3,6}$.0$^{2,7}$]dodecan-4-yl, 4-ethyltetracyclo[6.2.1.1$^{3,6}$.0$^{2,7}$]dodecan-4-yl, methoxymethyl, ethoxymethyl, methoxyethyl, ethoxyethyl, and methoxyethoxyethyl, as well as the groups shown below.

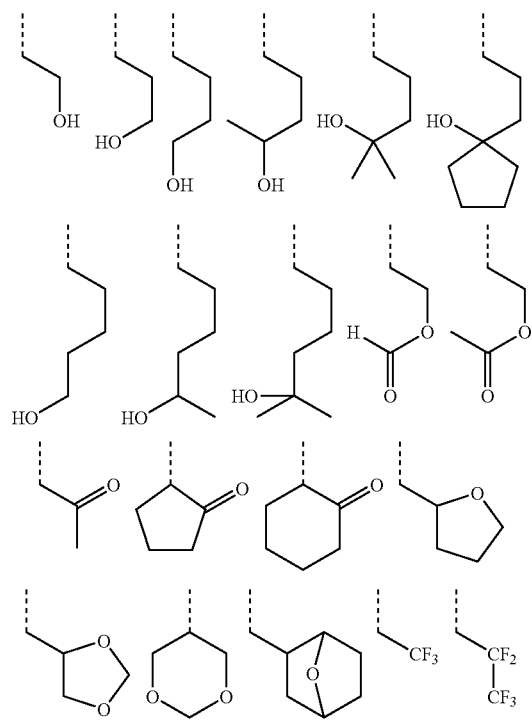

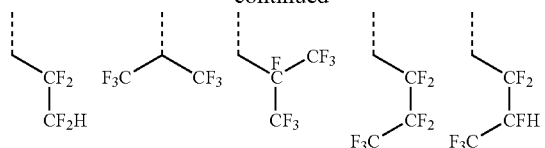
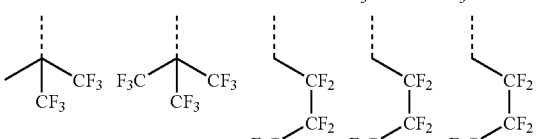
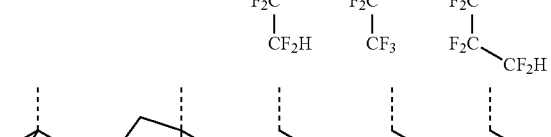
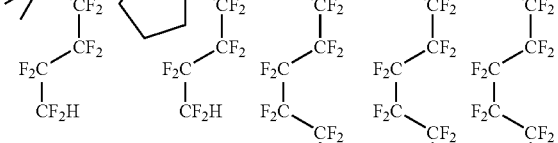
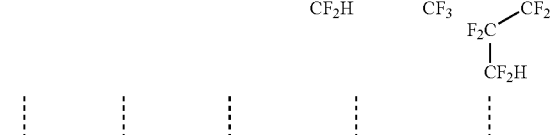
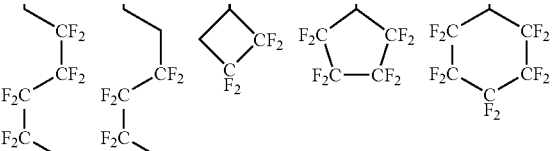

(The Broken Line Denotes a Valence Bond.)

Preferred examples of $R^{5''}$ include methyl, 1-methylcyclopentyl, 1-ethylcyclopentyl, 1-methylcyclohexyl, 1-ethylcyclohexyl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-ethyltetracyclo[6.2.1.1$^{3,6}$.0$^{2,7}$]dodecan-4-yl. Preferably W' is $CH_2$.

Examples of suitable monomers from which recurring units of formula (5L-1) are derived are given below.
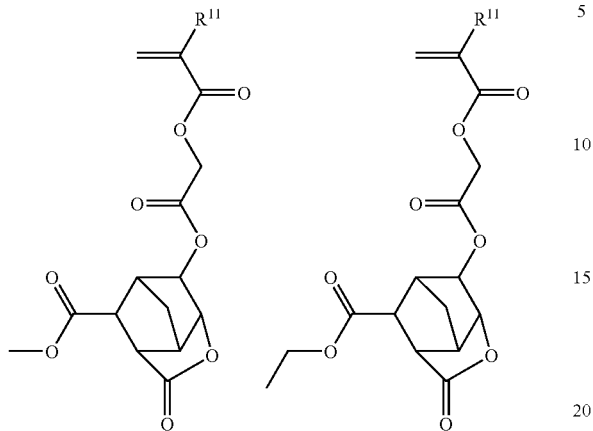
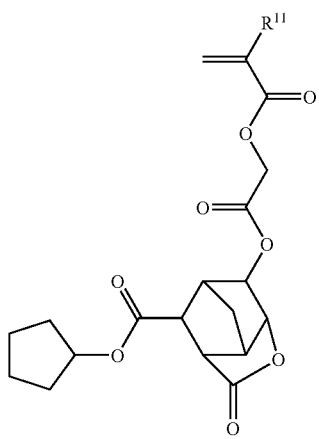
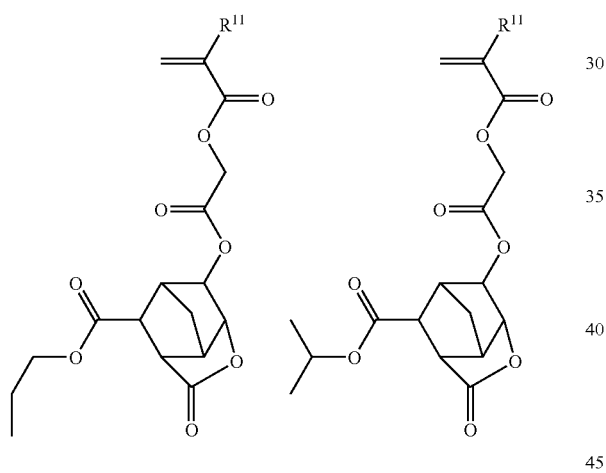
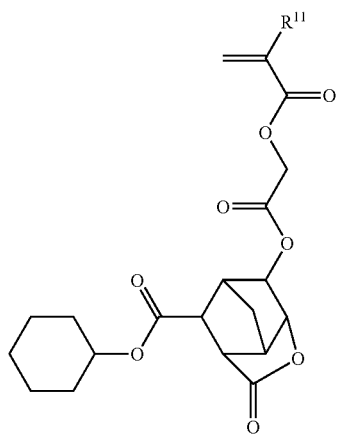
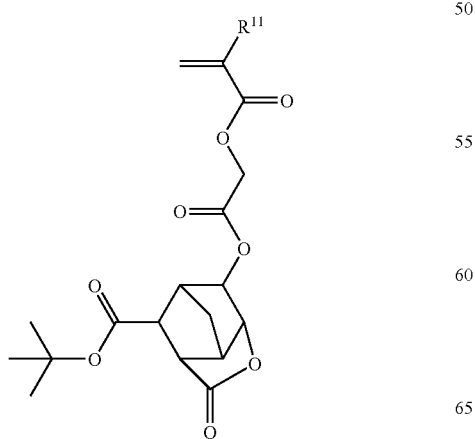
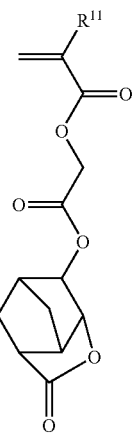

51
-continued
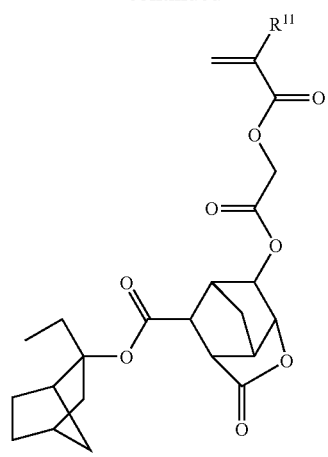
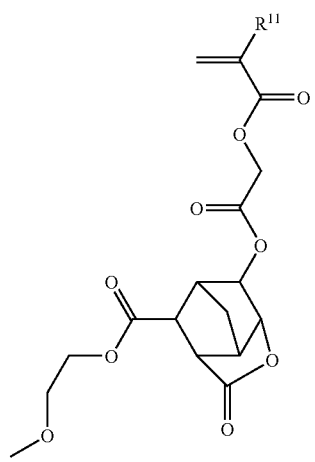
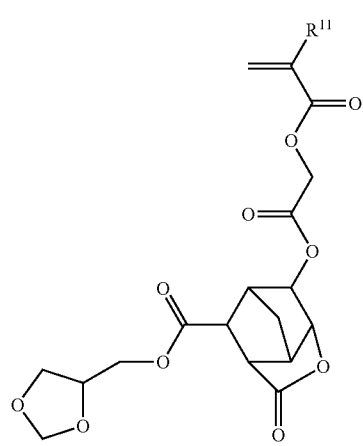
52
-continued
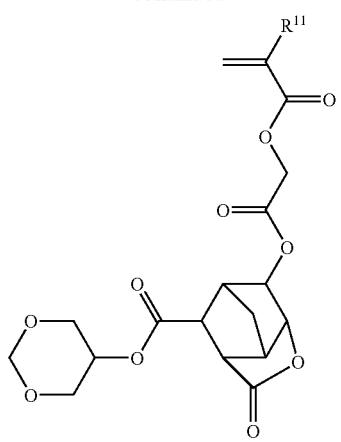
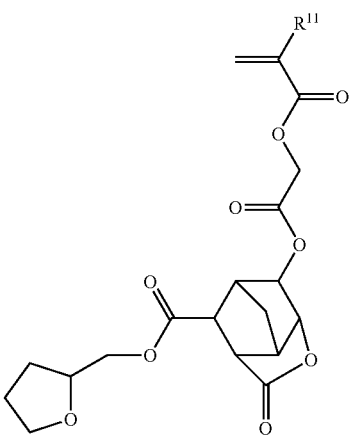
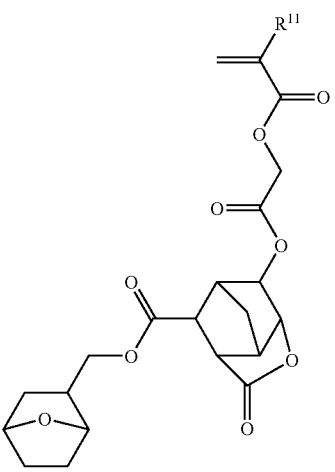

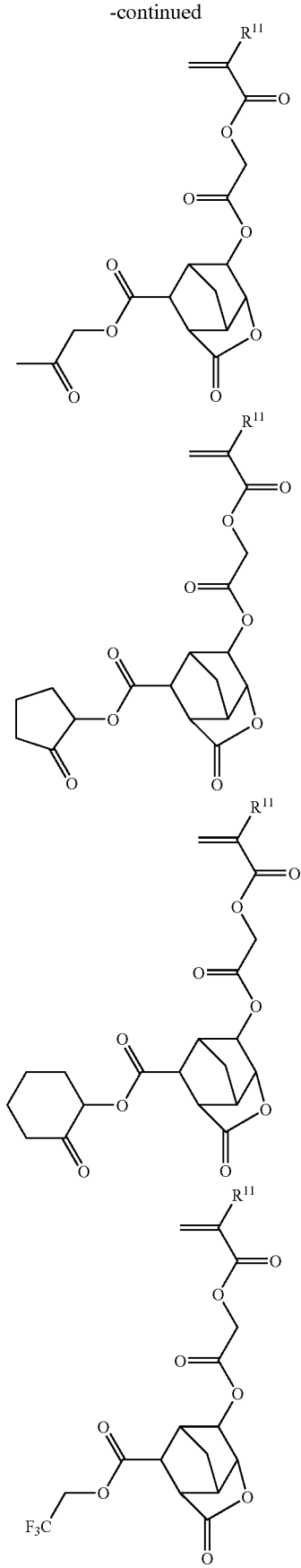
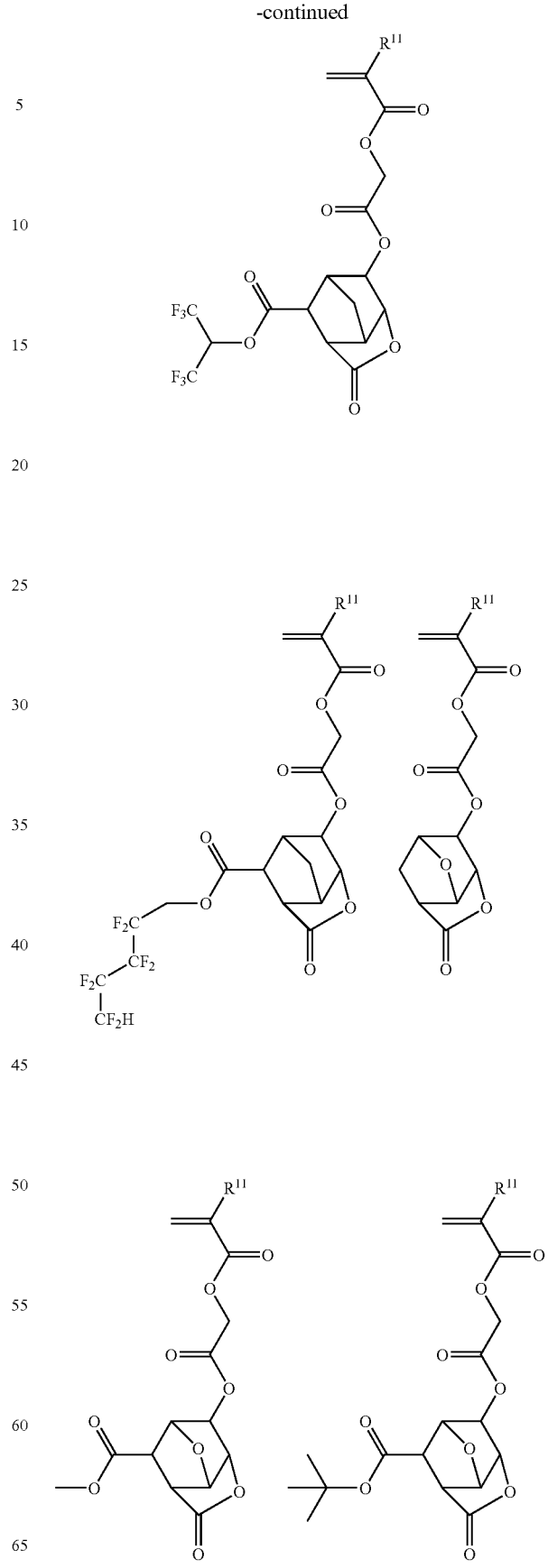

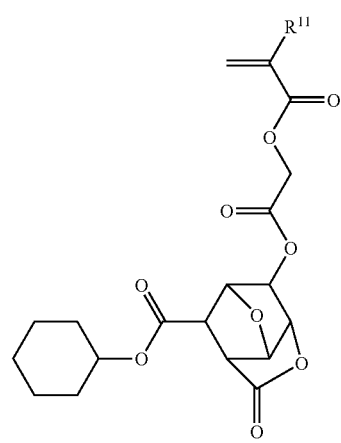
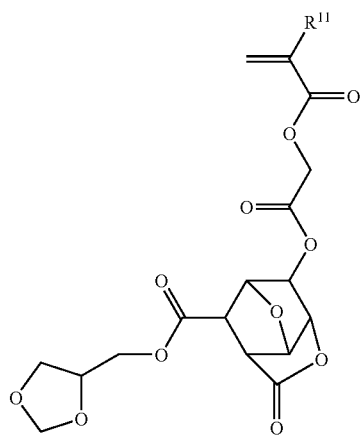
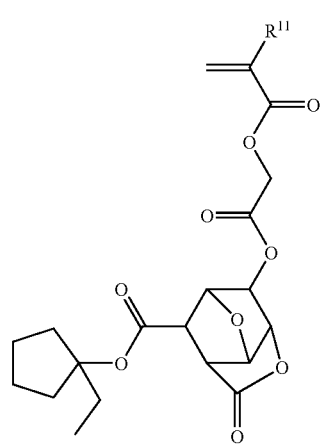
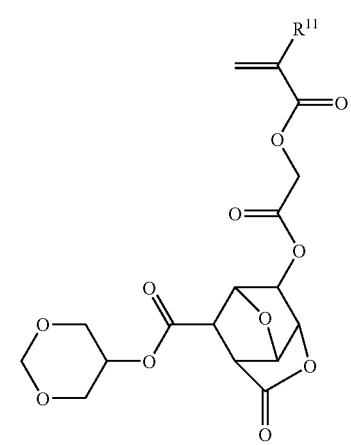
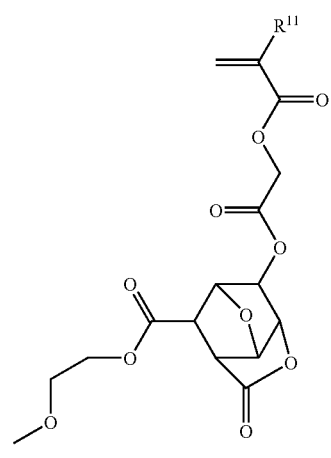
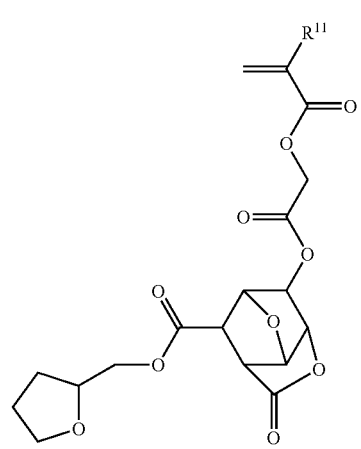

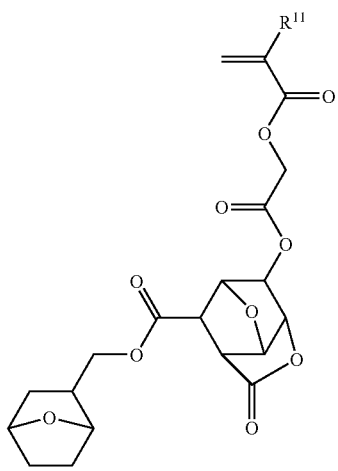
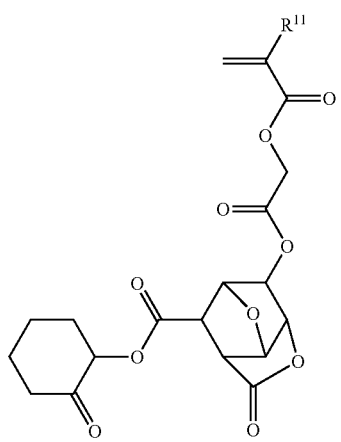
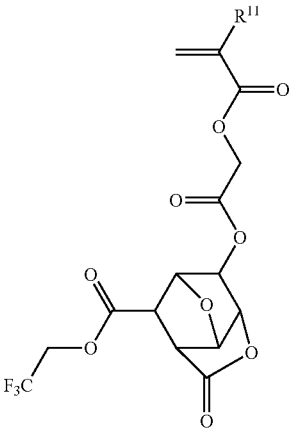

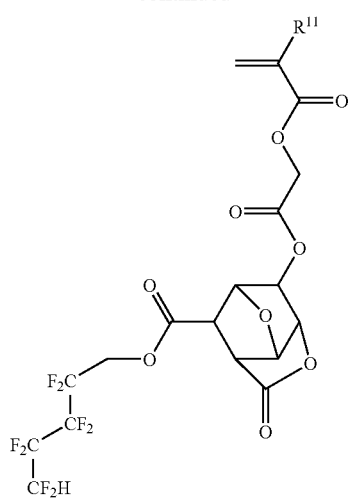

Herein $R^{11}$ is as defined above.

Of the monomers from which recurring units of formula (5L-1) are derived, those monomers wherein M'=1 are described in JP-A 2008-031298. Those monomers wherein M'=3 may be similarly synthesized aside from using chlorobutyric chloride instead of chloroacetyl chloride used as the reactant in the synthesis of the compounds wherein M'=1.

Illustrative examples of the recurring units of formula (14) are given below.

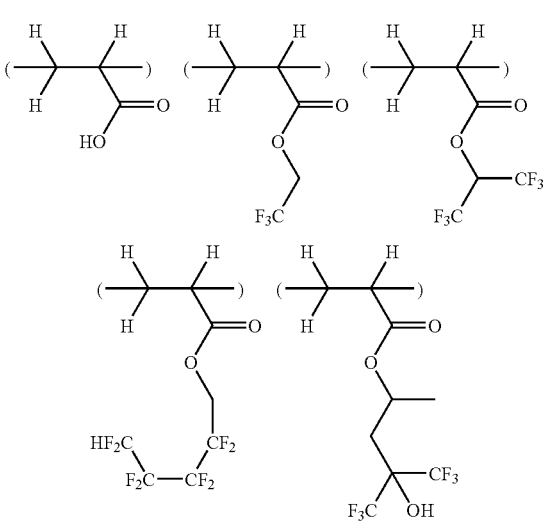
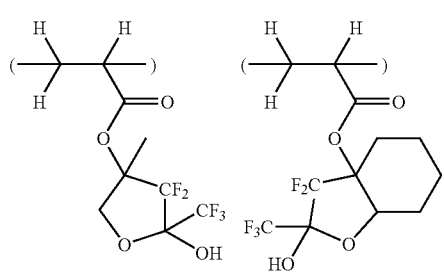
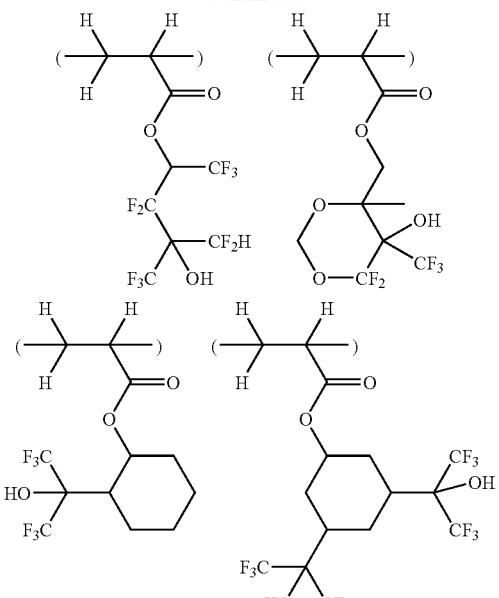
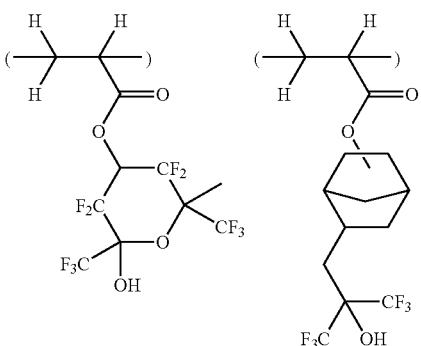
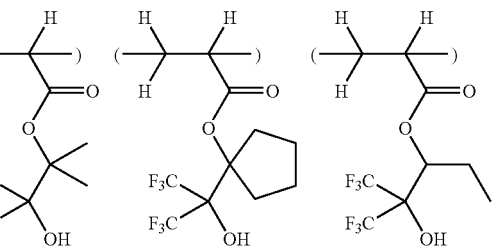

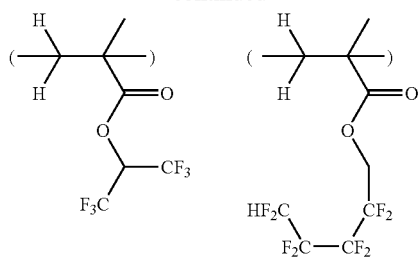
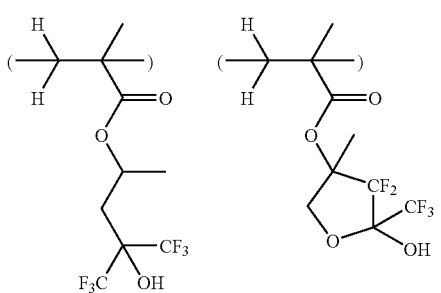
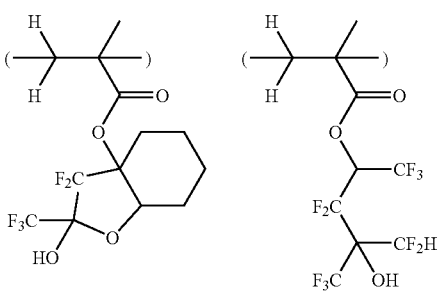
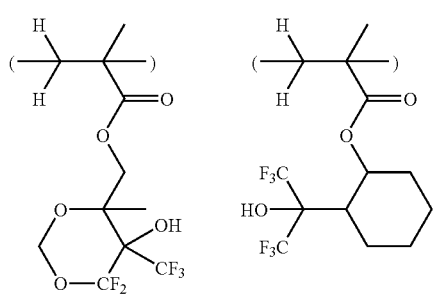
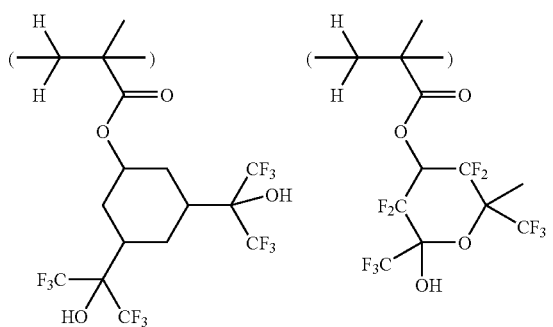
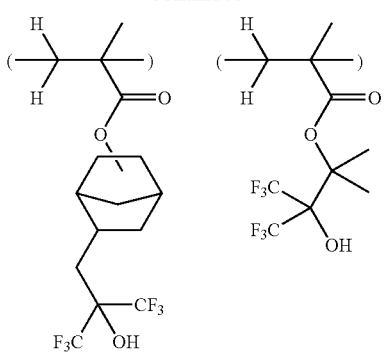
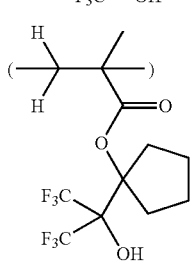
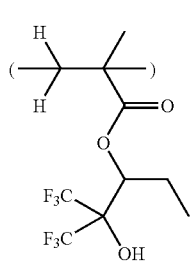
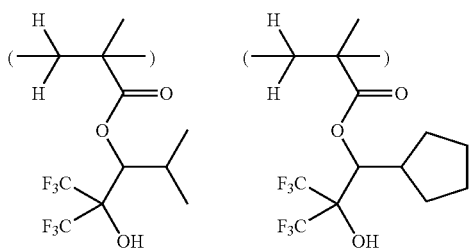
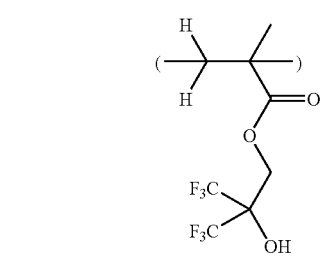
Illustrative examples of the recurring units of formula (15) are given below.
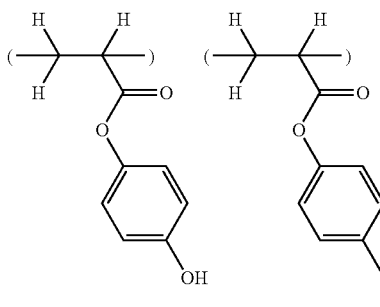

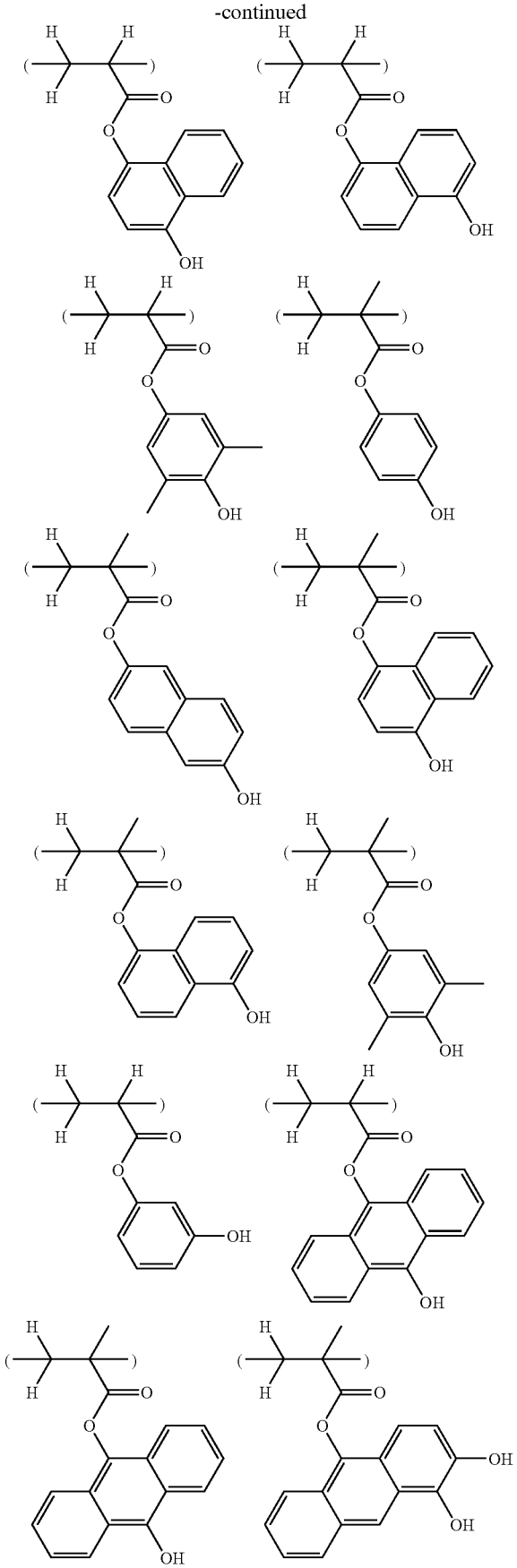
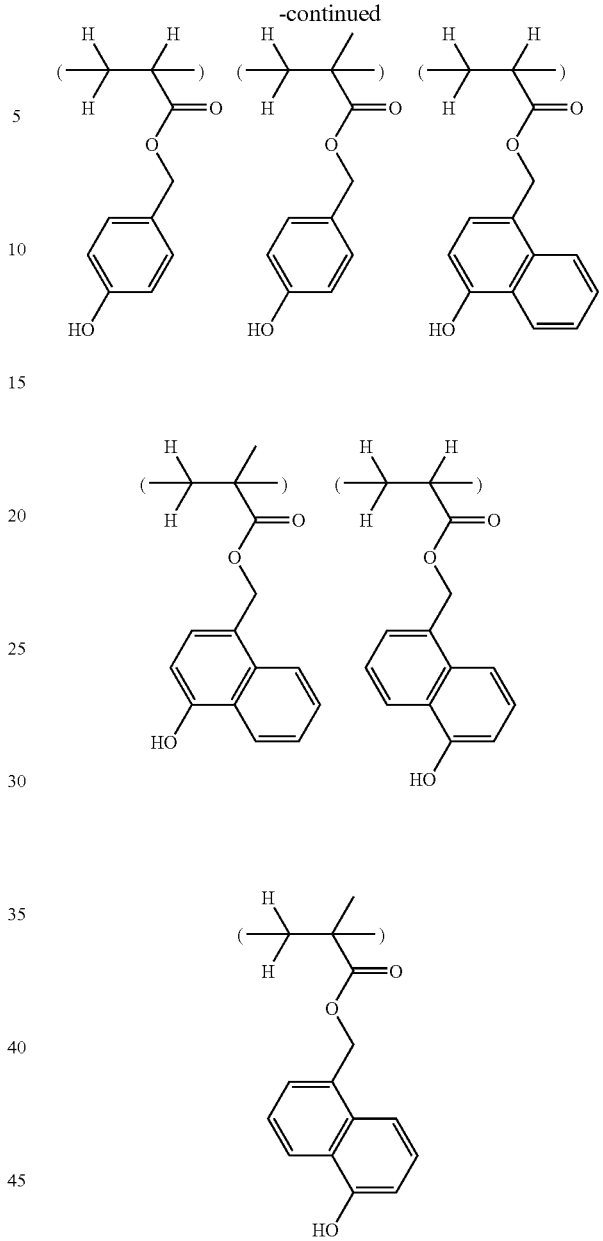

The polymer used herein may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo [6.2.1.1$^{3,6}$.0$^{2,7}$]dodecene derivatives, unsaturated acid anhydrides such as itaconic anhydride, and other monomers.

Although the polymers described above are preferably applicable to the ArF and EUV photolithography, they may also be applied to the KrF and EB lithography.

In an embodiment wherein the resist composition is applied to the KrF and EB lithography, the polymer as the base resin may desirably comprise recurring units of at least one type selected from the general formulae (21) to (25) and optionally, recurring units of at least one type selected from the general formulae (11) to (15).

(21) 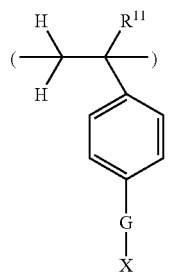

(22) 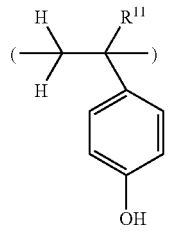

(23) 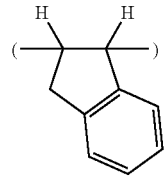

(24) 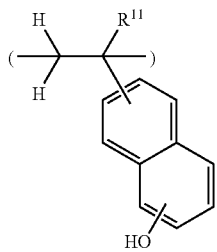

(25) 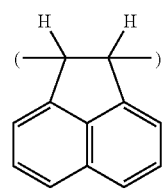

Herein $R^{11}$ and X are as defined above, and G is an oxygen atom or carbonyloxy group (—C(=O)O—).

Under the action of an acid, a polymer comprising recurring units of formula (21) is decomposed to generate a phenolic hydroxyl group and/or carboxylic acid whereby it becomes alkali soluble. The acid labile group X may be selected from a variety of such groups, for example, groups of formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, as illustrated previously.

Illustrative non-limiting examples of the recurring units of formula (21) are given below.

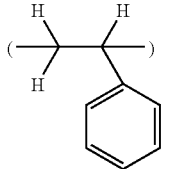

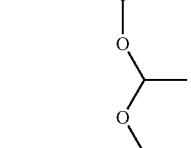

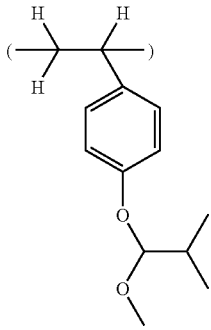

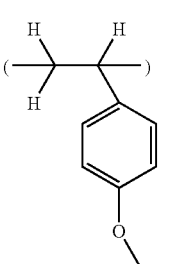

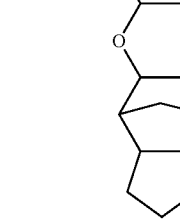

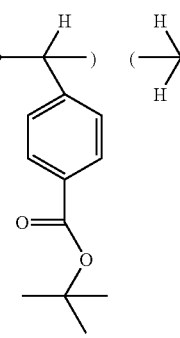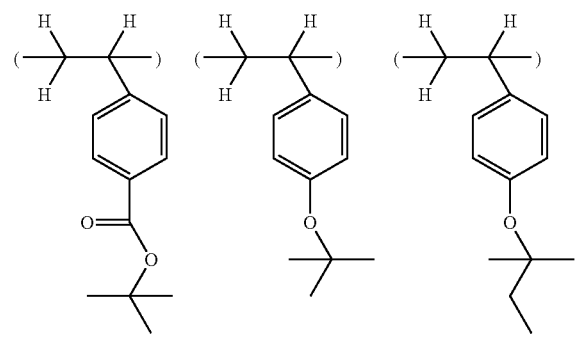

-continued

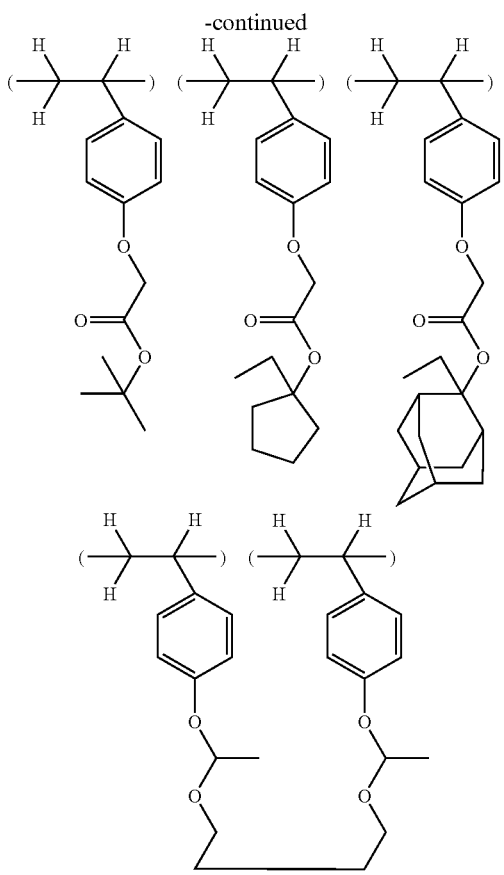

While hydroxyvinylnaphthalene of formula (24) may be substituted at arbitrary positions, typical substituted ones include 6-hydroxy-2-vinylnaphthalene and 4-hydroxy-1-vinylnaphthalene, with 6-hydroxy-2-vinylnaphthalene being preferred.

More preferred are those polymers comprising recurring units of any one type selected from formulae (21) to (25) and recurring units of any one type selected from formulae (11) to (15), especially recurring units of formula (11).

The polymer comprising recurring units of any one or more type selected from formulae (21) to (25) may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[6.2.1.1$^{3,6}$.0$^{2,7}$]dodecene derivatives, and norbornadiens, unsaturated acid anhydrides such as itaconic anhydride, styrene, acenaphthylene, vinylnaphthalene, and other monomers.

For convenience of description, the polymers comprising recurring units of formulae (11) to (15) and/or recurring units of formulae (21) to (25) are sometimes referred to as "inventive polymers."

The inventive polymers have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards.

In the polymer, the preferred proportion of respective recurring units derived from discrete monomers may fall, for example, in the range (mol %) shown below, but is not limited thereto. The inventive polymer may consist essentially of (I) from more than 0 mol % to 100 mol %, preferably 70 to 100 mol %, and more preferably 80 to 100 mol % of constituent units of one or more type having formulae (11) to (15) and/or (21) to (25); and optionally (II) from 0 mol % to less than 100 mol %, preferably 0 to 30 mol %, and more preferably 0 to 20 mol % of constituent units of one or more type derived from the additional monomer(s).

The inventive polymer used as the base resin in the chemically amplified positive resist composition should preferably comprise recurring units of formula (11) or (21). More preferably the polymer comprises recurring units of formulae (11), (12) and (13), or recurring units of formulae (21) and (22) and optionally recurring units of formula (23) or (25).

The polymer may be prepared through copolymerization reaction, for example, using the compound corresponding to formula (11) or (21) as a first monomer and one or more compounds having a polymerizable double bond as second and subsequent monomers. Various modes of copolymerization reaction may be used for the preparation of the polymer. The preferred modes are radical polymerization, anionic polymerization and coordination polymerization.

For radical polymerization, preferred reaction conditions include (a) a solvent selected from hydrocarbons such as benzene, ethers such as tetrahydrofuran, alcohols such as ethanol, and ketones such as methyl isobutyl ketone; (b) a polymerization initiator selected from azo compounds such as 2,2'-azobisisobutyronitrile and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range need not be excluded.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range need not be excluded.

Once a polymer is prepared by any of the above-described procedures, it may be modified by deprotecting some or all acid labile groups so that the polymer may be used in negative resist compositions as will be described later. Into the polymer in which acid labile groups have been deprotected, different acid labile groups may be introduced again. This indicates that acid labile groups different from the acid labile groups initially introduced during polymerization are introduced into the polymer.

For example, once a polymer is formed through radical polymerization of 4-ethoxyethoxystyrene with another polymerizable compound, the polymer may be tailored into a copolymer with hydroxystyrene by eliminating ethoxyethoxy groups from the polymer using acetic acid, pyridinium tosylate or the like. The tailored copolymer may be used as a base resin in negative resist compositions. By further reacting hydroxystyrene units of the copolymer with di-tert-butyl dicarbonate, tert-butyl chloroacetate, vinyl ether or the like, acid labile groups different from the acid labile groups (ethoxyethoxy) initially introduced during polymerization may be introduced into the copolymer.

In addition to the inventive polymer, another resin, specifically another polymer having a dissolution rate in an alkaline developer that increases under the action of an acid may be used. Exemplary other resins include, but are not limited to, (i) poly(meth)acrylic acid derivatives, (ii) norbornene derivative/maleic anhydride copolymers, (iii) hydrogenated products of ring-opening metathesis polymerization (ROMP) polymers, (iv) vinyl ether/maleic anhydride/(meth)acrylic acid derivative copolymers, and (v) polyhydroxystyrene derivatives.

Of these, the poly(meth)acrylic acid derivatives (i) are polymers comprising units of formulae (11) to (15) and other units in combination. The polyhydroxystyrene derivatives (v) include polymers comprising units of formulae (21) to (25) in combination and polymers comprising units of formulae (21) to (25) and units of formulae (11) to (15) in combination. In these polymers, a proportion of those units having acid labile groups, for example, monomer units of one or more types selected from among formulae (11) and (21) and a combination thereof is from more than 0 mole % to 80 mole %, preferably 1 to 50 mole %, and more preferably 10 to 40 mole %. In these polymers, a proportion of those units free of acid labile groups, for example, monomer units of one or more types selected from among formulae (12) to (15) and/or (22) to (25) and a combination thereof is from 0 mole % to less than 100 mole %, and when contained, from 20 mole % to less than 100 mole %, preferably 50 to 99 mole %, and more preferably 60 to 90 mole %.

The hydrogenated products of ROMP (iii) are synthesized by the method illustrated in Examples of JP-A 2003-66612. Illustrative examples of such hydrogenated polymers include those polymers having the recurring units shown below, but are not limited thereto.

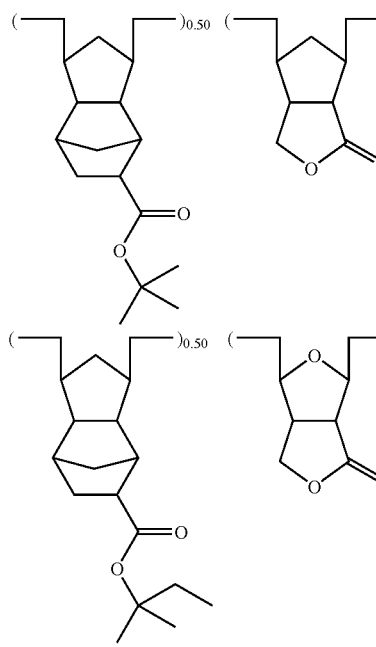

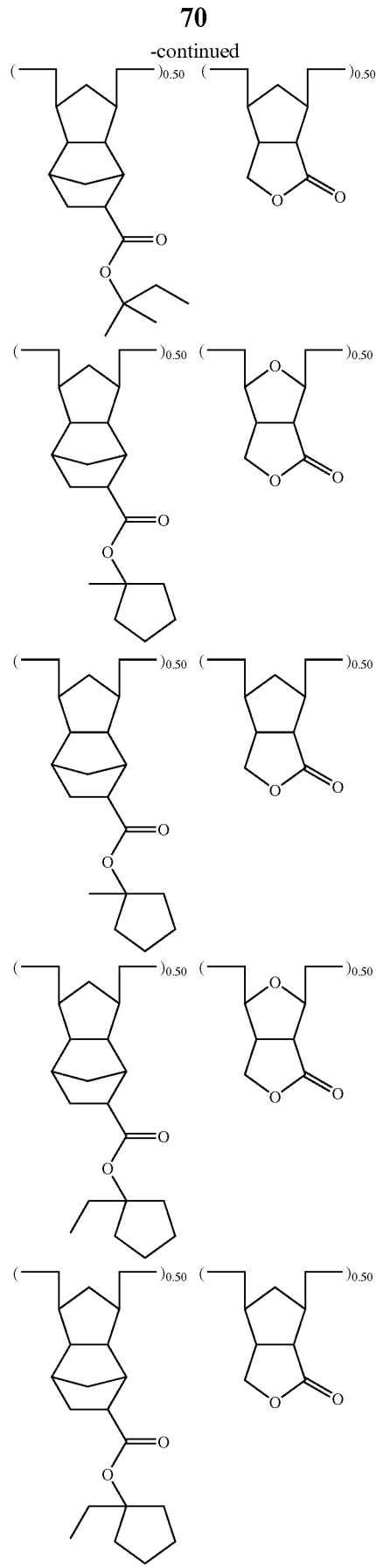

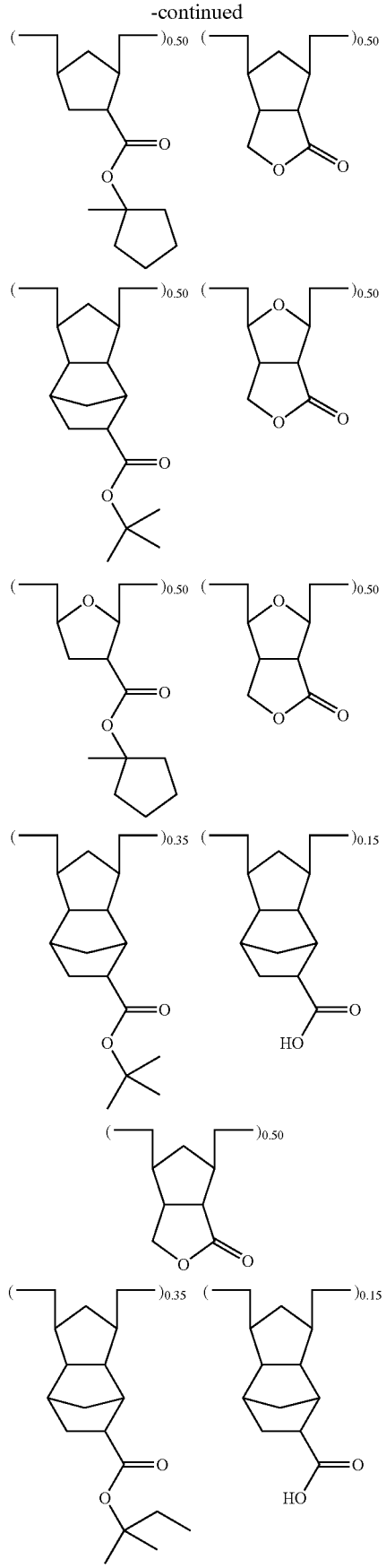
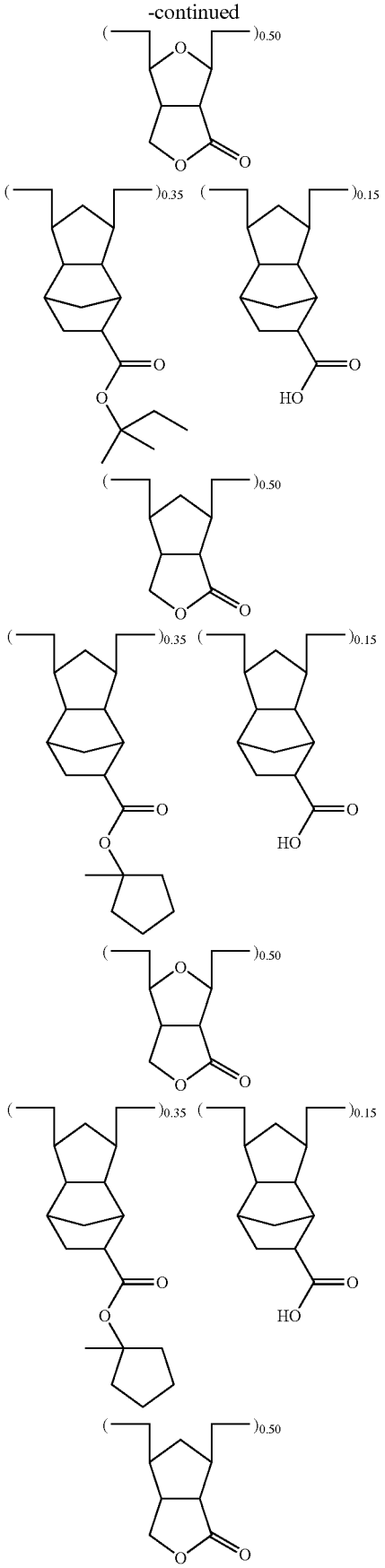

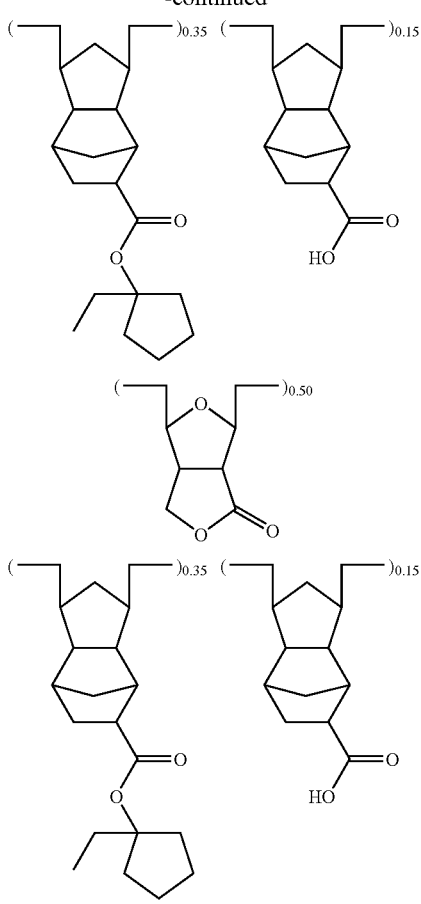

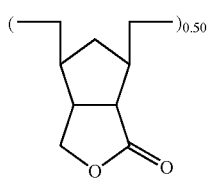

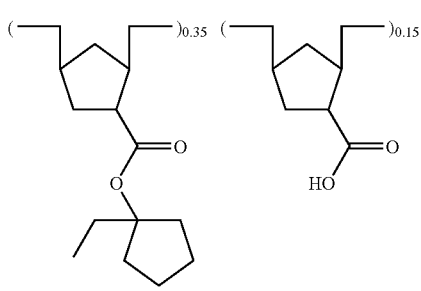

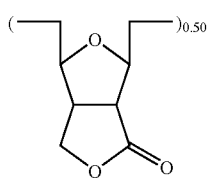

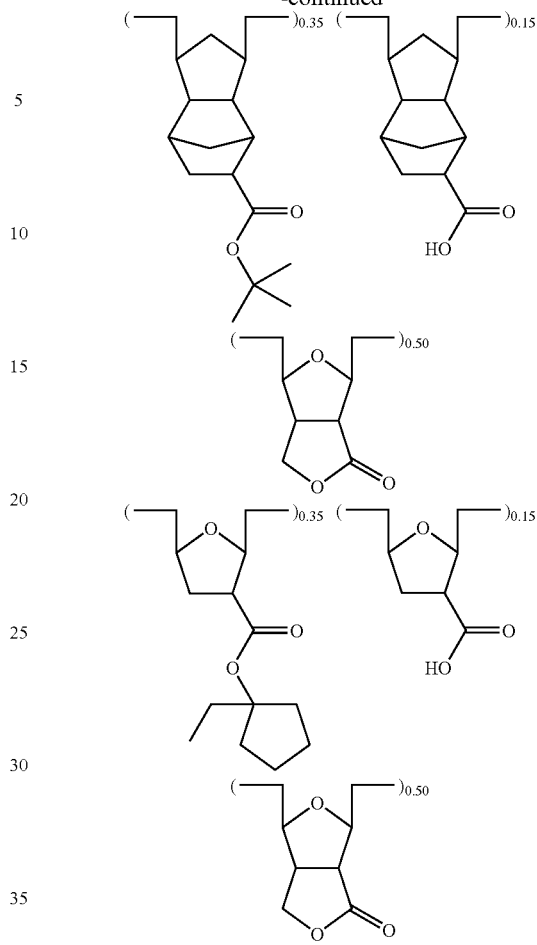

The inventive polymer containing the recurring units of formula (11) or (21) and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of polymers.

The polymer is not limited to one type and a mixture of two or more polymers may be added. The use of plural polymers allows for easy adjustment of resist properties.

Organic Solvent

The organic solvent (B) used herein may be any organic solvent in which the base resin, acid generator, and other components are soluble. Examples of the organic solvent are described in U.S. Pat. No. 7,537,880 (JP-A 2008-111103, paragraphs [0144] to [0145]).

Photoacid Generator

In combination with the inventive photoacid generator, an acid generator is used as component (C) if desired. Where a photoacid generator is added as the acid generator, it may be any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. The acid generators may be used alone or in admixture of two or more. Exemplary acid generators are described in U.S. Pat. No. 7,569,326 (JP-A 2008-133448).

When the acid generator as component (C) is used in addition to the inventive acid generator in the resist composition adapted for the ArF lithography, acid generators having the general formula (C)-1 are preferred.

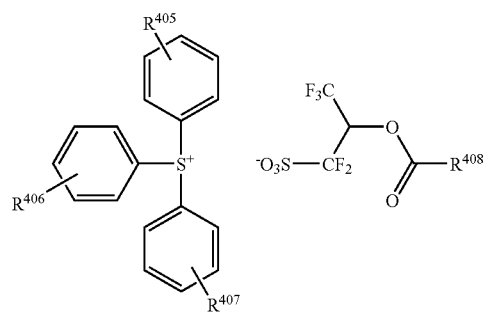
(C-1)

Herein $R^{405}$, $R^{406}$, and $R^{407}$ are each independently hydrogen or a straight, branched or cyclic, monovalent hydrocarbon group of 1 to 20 carbon atoms, typically an alkyl or alkoxy group, which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —NH—, —C(=O)—, —C(=O)O—, or —C(=O)NH—, or any hydrogen atom is replaced by a functional group such as —OH, —NH$_2$, —CHO, or —CO$_2$H. $R^{408}$ is a straight, branched or cyclic, monovalent hydrocarbon group of 7 to 30 carbon atoms which may contain a heteroatom, examples of which are exemplified below, but are not limited thereto.

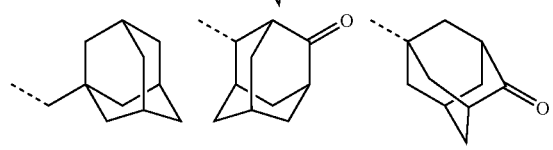

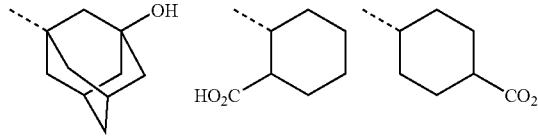

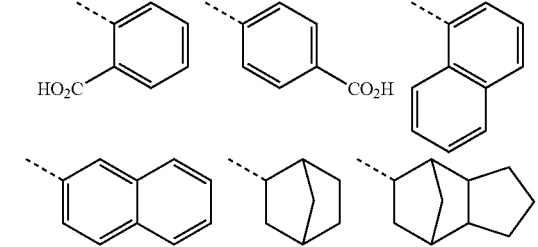

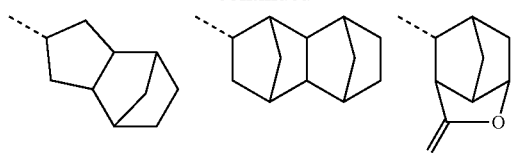

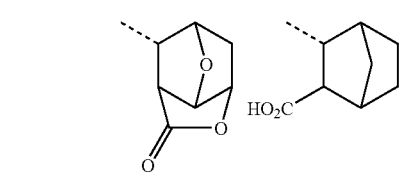

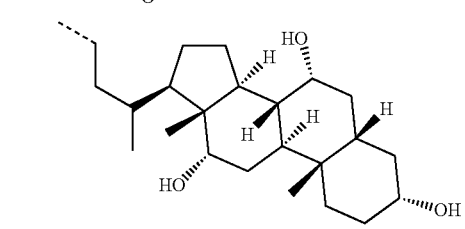

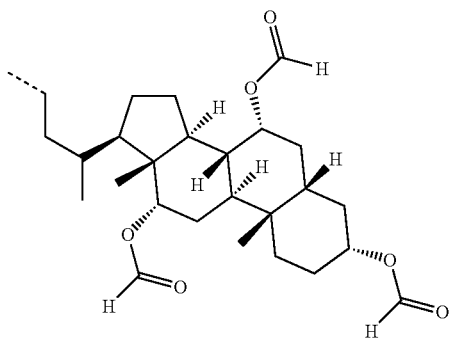

Illustrative examples of acid generators (C)-1 are shown below.

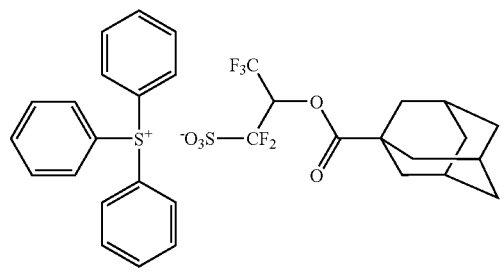

-continued
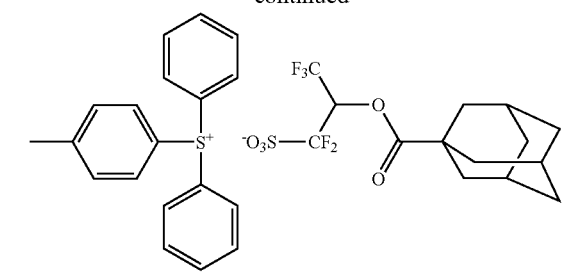
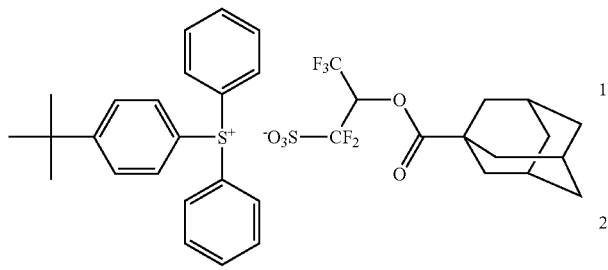
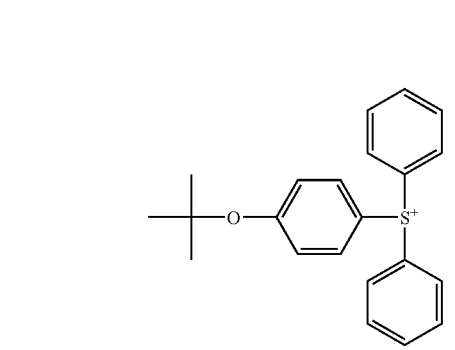
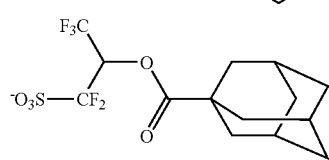
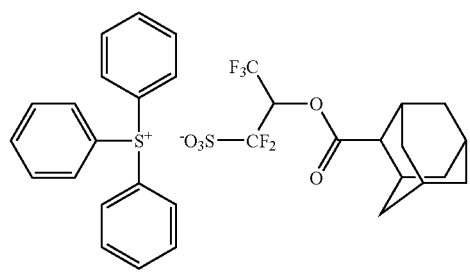
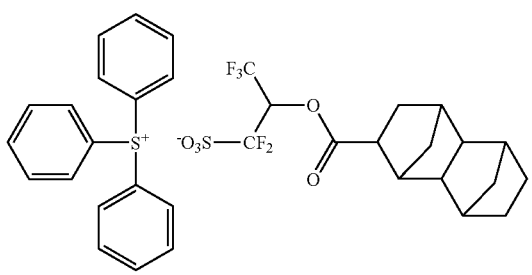
-continued
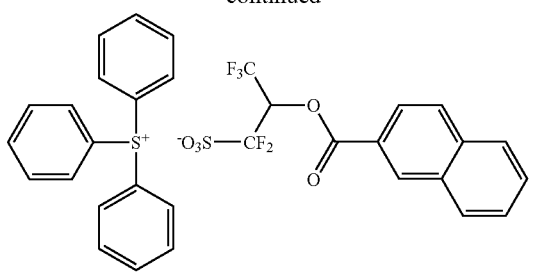
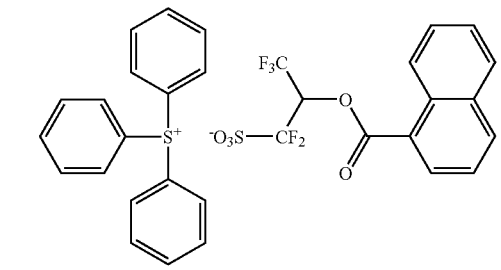
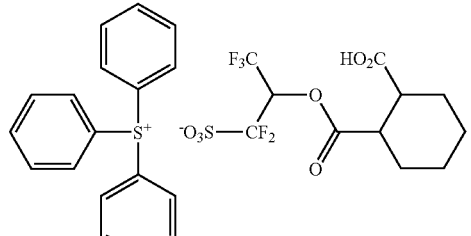
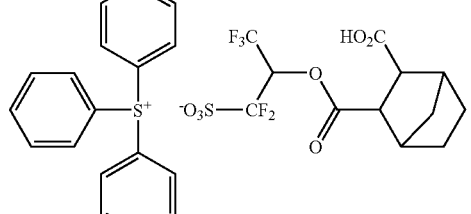
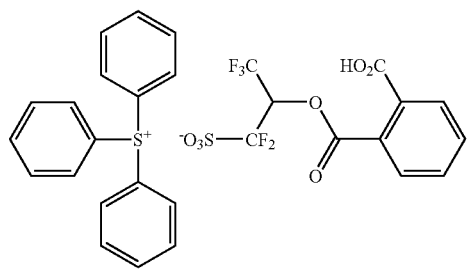
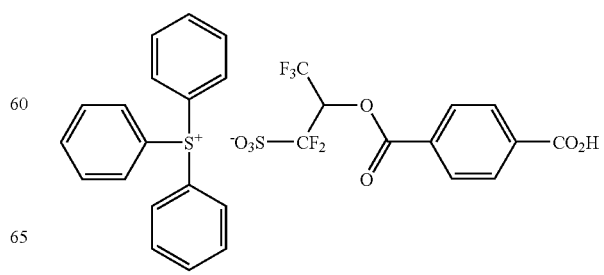

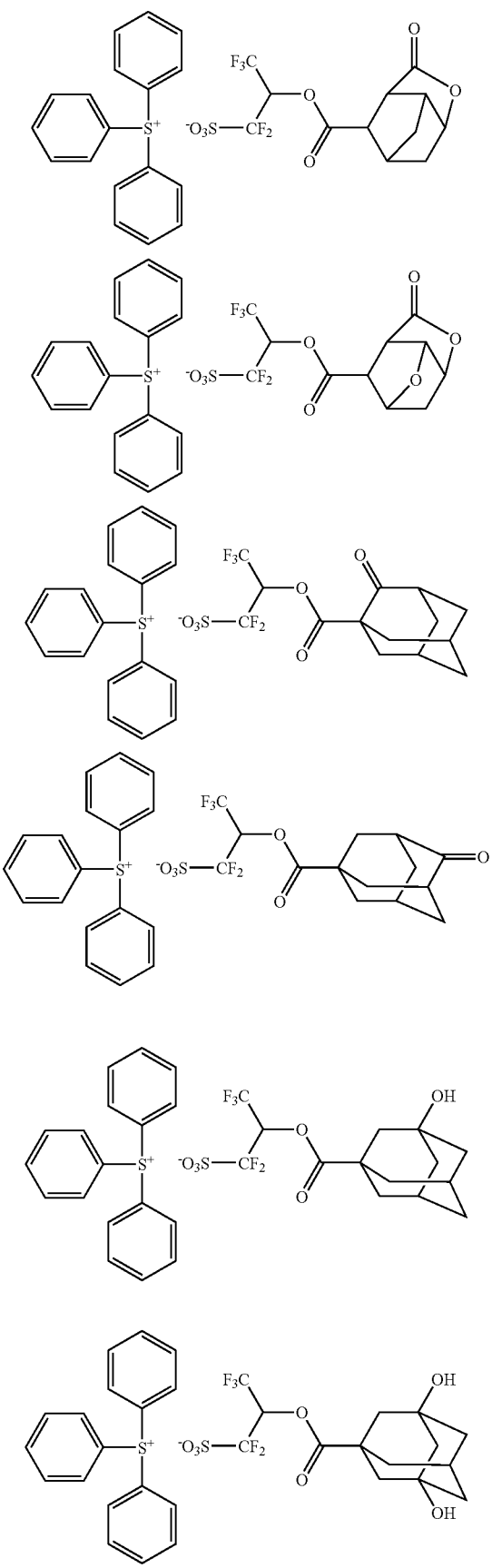

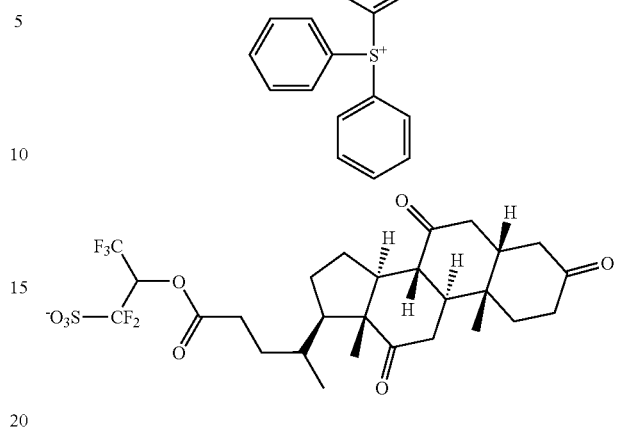

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid like the inventive photoacid generator or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the chemically amplified resist composition, the photoacid generator (C) may be added in any desired amount as long as the objects of the invention are not compromised. An appropriate amount of the photoacid generator (C), when added, is 0.1 to 10 parts, and more preferably 0.1 to 5 parts by weight per 100 parts by weight of the base resin in the composition. Too high a proportion of the photoacid generator (C) may give rise to problems of degraded resolution and foreign matter upon development and resist film peeling. The photoacid generators (C) may be used alone or in admixture of two or more. The transmittance of the resist film can be controlled by using a photoacid generator having a low transmittance at the exposure wavelength and adjusting the amount of the photoacid generator added.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Quencher

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of the quencher are described in U.S. Pat. No. 7,537,880 (JP-A 2008-111103, paragraphs [0146] to [0163]).

Tertiary amines are especially preferred as the quencher. Examples include tri-n-butylamine, tri-n-pentylamine, tri-n-hexylamine, tri-n-octylamine, N,N-dimethylaniline, triethanolamine, triisopropanolamine, tris(2-methoxymethoxyethyl)amine, tris(2-methoxyethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Further examples include 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]benzimidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]benzimidazole, 1-[2-[(2-methoxyethoxy)methoxy]ethyl]-2-phenylbenzimidazole, 1-[(2-[2-(2-methoxyethoxy)ethoxy]ethyl]pyrrolidine, 1-[2-[2-(2-methoxyethoxy)ethoxy]ethyl]piperidine, 4-[2-[2-(2-methoxyethoxy)ethoxy]ethyl]morpholine, 1-[2-[2-(2-methoxyethoxy)ethoxy]ethyl]imidazole, 1-[2-[2-(2-methoxyethoxy)ethoxy]ethyl]benzimidazole, 1-[2-[2-(2-methoxyethoxy)ethoxy]ethyl]-2-phenylbenzimidazole, 1-[2-[2-(2-butoxyethoxy)ethoxy]ethyl]pyrrolidine, 1-[2-[2-(2-butoxyethoxy)ethoxy]ethyl]piperidine, 4-[2-[2-(2-butoxyethoxy)ethoxy]ethyl]morpholine, 1-[2-[2-(2-butoxyethoxy)ethoxy]ethyl]imidazole, 1-[2-[2-(2-butoxyethoxy)ethoxy]ethyl]benzimidazole, 1-[2-[2-(2-butoxyethoxy)ethoxy]ethyl]-2-phenylbenzimidazole, 1-[2-[2-[2-(2-methoxyethoxy)ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-methoxyethoxy)ethoxy]ethoxy]ethyl]benzimidazole, 1-[2-[2-[2-(2-methoxyethoxy)ethoxy]ethoxy]

ethyl]-2-phenylbenzimidazole, 4-[2-{2-[2-(2-butoxyethoxy) ethoxy]ethoxy}ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazolyl) ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl) 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl)ethyl 2-[2-(2-methoxyethoxy)ethoxy]acetate, 2-(1-benzimidazolyl)ethyl 2-[2-(2-methoxyethoxy) ethoxy]acetate, 2-(2-phenyl-1-benzimidazolyl)ethyl 2-[2-(2-methoxyethoxy)ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl) cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl) ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2-phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-(2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, etc.

The quenchers may be used alone or in admixture of two or more. The quencher is preferably used in an amount of 0.001 to 5 parts, more preferably 0.01 to 3 parts by weight per 100 parts by weight of the total base resin (B). Less than 0.001 phr of the quencher may achieve no addition effect whereas more than 5 phr may lead to too low a sensitivity.

Surfactant

Optionally, the resist composition of the invention may further comprise (E) a surfactant which is commonly used for facilitating the coating operation. The surfactant may be added in conventional amounts so long as this does not compromise the objects of the invention.

Examples of the surfactant are described in U.S. Pat. No. 7,537,880 or JP-A 2008-111103, paragraphs [0165] to [0166].

Additional useful surfactants include partially fluorinated oxetane ring-opened polymers having the structural formula (surf-1).

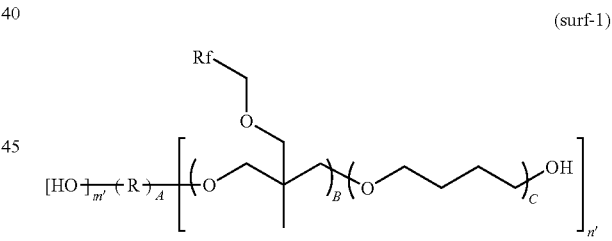

(surf-1)

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

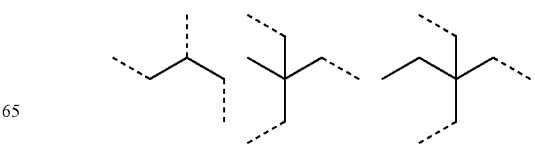

-continued

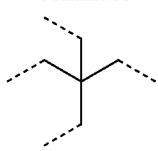

-continued

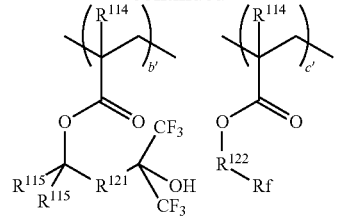

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430 (3M), Surflon S-381, Surfynol E1004, KH-20 and KH-30 (Asahi Glass Co., Ltd.), and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

In one embodiment wherein the immersion lithography using water is applied to the resist composition of the invention, particularly in the absence of a resist protective film, the resist composition may have added thereto another surfactant having a propensity to segregate at the resist surface after spin coating for achieving a function of minimizing water penetration or leaching. The preferred other surfactant is a polymeric surfactant which is insoluble in water, but soluble in alkaline developer, and especially which is water repellent and enhances water slippage. Suitable polymeric surfactants are shown below.

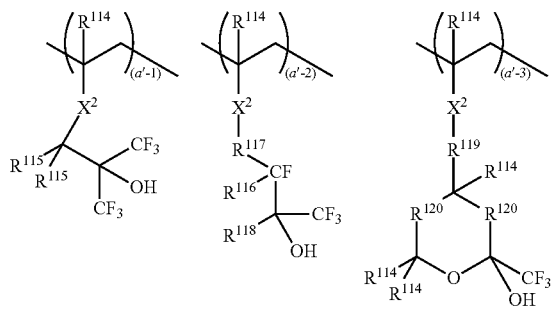

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_1$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range: $0 \leqq (a'\text{-}1) < 1$, $0 \leqq (a'\text{-}2) < 1$, $0 \leqq (a'\text{-}3) < 1$, $0 < (a'\text{-}1)+(a'\text{-}2)+(a'\text{-}3) < 1$, $0 \leqq b' < 1$, $0 \leqq c' < 1$, and $0 < (a'\text{-}1)+(a'\text{-}2)+(a'\text{-}3)+b'+c' \leqq 1$.

In the chemically amplified resist composition of the invention, the polymeric surfactant is preferably formulated in an amount of 0.001 to 20 parts, and more preferably 0.01 to 10 parts by weight, per 100 parts by weight of the base resin. Reference should also be made to JP-A 2007-297590.

A further embodiment is a chemically amplified negative working resist composition comprising the inventive polymer. When used in this embodiment, the inventive polymer should further contain recurring units having a substituent group capable of forming a crosslinked structure with an acid crosslinker. Examples of such recurring units include, but are not limited to, those units derived from acrylic acid, methacrylic acid, hydroxystyrene (which may be substituted at any positions), and hydroxyvinylnaphthalene (which may be substituted at any positions).

Besides the inventive polymer, any alkali-soluble resins may be added. Examples of the alkali-soluble resin include, but are not limited to, poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers.

The inventive polymer and the other alkali-soluble resin are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

Notably, the alkali-soluble resin is not limited to one type and a mixture of two or more resins may be added. The use of plural resins allows for easy adjustment of resist properties.

Crosslinker

Formulated in the negative resist composition is an acid crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethylbisphenol A, 1,4-bis[2-(2-hydroxypropyl)]benzene, N,N,N',N'-tetramethoxymethylurea, and hexamethoxymethylmelamine.

In the chemically amplified resist composition, an appropriate amount of the acid crosslinker (F) is, though not limited thereto, 1 to 20 parts, and especially 5 to 15 parts by weight per 100 parts by weight of the base resin. The crosslinkers may be used alone or in admixture of two or more.

While the resist composition of the invention typically comprises a polymer or base resin, acid generator, organic solvent and quencher as described above, there may be added optional other ingredients such as surfactants and crosslinkers, as well as dissolution inhibitors, acidic compounds, stabilizers, and dyes. Optional ingredients may be added in conventional amounts so long as this does not compromise the objects of the invention.

Process

In forming a pattern from the resist composition of the invention, any well-known lithography may be employed. For example, the composition is applied onto a substrate for integrated circuitry fabrication (e.g., Si, $SiO_2$, SiN, SiON, TiN, WSi, BPSG, SOG, organic antireflective coating, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 20 minutes, preferably 80 to 140° C. for 1 to 10 minutes, to form a resist film of 0.05 to 2.0 μm thick. A patterning mask having the desired pattern is then placed over the resist film, and the film exposed through the mask to high-energy radiation such as deep-UV, excimer laser or x-ray, or EB. Alternatively, pattern formation may be performed by drawing with EB directly (not through a mask). The exposure dose is 1 to 200 $mJ/cm^2$, and preferably 10 to 100 $mJ/cm^2$ for light exposure, and 0.1 to 20 $\mu C/cm^2$, and preferably 3 to 10 $\mu C/cm^2$ for EB exposure. Light exposure may be done by a conventional exposure process or in some cases, by an immersion process of providing liquid impregnation between the mask and the resist. In the case of immersion lithography, a protective coating which is insoluble in water may be used. The resist film is then post-exposure baked (PEB) on a hot plate at 60 to 150° C. for 1 to 20 minutes, and preferably at 80 to 140° C. for 1 to 10 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV having a wavelength of 250 to 190 nm, excimer laser, x-ray, or electron beam. The desired pattern may not be obtainable outside the upper and lower limits of the above range.

The water-insoluble protective coating which is used in the immersion lithography is to prevent the resist coating from being leached and to improve water slippage at the coating surface. It is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized areas of the resist coating. The protective coating of the second type is preferably of a material comprising a polymer having 1,1,1,3,3,3-hexafluoro-2-propanol residues (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective coating of the second type is formed.

Any desired step may be added to the pattern forming process. For example, after a photoresist coating is formed, a step of rinsing with pure water (post-soaking) may be introduced to extract the acid generator or the like from the coating surface or wash away particles. After exposure, a step of rinsing (post-soaking) may be introduced to remove any water remaining on the coating after exposure.

A still further embodiment of the invention pertains to a photomask blank comprising a chromium compound film and the chemically amplified resist composition applied thereon. A pattern forming process involves the steps of heat treating the photomask blank, subjecting the photomask blank to patternwise exposure to high-energy radiation through a photomask or patternwise exposure to high-energy beam, optionally heat treating, and developing the exposed photomask blank with a developer. More particularly, a photomask is produced by applying the resist composition onto a photomask blank, and processing the resist coating to form a resist pattern. When the resist composition is applied to a photomask blank having a coating of chromium base material as the outermost surface, better results are expectable from the pattern forming process because the resist pattern is little affected by substrate dependency. Also when a resist pattern is formed on a material containing silicon, oxygen and nitrogen, typically a molybdenum-silicon compound, a photomask can be produced in a reliable manner due to high resolution and aging stability of the resist composition.

Any well-known techniques may be employed in processing the photomask blank using the resist pattern as an etching mask. In general, the processing technique is dry etching with oxygen-containing chlorine gas when the photomask blank has a chromium base compound as the outermost surface. Dry etching with fluorine gas is used when the photomask blank has a transition metal-silicon compound as the outermost surface.

EXAMPLE

Examples and Comparative Examples are given below by way of illustration and not by way of limitation. Mw is weight average molecular weight and Mn is number average molecular weight, as measured by gel permeation chromatography (GPC) versus polystyrene standards.

Sulfonium salts within the scope of the invention were synthesized according to the following formulation.

Synthesis Example 1-1

Synthesis of Triphenylsulfonium Chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was allowed to mature for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was allowed to mature for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of triphenylsulfonium chloride. The compound in aqueous solution form was used in the subsequent reaction without further isolation.

Synthesis Example 1-2

Synthesis of 4-tert-butylphenyldiphenylsulfonium bromide

The target compound was obtained by following the procedure of Synthesis Example 1-1 aside from using 4-tert-butylbromobenzene instead of the chlorobenzene in Synthesis Example 1-1 and increasing the amount of water for extraction.

Synthesis Example 1-3

Synthesis of 4-tert-butoxyphenyldiphenylsulfonium chloride

The target compound was obtained by following the procedure of Synthesis Example 1-1 aside from using 4-tert-butoxychlorobenzene instead of the chlorobenzene in Synthesis Example 1-1, using dichloromethane containing 5 wt % of triethylamine as the solvent, and increasing the amount of water for extraction.

Synthesis Example 1-4

Synthesis of tris(4-methylphenyl)sulfonium chloride

The target compound was obtained by following the procedure of Synthesis Example 1-1 aside from using bis(4-methylphenyl) sulfoxide instead of the diphenyl sulfoxide and 4-chlorotoluene instead of the chlorobenzene in Synthesis Example 1-1, and increasing the amount of water for extraction.

Synthesis Example 1-5

Synthesis of tris(4-tert-butylphenyl)sulfonium bromide

The target compound was obtained by following the procedure of Synthesis Example 1-1 aside from using bis(4-tert-butylphenyl) sulfoxide instead of the diphenyl sulfoxide and 4-tert-butylbromobenzene instead of the chlorobenzene in Synthesis Example 1-1, and increasing the amount of water for extraction.

Synthesis Example 1-6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling. A mixture of 35 g of acetic anhydride and 95 g of conc. sulfuric acid was added dropwise thereto at a temperature below 30° C. The resulting solution was allowed to mature for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water, the washing step being repeated three times. The washed organic layer was concentrated in vacuum, obtaining a crude target product. The product was used in the subsequent reaction without further purification.

Synthesis Example 1-7

Synthesis of Dimethylphenylsulfonium Sulfate

At room temperature, 6.2 g (0.05 mole) of thioanisole and 6.9 g (0.055 mole) of dimethyl sulfate were stirred for 12 hours. 100 g of water and 50 ml of diethyl ether were added to the reaction solution. The aqueous layer was taken out, which was an aqueous solution of the target compound, dimethylphenylsulfonium sulfate.

Synthesis Example 1-8

Synthesis of phenacyltetrahydrothiophenium bromide

In 220 g of nitromethane were dissolved 88.2 g (0.44 mole) of phenacyl bromide and 39.1 g (0.44 mole) of tetrahydrothiophene. The solution was stirred for 4 hours at room temperature. 800 g of water and 400 g of diethyl ether were added to the reaction solution. The aqueous layer was taken out, which was an aqueous solution of the target compound, phenacyltetrahydrothiophenium bromide.

Synthesis Example 1-9

Synthesis of triphenylsulfonium 2-(adamantane-1-carbonyloxy)ethanesulfonate [PAG-1]

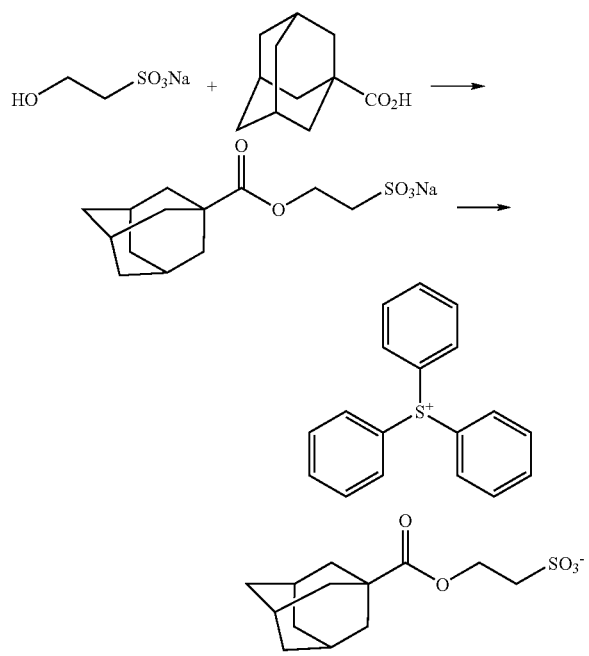

In 125 g of trifluoroacetic acid were dissolved 14.8 g (0.10 mole) of sodium isethionate and 18.0 g (0.10 mole) of 1-adamantanecarboxylic acid. To this solution, 32.0 g (0.15 mole) of trifluoroacetic anhydride was added dropwise, followed by stirring for 2 hours at room temperature. Then 430 g (0.15 mole) of an aqueous solution of triphenylsulfonium chloride prepared in Synthesis Example 1-1, 800 g of water, and 1,500 g of methylene chloride were added, followed by stirring for 1 hour at room temperature. At the end of stirring, the organic layer was taken out, aqueous sodium bicarbonate was added dropwise until the pH of the aqueous layer ceased to be acidic, and the organic layer was then taken out. The organic layer was washed with water and concentrated in vacuum. Methyl isobutyl ketone was added to the concentrate, which was concentrated in vacuum again while distilling off the residual water. Diisopropyl ether was added to the residue for recrystallization. The crystals were collected and dried, obtaining the target compound, triphenylsulfonium 2-(adamantane-1-carbonyloxy)ethanesulfonate. White crystals, 34.1 g, yield 62%. The compound, designated PAG-1, has the following structure.

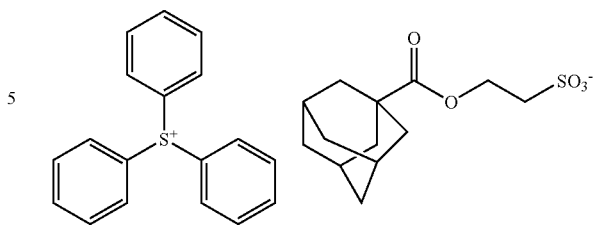

The compound was analyzed by spectroscopy. The nuclear magnetic resonance spectrum, $^1$H-NMR/DMSO-$d_6$ is shown in FIG. 1. Note that in $^1$H-NMR, traces of residual solvents (diisopropyl ether, methyl isobutyl ketone, water) were observed. The data of time-of-flight mass spectrometry (TOFMS) are also shown.

IR spectrum (KBr, cm$^{-1}$) 2906, 2852, 1714, 1477, 1446, 1324, 1268, 1241, 1218, 1205, 1184, 1103, 1089, 1072, 1033, 754, 686, 605, 536, 522, 493 cm$^{-1}$

TOFMS (MALDI)

Positive M$^+$ 263 (corresponding to $(C_6H_5)_3S^+$)

Negative M$^-$ 287 (corresponding to $(C_{10}H_{15}COO)C_2H_4SO_3^-$)

Analogous compounds were synthesized by following the procedure of Synthesis Example 1-9, aside from using one of the onium salts prepared in Synthesis Examples 1-2 to 1-8 instead of triphenylsulfonium chloride. The compounds correspond to PAG-1 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 1-10

Synthesis of triphenylsulfonium 2-[4-(10,13-dimethyl-3,7,12-trioxo-hexadecahydro-cyclopenta[a]phenanthren-17-yl)-pentanoyloxy]ethanesulfonate [PAG-2]

In 40 g of trifluoroacetic acid were dissolved 4.4 g (30 mmol) of sodium isethionate and 8.1 g (20 mmol) of dehydrocholic acid. To this solution, 6.3 g (30 mmol) of trifluoroacetic anhydride was added dropwise. After stirring for 2 hours at room temperature, 100 g of diisopropyl ether was added for recrystallization. The crystals were collected, washed with acetone, and dried, obtaining 11.8 g of a sodium salt. A 6.5-g portion of the sodium salt was combined with 36.1 g (15 mmol) of an aqueous solution of triphenylsulfonium chloride prepared in Synthesis Example 1-1 and 50 g of methylene chloride, followed by stirring for 12 hours at room temperature. At the end of stirring, the organic layer was taken out, washed with water, and concentrated in vacuum. Methyl isobutyl ketone was added to the concentrate, which was concentrated in vacuum again while distilling off the residual water. Diisopropyl ether was added to the residue for recrystallization. The crystals were collected and dried, obtaining the target compound, triphenylsulfonium 2-[4-(10,13-dimethyl-3,7,12-trioxo-hexadecahydro-cyclopenta[α]phenanthren-17-yl)-pentanoyloxy]-ethanesulfonate. White crystals, 6.2 g, yield 81% as calculated from the sodium salt. The compound, designated PAG-2, has the following structure.

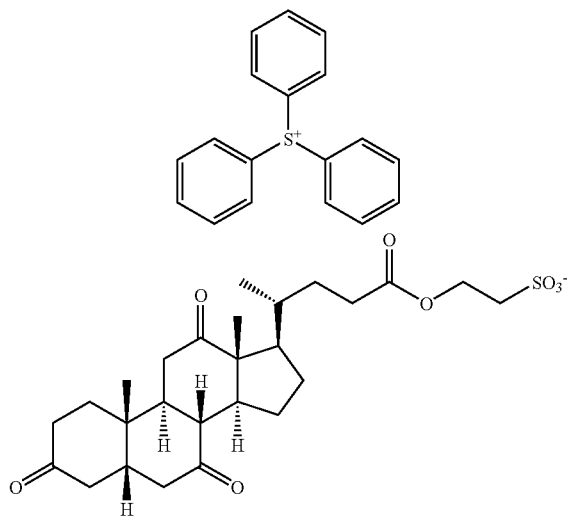

Figure 2:
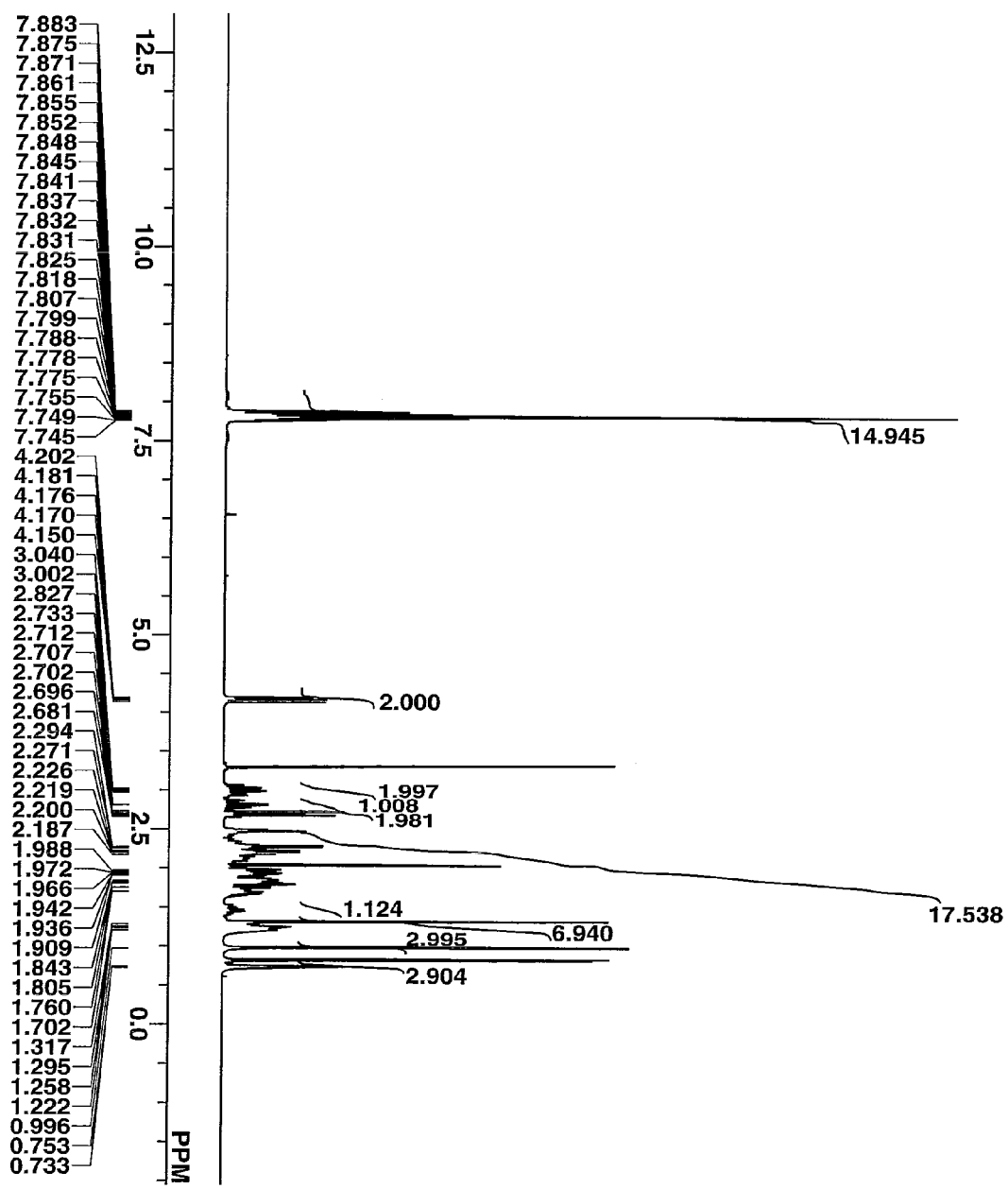
FIG. 2 is a diagram showing the $^1$H-NMR spectrum of PAG-2 in Synthesis Example 1-10.

The compound was analyzed by spectroscopy. The NMR spectrum ($^1$H-NMR/DMSO-$d_6$) is shown in FIG. 2. Note that in $^1$H-NMR, traces of residual solvents (methyl isobutyl ketone, water) were observed.

IR spectrum (KBr, cm$^{-1}$) 3444, 2962, 2871, 1706, 1475, 1446, 1386, 1203, 1035, 997, 752, 684, 524, 503 cm$^{-1}$

TOFMS (MALDI)

Positive M$^+$ 263 (corresponding to $(C_6H_5)_3S^+$)

Negative M$^-$ 509 (corresponding to $(C_{23}H_{33}O_3COO)$ $C_2H_4SO_3^-$)

Analogous compounds were synthesized by following the procedure of Synthesis Example 1-10, aside from using one of the onium salts prepared in Synthesis Examples 1-2 to 1-8 instead of triphenylsulfonium chloride. The compounds correspond to PAG-2 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 1-11

Synthesis of triphenylsulfonium 2-benzoyloxyethanesulfonate [PAG-3]

In 25 g of trifluoroacetic acid were dissolved 3.0 g (20 mmol) of sodium isethionate and 2.4 g (20 mmol) of benzoic acid. To this solution, 6.3 g (30 mmol) of trifluoroacetic anhydride was added dropwise, followed by stirring for 2 hours at room temperature. Then 90 g (30 mmol) of an aqueous solution of triphenylsulfonium chloride prepared in Synthesis Example 1-1 and 120 g of methylene chloride were added, followed by stirring for 30 minutes at room temperature. At the end of stirring, the organic layer was taken out, aqueous sodium bicarbonate was added dropwise until the pH of the aqueous layer ceased to be acidic, and the organic layer was then taken out. The organic layer was washed with water and concentrated in vacuum. Methyl isobutyl ketone was added to the concentrate, which was concentrated in vacuum again while distilling off the residual water. Diisopropyl ether was added to the residue. Subsequent decantation and drying gave the target compound, triphenylsulfonium 2-benzoyloxyethanesulfonate. Colorless oily matter, 3.0 g, yield 30%. The compound, designated PAG-3, has the following structure.

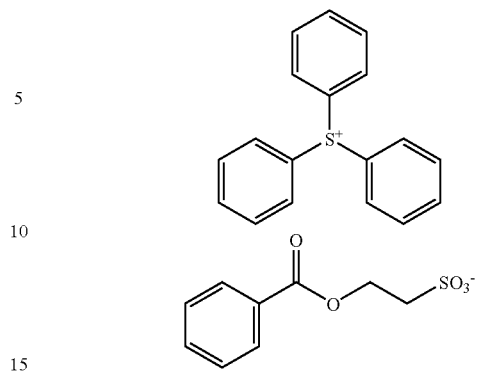

Figure 3:
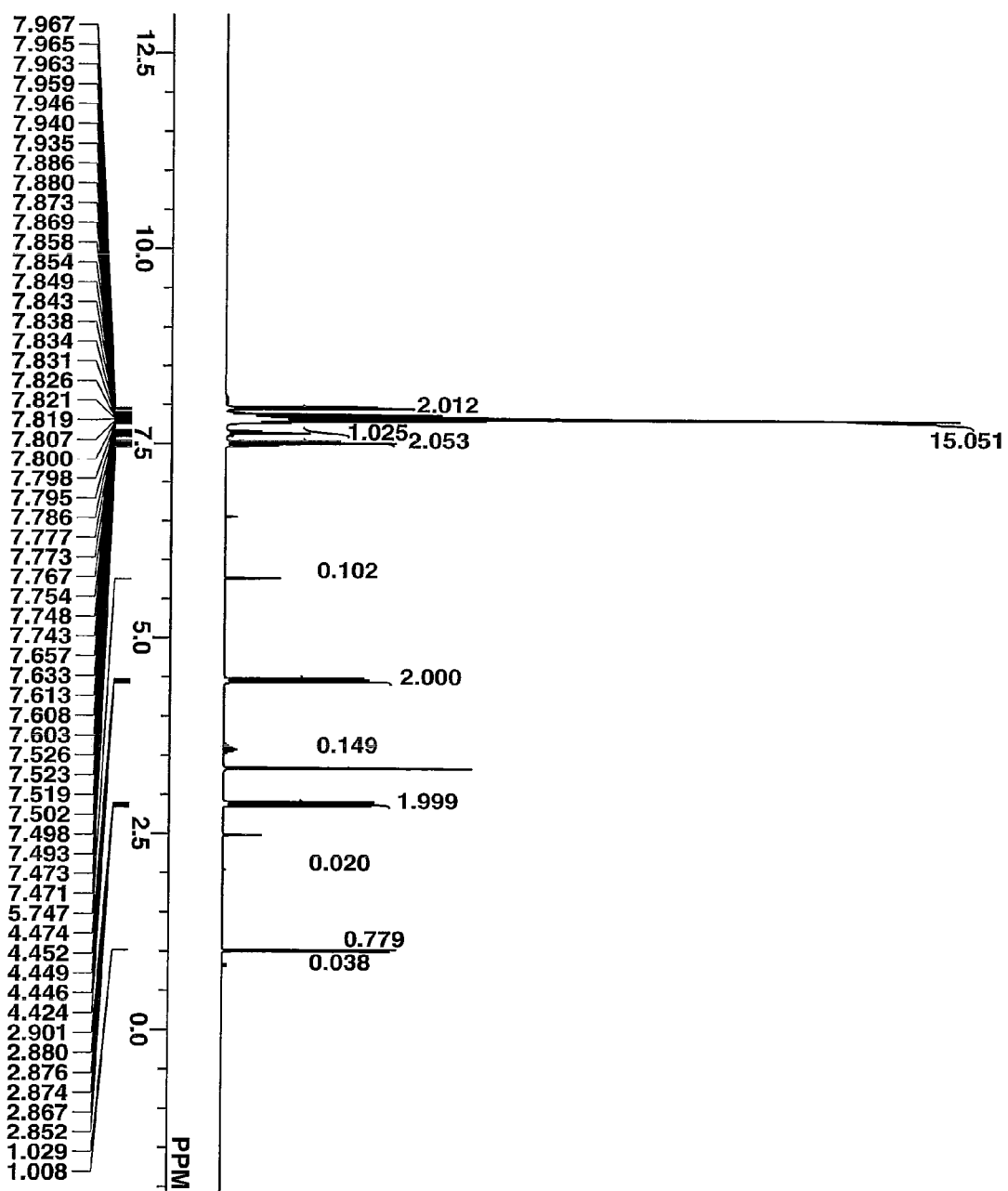
FIG. 3 is a diagram showing the $^1$H-NMR spectrum of PAG-3 in Synthesis Example 1-11.

The compound was analyzed by spectroscopy. The NMR spectrum (1H-NMR/DMSO-$d_6$) is shown in FIG. 3. Note that in $^1$H-NMR, traces of residual solvents (diisopropyl ether, methyl isobutyl ketone, methylene chloride, water) were observed.

IR spectrum (NaCl, cm$^{-1}$) 3461, 3087, 3060, 1716, 1652, 1600, 1477, 1448, 1315, 1278, 1249, 1201, 1184, 1118, 1068, 1035, 997, 752, 717, 684, 611 cm$^{-1}$

TOFMS (MALDI)

Positive M$^+$ 263 (corresponding to $(C_6H_5)_3S^+$)

Negative M$^-$ 229 (corresponding to $(C_6H_5COO)$ $C_2H_4SO_3^-$)

Analogous compounds were synthesized by following the procedure of Synthesis Example 1-11, aside from using one of the onium salts prepared in Synthesis Examples 1-2 to 1-8 instead of triphenylsulfonium chloride. The compounds correspond to PAG-3 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 1-12

Synthesis of triphenylsulfonium 2-cyclohexanecarbonyloxyethanesulfonate [PAG-4]

A mixture of 3.0 g (20 mmol) of sodium isethionate, 7.7 g (60 mmol) of cyclohexanecarboxylic acid, and 0.38 g (2 mmol) of tosylic acid was heated at 200° C. for 20 hours. Diethyl ether was added to the reaction solution, yielding 4.7 g of sodium 2-cyclohexanecarbonyloxyethanesulfonate. A 1.4-g portion of the sodium salt was combined with 23 g (10 mmol) of an aqueous solution of triphenylsulfonium chloride prepared in Synthesis Example 1-1 and 30 g of methylene chloride, followed by stirring for 12 hours at room temperature. At the end of stirring, the organic layer was taken out, washed with water, and concentrated in vacuum. Methyl isobutyl ketone was added to the concentrate, which was concentrated in vacuum again while distilling off the residual water. Diethyl ether was added to the residue, followed by decantation and purification by column chromatography. There was obtained the target compound, triphenylsulfonium 2-cyclohexanecarbonyloxyethanesulfonate. Colorless oily matter, 1.7 g, yield 66% as calculated from the sodium salt. The compound, designated PAG-4, has the following structure.

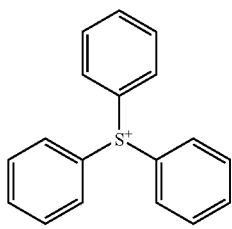

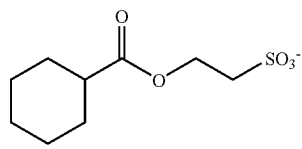

The compound was analyzed by spectroscopy.
TOFMS (MALDI)

Positive M⁺ 263 (corresponding to $(C_6H_5)_3S^+$)

Negative M⁻ 235 (corresponding to $(C_6H_{11}COO)C_2H_4SO_3^-$)

Analogous compounds were synthesized by following the procedure of Synthesis Example 1-12, aside from using one of the onium salts prepared in Synthesis Examples 1-2 to 1-8 instead of triphenylsulfonium chloride. The compounds correspond to PAG-4 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 1-13

Synthesis of triphenylsulfonium 2-hydroxyethanesulfonate [PAG intermediate 1]

A mixture of 2.9 g (6 mmol) of triphenylsulfonium 2-benzoyloxyethanesulfonate prepared in Synthesis Example 1-11, 56 mg (0.3 mmol) of 28 wt % sodium methoxide in methanol, and 15 g of methanol was stirred at room temperature for 12 hours. To the reaction solution, 30 mg of 35% aqueous hydrochloric acid was added to quench the reaction. The reaction solution was combined with methyl isobutyl ketone and concentrated in vacuum while distilling off the residual water. Diisopropyl ether was added to the residue for recrystallization. The crystals were collected and dried, obtaining the target compound, triphenylsulfonium 2-hydroxyethanesulfonate. White crystals, 2.1 g, yield 96%. The compound, designated PAG intermediate 1, has the following structure.

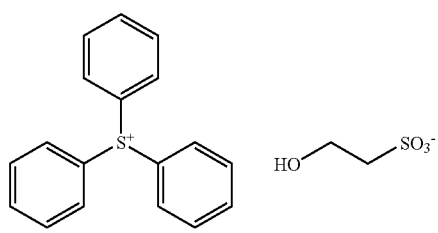

Figure 4:
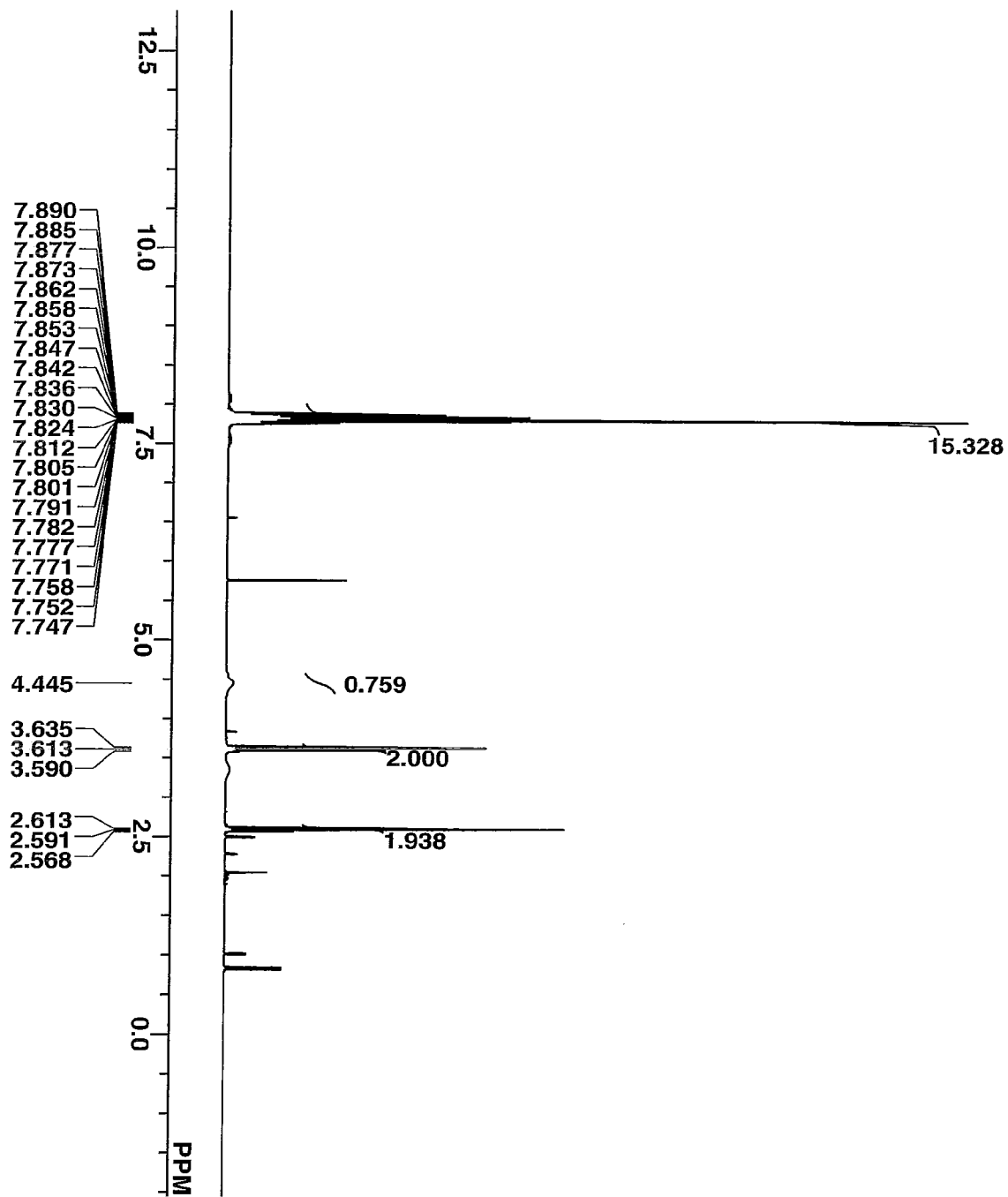
FIG. 4 is a diagram showing the $^1$H-NMR spectrum of PAG intermediate 1 in Synthesis Example 1-13.

The compound was analyzed by spectroscopy. The NMR spectrum ($^1$H-NMR/DMSO-$d_6$) is shown in FIG. 4. Note that in $^1$H-NMR, traces of residual solvents (diisopropyl ether, methyl isobutyl ketone, methylene chloride, water) were observed.
TOFMS (MALDI)

Positive M⁺ 263 (corresponding to $(C_6H_5)_3S^+$)

Negative M⁻ 125 (corresponding to $(HOC_2H_4SO_3^-)$)

Since the cation of triphenylsulfonium 2-benzoyloxyethanesulfonate is changeable as described above, the cation of PAG intermediate 1 is also changeable.

By acylating PAG intermediate 1 in an ordinary way, a variety of PAGs having formula (1) can be synthesized.

Synthesis Example 1-14

Synthesis of triphenylsulfonium 3-hydroxypropanesulfonate [PAG intermediate 2]

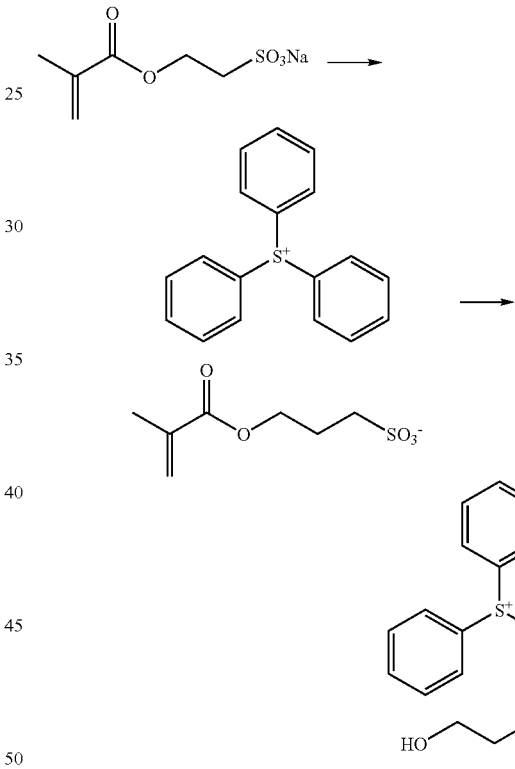

To 100 g of methylene chloride were added 2.5 g (10 mmol) of a potassium salt of 3-sulfopropyl methacrylate and 23 g (10 mmol) of an aqueous solution of triphenylsulfonium chloride prepared in Synthesis Example 1-1. The mixture was stirred at room temperature for 30 minutes. The organic layer was taken out and washed with water. It was combined with ethanol and concentrated in vacuum while azeotroping off the residual water. There was obtained 3.3 g of triphenylsulfonium 3-methacryloyloxypropanesulfonate. To 3.3 g of triphenylsulfonium 3-methacryloyloxypropanesulfonate were added 100 mg (0.6 mmol) of 28 wt % sodium methoxide in methanol and 15 g of methanol. The mixture was stirred at room temperature for 3 days. Then 70 mg of 35% aqueous hydrochloric acid was added to quench the reaction. The reaction solution was combined with methyl isobutyl ketone and concentrated in vacuum while distilling off the residual water. Diisopropyl ether was added to the residue for recrystallization. The crystals were collected and dried, obtaining the target compound, triphenylsulfonium 3-hydroxypropanesulfonate. White crystals, 2.1 g, yield 52%. The compound, designated PAG intermediate 2, has the following structure.

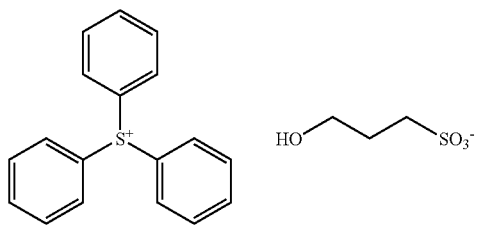

Figure 5:
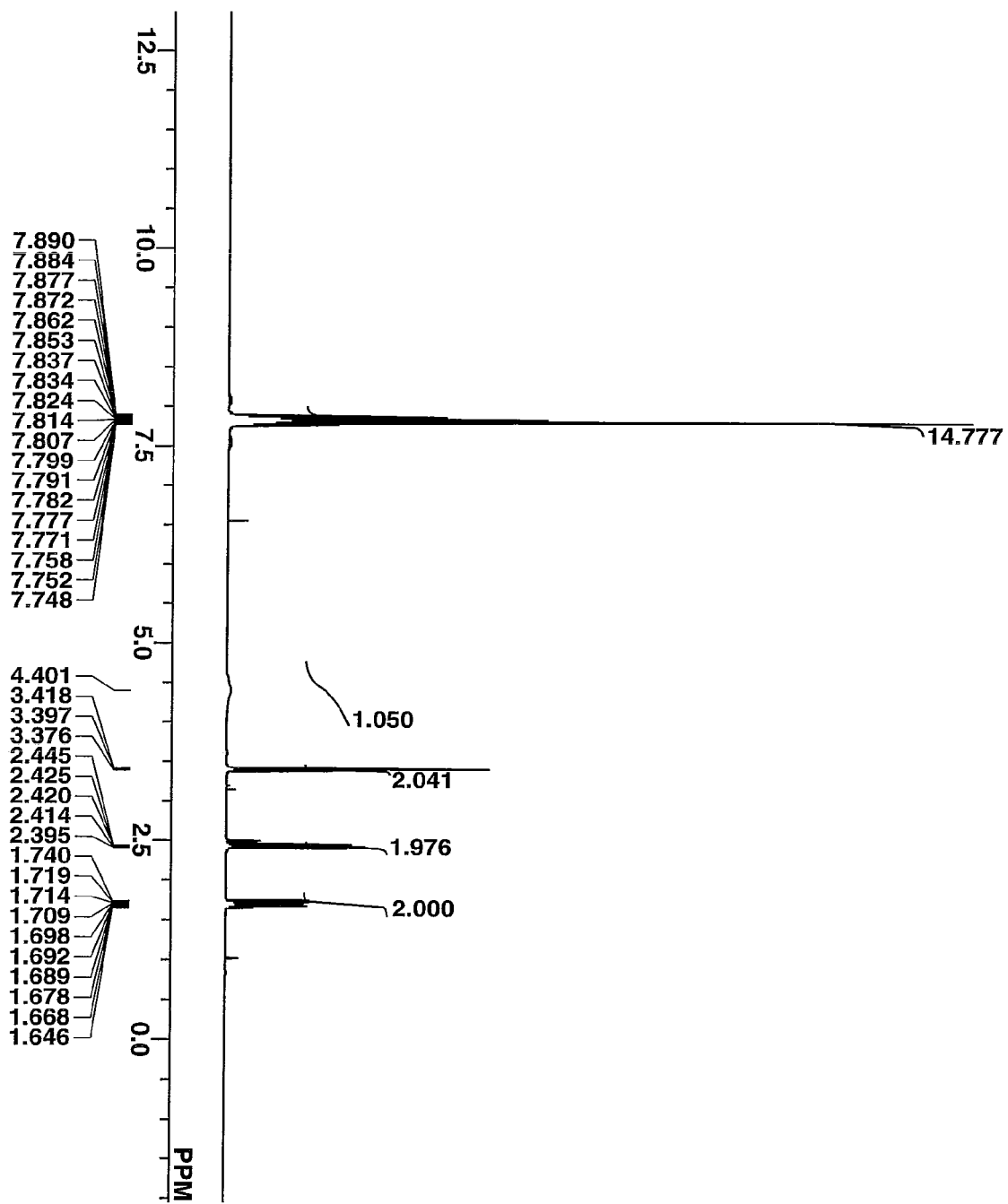
FIG. 5 is a diagram showing the $^1$H-NMR spectrum of PAG intermediate 2 in Synthesis Example 1-14.

The compound was analyzed by spectroscopy. The NMR spectrum ($^1$H-NMR/DMSO-$d_6$) is shown in FIG. 5. Note that in $^1$H-NMR, traces of residual solvents (diisopropyl ether, water) were observed.

IR spectrum (KBr, cm$^{-1}$) 3483, 3388, 3076, 3039, 3017, 2948, 2886, 1588, 1475, 1444, 1316, 1277, 1193, 1058, 997, 939, 926, 795, 757, 736, 685, 617, 531, 505 cm$^{-1}$

TOFMS (MALDI)

Positive M$^+$ 263 (corresponding to $(C_6H_5)_3S^+$)

Negative M$^-$ 139 (corresponding to $(HOC_3H_6SO_3^-)$)

Analogous compounds were synthesized by following the procedure of Synthesis Example 1-14, aside from using the onium salts prepared in Synthesis Examples 1-2 to 1-8 instead of triphenylsulfonium chloride in the step of cation exchange from the potassium salt of 3-sulfopropyl methacrylate. The compounds correspond to PAG intermediate 2 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

By acylating PAG intermediate 2 in an ordinary way, a variety of PAGs having formula (1) can be synthesized.

Synthesis Example 1-15

Synthesis of triphenylsulfonium 3-(adamantane-1-carbonyloxy)propanesulfonate [PAG-5]

To a mixture of 2.1 g (5 mmol) of the triphenylsulfonium 3-hydroxypropanesulfonate prepared in Synthesis Example 1-14, 0.6 g (6 mmol) of triethylamine and 10 g of methylene chloride, 2.9 g (6 mmol) of 1-adamantanecarbonyl chloride was added dropwise, followed by stirring for 3 hours at room temperature. Then 5.5 g of 5% aqueous hydrochloric acid was added to quench the reaction. The organic layer was separated from the reaction solution, washed with water, and concentrated in vacuum. Methyl isobutyl ketone was added to the concentrate, which was concentrated in vacuum again while azeotroping off the residual water. Diisopropyl ether was added to the residue, followed by decantation and drying. There was obtained the target compound, triphenylsulfonium 3-(adamantane-1-carbonyloxy)propanesulfonate. Colorless oily matter, 2.3 g, yield 79%. The compound, designated PAG-5, has the following structure.

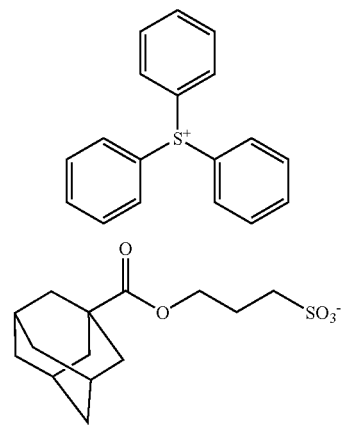

Figure 6:
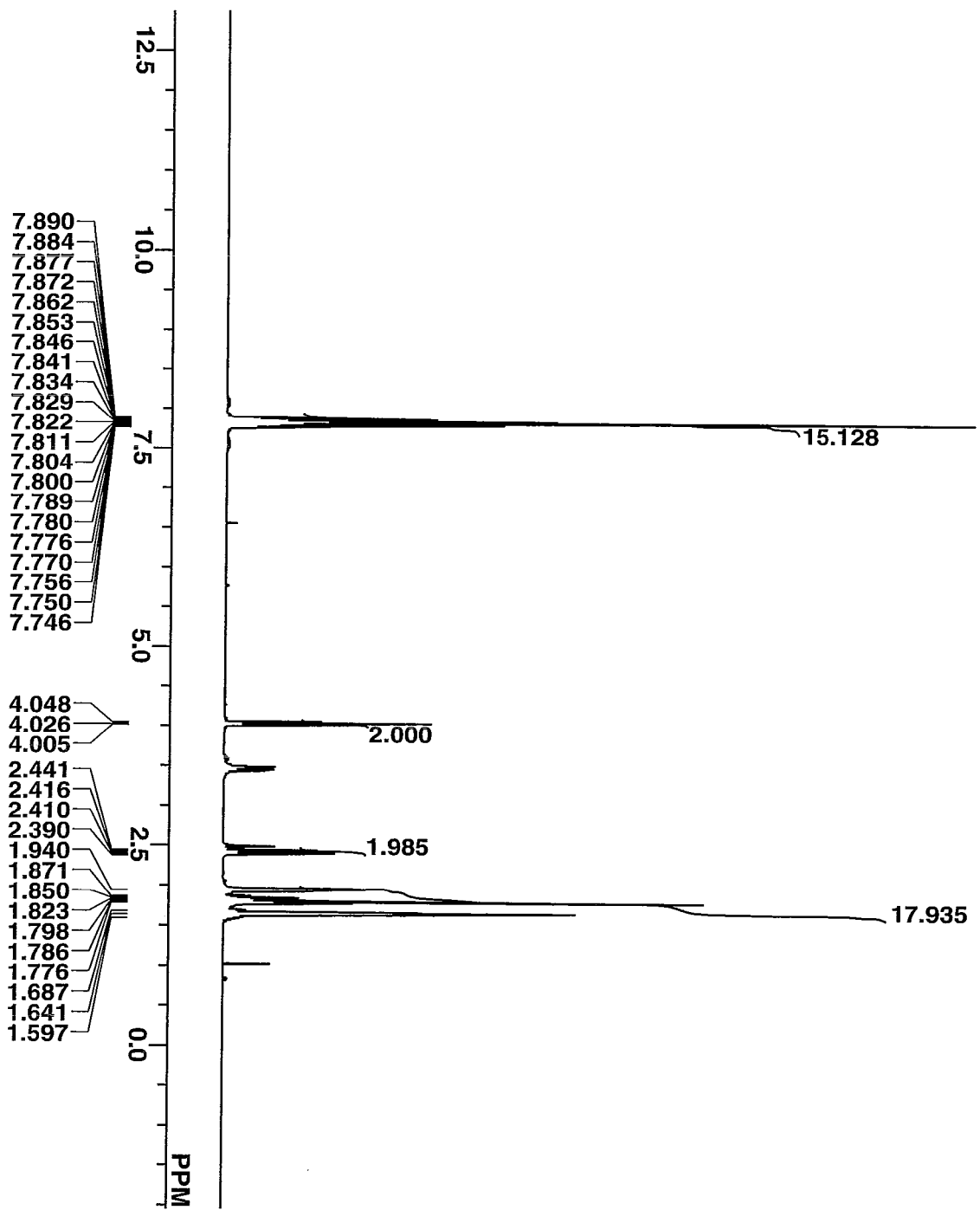
FIG. 6 is a diagram showing the $^1$H-NMR spectrum of PAG-5 in Synthesis Example 1-15.

The compound was analyzed by spectroscopy. The NMR spectrum ($^1$H-NMR/DMSO-$d_6$) is shown in FIG. 6. Note that in $^1$H-NMR, traces of residual solvents (diisopropyl ether, water) were observed.

IR spectrum (KBr, cm$^{-1}$) 3483, 3389, 3077, 3039, 2905, 2849, 1723, 1588, 1475, 1444, 1344, 1325, 1317, 1270, 1241, 1187, 1104, 1078, 1050, 1023, 997, 939, 757, 685, 610, 530, 505, 433 cm$^{-1}$

TOFMS (MALDI)

Positive M$^+$ 263 (corresponding to $(C_6H_5)_3S^+$)

Negative M$^-$ 301 (corresponding to $(C_{10}H_{15}COO)C_3H_6SO_3^-$)

Since the cation of PAG intermediate 2 is changeable as described above, the cation of PAG-5 is also changeable.

Synthesis Example 1-16

Synthesis of bis(4-tert-butylphenyl)iodonium 2-(adamantane-1-carbonyloxy)ethanesulfonate [PAG-6]

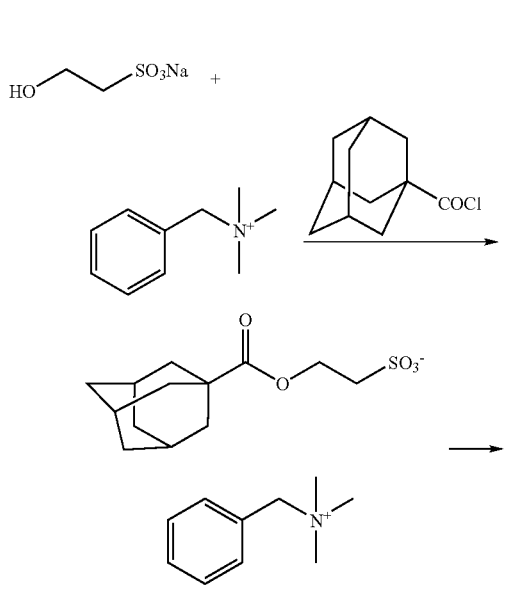

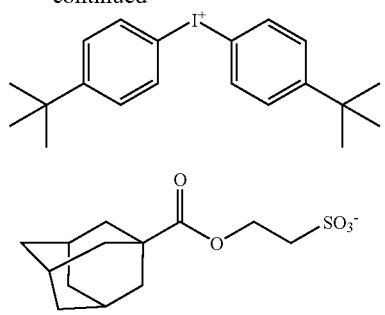

In water, 5.1 g (0.035 mole) of sodium isethionate and 6.4 g (0.053 mole) of benzyltrimethylammonium chloride were mixed and dissolved. The solution was concentrated by removing water in vacuum. The concentrate was dispersed in 55 g of acetonitrile. To the dispersion, 5.2 g (0.052 mole) of triethylamine and 0.42 g (0.0035 mole) of 4-(dimethylamino) pyridine were added, and under ice cooling, 20.6 g (0.052 mole) of 50% adamantane-1-carbonyl chloride in dichloromethane was then added dropwise. The reaction mixture was stirred at room temperature over night. Water was added to quench the reaction, from which acetonitrile was distilled off in vacuum. An amount (0.0088 mole) of bis(4-tert-butylphenyl)iodonium hydrogensulfate prepared in Synthesis Example 1-6 and 50 g of methyl isobutyl ketone were added to the residue, followed by stirring at room temperature for 1 hour. The organic layer was taken out, washed with water, and concentrated in vacuum. Diisopropyl ether was added to the concentrate for recrystallization. The crystals were collected and dried, obtaining the target compound, bis(4-tert-butylphenyl)iodonium 2-(adamantane-1-carbonyloxy)ethanesulfonate. White crystals, 5.7 g, yield 95%. The compound, designated PAG-6, has the following structure.

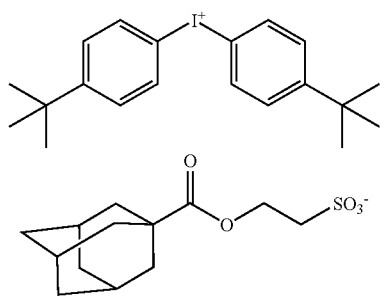

Figure 7:
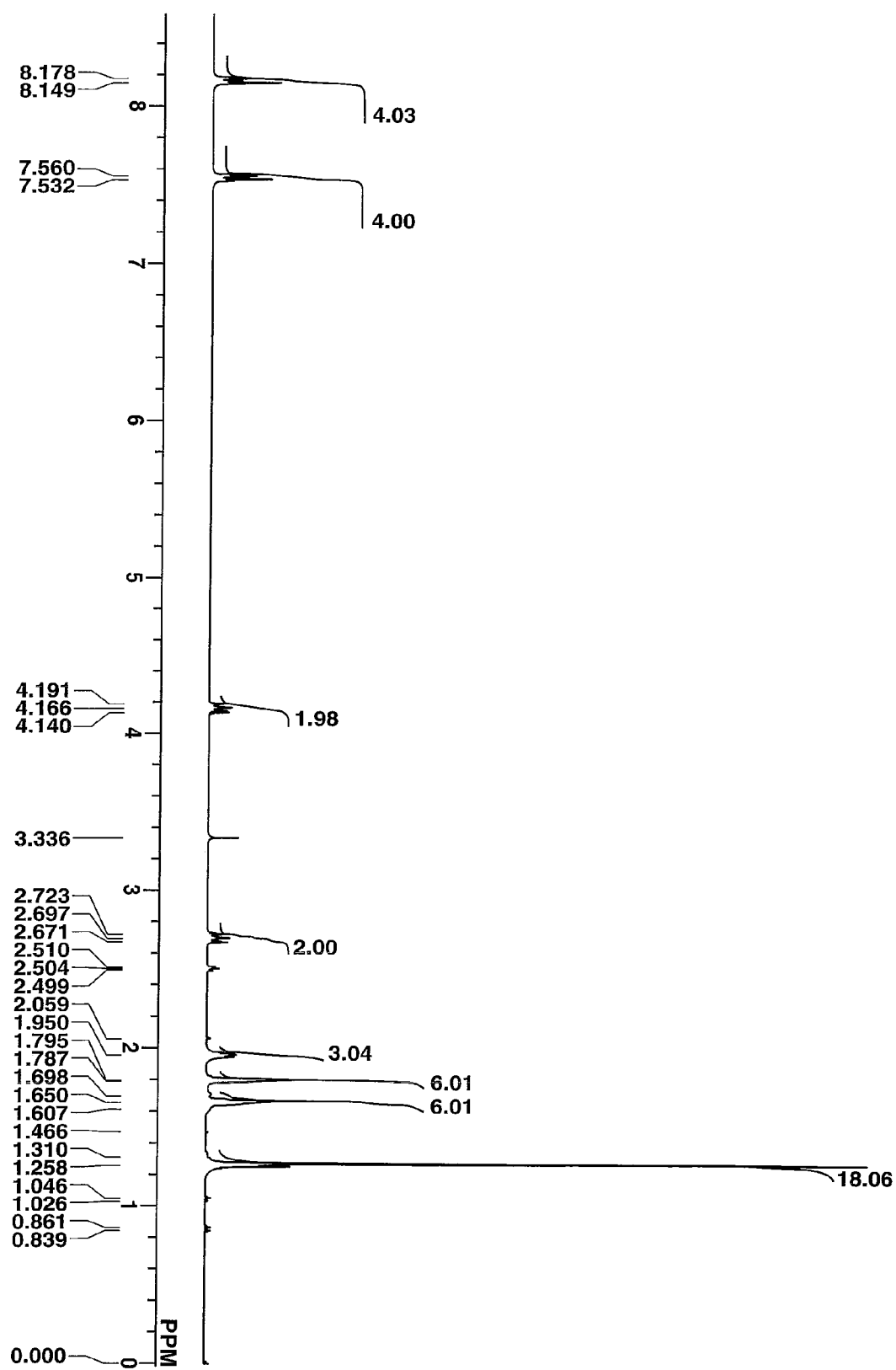
FIG. 7 is a diagram showing the $^1$H-NMR spectrum of PAG-6 in Synthesis Example 1-16.

The compound was analyzed by spectroscopy. The NMR spectrum ($^1$H-NMR/DMSO-$d_6$) is shown in FIG. 7. Note that in $^1$H-NMR, traces of residual solvents (diisopropyl ether, methyl isobutyl ketone, water) were observed.

IR spectrum (KBr, cm$^{-1}$) 2960, 2932, 2904, 2850, 1725, 1490, 1453, 1397, 1267, 1231, 1223, 1183, 1168, 1106, 1090, 1036, 993, 815, 731, 607 cm$^{-1}$

TOFMS (MALDI)

Positive M$^+$ 393 (corresponding to $(C_{20}H_{26})_2I^+$)

Negative M$^-$ 287 (corresponding to $(C_{10}H_{15}COO)C_2H_4SO_3^-$)

Since the cation of PAG intermediate 2 is changeable as described above, the cation of PAG-5 is also changeable.

Polymers were synthesized according to the following formulation.

Synthesis Example 2-1

Synthesis of Polymer 1

In a nitrogen blanket, 114 g of acetoxystyrene, 11.7 g of indene, 38.5 g of ethoxyethoxystyrene, and 8.2 g of 2,2'-azobisisobutyronitrile were dissolved in 550 g of toluene to form a solution. In the nitrogen blanket, the solution was stirred at 50° C. for 50 hours and then allowed to cool down to room temperature. To the polymerization solution were added 475 g of methanol and 75 g of water. The solution separated into two layers, whereupon the lower layer was taken out and concentrated in vacuum. The concentrate was directly used in the subsequent step, hydrolysis.

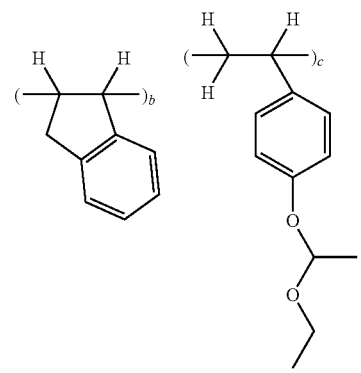

(Polymer 1)

(a = 0.70, b = 0.10, c = 0.20)

Synthesis Examples 2-2 to 2-11

Synthesis of Polymers 2 to 11

Polymers 2 to 11 were prepared by the same procedure as Synthesis Example 2-1 except that the type and proportion of monomers were changed.

Synthesis Example 2-12

Synthesis of Polymer 12

To the Polymer 1-containing concentrate prepared in Synthesis Example 2-1 were added 290 g of tetrahydrofuran, 260 g of methanol, 90 g of triethylamine, and 18 g of water. The reaction solution was stirred at 60° C. for 40 hours and then concentrated. To the concentrate were added 290 g of methanol, 60 g of acetone, and 470 g of hexane. The solution separated into two layers, whereupon the lower layer was taken out and concentrated in vacuum. The concentrate was combined with 550 g of ethyl acetate, successively washed with 15% aqueous acetic acid, 25% aqueous pyridine, and then water, and concentrated in vacuum. The concentrate was combined with 300 g of acetone and added dropwise to 2 L of water whereupon a polymer crystallized out. The crystallized polymer was collected by filtration and dried in vacuum at 40° C. for 20 hours. The polymer, designated Polymer 12, was obtained in white powder solid form. The amount was 106 g, with a yield of 65%.

(Polymer 12)

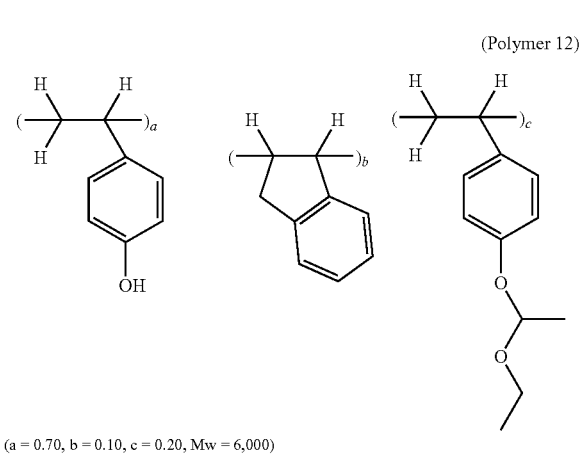

(a = 0.70, b = 0.10, c = 0.20, Mw = 6,000)

Synthesis Examples 2-13 to 2-22

Synthesis of Polymers 13 to 22

Polymers 13 to 22 were prepared by the same procedure as Synthesis Example 2-12 except that the type and proportion of monomers were changed.

Synthesis Example 2-23

Synthesis of Polymer 23

To 50 g of Polymer 21 synthesized by the above procedure, that is, a copolymer of hydroxystyrene/indene in a ratio of 0.90 mole/0.10 mole, were added 500 g of tetrahydrofuran and 26 g of triethylamine. To this mixture, 7.8 g of 1-chloro-1-methoxy-2-methylpropane was added dropwise, followed by stirring at room temperature for 2 hours. At the end of stirring, 150 g of water was added, whereupon the organic layer was taken out and concentrated in vacuum. The concentrate was combined with 270 g of ethyl acetate, successively washed with 15% aqueous acetic acid, 25% aqueous pyridine, and then water, and concentrated in vacuum. The concentrate was combined with 150 g of acetone and added dropwise to 2 L of water whereupon a polymer crystallized out. The crystallized polymer was collected by filtration and dried in vacuum at 40° C. for 20 hours. The polymer, designated Polymer 23, was obtained in white powder solid form. The amount was 45 g, with a yield of 87%.

(Polymer 23)

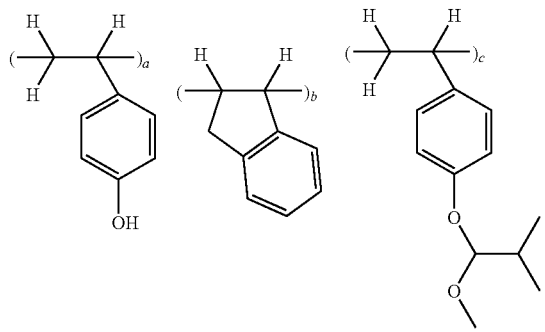

(a = 0.70, b = 0.10, c = 0.20, Mw = 6,800)

Synthesis Examples 2-24 to 2-26

Synthesis of Polymers 24 to 26

Polymers 24 to 26 were prepared by the same procedure as Synthesis Example 2-23 except that the type and proportion of monomers were changed.

With respect to the deprotection and protection on polyhydroxystyrene derivatives in Synthesis Examples 2-12 to 2-26, reference should be made to JP-A 2004-115630 and JP-A 2005-008766.

Synthesis Example 2-27

Synthesis of Polymer 27

In a nitrogen blanket, 7.1 g of 3-hydroxy-1-adamantyl methacrylate, 11.0 g of 3-ethyl-3-exo-tetracyclo-[4.4.0.1$^{2,5}$.1$^{7,10}$]dodecyl methacrylate, 6.7 g of 4,8-dioxatricyclo[4.2.1.0$^{3,7}$]nonan-5-on-2-yl methacrylate, and 0.9 g of dimethyl 2,2'-azobis(isobutyrate) were dissolved in 72.8 g of methyl ethyl ketone to form a solution. In the nitrogen blanket, the solution was added dropwise over 4 hours to 20.7 g of methyl ethyl ketone while stirring at 80° C. After the completion of addition, the solution was stirred at 80° C. for a further 2 hours and then allowed to cool down to room temperature. The polymerization solution was added dropwise to 400 g of hexane. The solids precipitated were filtered, washed twice with a mixture of 45 g methyl ethyl ketone and 195 g hexane, and dried in vacuum at 50° C. for 20 hours. The polymer, designated Polymer 27, was obtained in white powder solid form. The amount was 23.6 g, with a yield of 95%.

(Polymer 27)

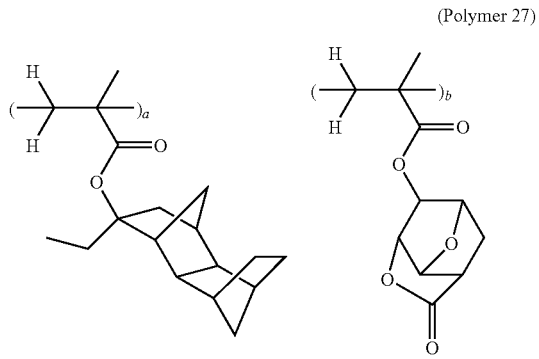

(a = 0.40, b = 0.30, c = 0.30, Mw = 8,000)

Synthesis Examples 2-28 to 2-30

Synthesis of Polymers 28 to 30

Polymers 28 to 30 were prepared by the same procedure as Synthesis Example 2-27 except that the type and proportion of monomers were changed.

The polymers (resins) prepared above are shown in Table 1. The structure of the units in Table 1 is shown in Tables 2 and 3. Note that the ratio of incorporated units in Table 1 is expressed in a molar ratio.

TABLE 1

|  | Resin | Unit 1 (ratio) | Unit 2 (ratio) | Unit 3 (ratio) | Unit 4 (ratio) |
|---|---|---|---|---|---|
| Synthesis Example 2-1 | Polymer 1 | A-2 (0.70) | A-9 (0.10) | A-3 (0.20) | — |
| 2-2 | Polymer 2 | A-2 (0.70) | A-10 (0.10) | A-3 (0.20) | — |
| 2-3 | Polymer 3 | A-2 (0.70) | A-9 (0.10) | A-4 (0.20) | — |
| 2-4 | Polymer 4 | A-2 (0.70) | A-10 (0.10) | A-4 (0.20) | — |
| 2-5 | Polymer 5 | A-2 (0.70) | A-9 (0.10) | A-5 (0.20) | — |
| 2-6 | Polymer 6 | A-2 (0.70) | A-10 (0.10) | A-5 (0.20) | — |
| 2-7 | Polymer 7 | A-2 (0.80) | A-9 (0.10) | A-8 (0.10) | — |
| 2-8 | Polymer 8 | A-2 (0.85) | B-4M (0.15) | — | — |
| 2-9 | Polymer 9 | A-2 (0.80) | A-10 (0.10) | B-4M (0.10) | — |
| 2-10 | Polymer 10 | A-2 (0.90) | A-9 (0.10) | — | — |
| 2-11 | Polymer 11 | A-2 (0.90) | A-10 (0.10) | — | — |
| 2-12 | Polymer 12 | A-1 (0.70) | A-9 (0.10) | A-3 (0.20) | — |
| 2-13 | Polymer 13 | A-1 (0.70) | A-10 (0.10) | A-3 (0.20) | — |
| 2-14 | Polymer 14 | A-1 (0.70) | A-9 (0.10) | A-4 (0.20) | — |
| 2-15 | Polymer 15 | A-1 (0.70) | A-10 (0.10) | A-4 (0.20) | — |
| 2-16 | Polymer 16 | A-1 (0.70) | A-9 (0.10) | A-5 (0.20) | — |
| 2-17 | Polymer 17 | A-1 (0.70) | A-10 (0.10) | A-5 (0.20) | — |
| 2-18 | Polymer 18 | A-1 (0.80) | A-9 (0.10) | A-8 (0.10) | — |
| 2-19 | Polymer 19 | A-1 (0.85) | B-4M (0.15) | — | — |
| 2-20 | Polymer 20 | A-1 (0.80) | A-10 (0.10) | B-4M (0.10) | — |
| 2-21 | Polymer 21 | A-1 (0.90) | A-9 (0.10) | — | — |
| 2-22 | Polymer 22 | A-1 (0.90) | A-10 (0.10) | — | — |
| 2-23 | Polymer 23 | A-1 (0.70) | A-9 (0.10) | A-6 (0.20) | — |
| 2-24 | Polymer 24 | A-1 (0.70) | A-10 (0.10) | A-6 (0.20) | — |
| 2-25 | Polymer 25 | A-1 (0.70) | A-9 (0.10) | A-7 (0.20) | — |
| 2-26 | Polymer 26 | A-1 (0.70) | A-10 (0.10) | A-7 (0.20) | — |
| 2-27 | Polymer 27 | B-1M (0.40) | B-5M (0.30) | B-6M (0.30) | — |
| 2-28 | Polymer 28 | B-2M (0.20) | B-5M (0.15) | B-6M (0.40) | B-3M (0.25) |
| 2-29 | Polymer 29 | B-3M (0.30) | B-5M (0.25) | B-6M (0.45) | — |
| 2-30 | Polymer 30 | B-4M (0.55) | B-5M (0.20) | B-6M (0.25) | — |

TABLE 2

A-1     A-2

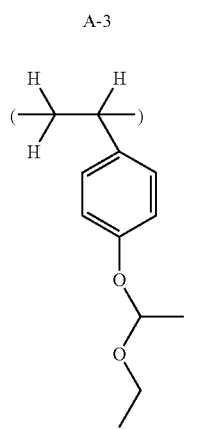

A-3     A-4

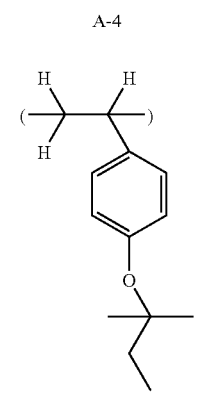

A-5     A-6

TABLE 2-continued

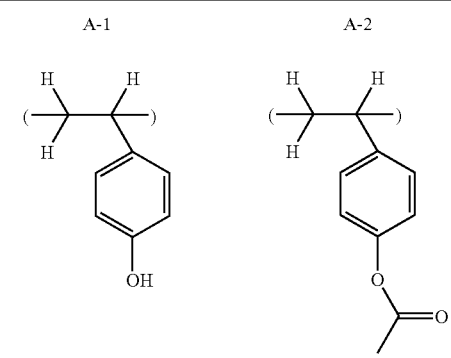

A-7     A-8

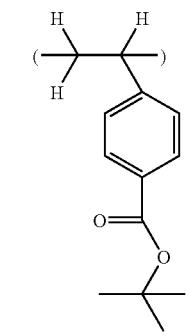 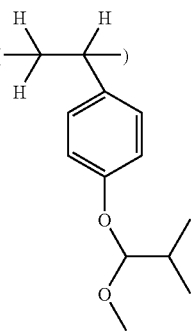

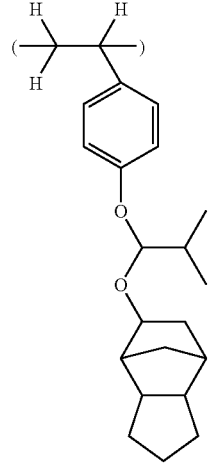

TABLE 2-continued

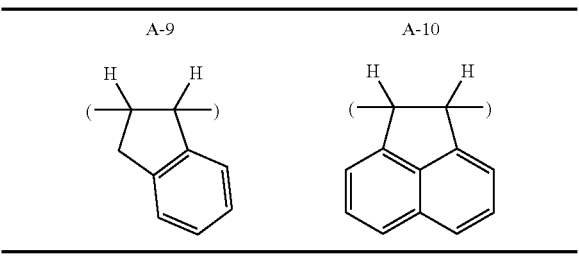

TABLE 3

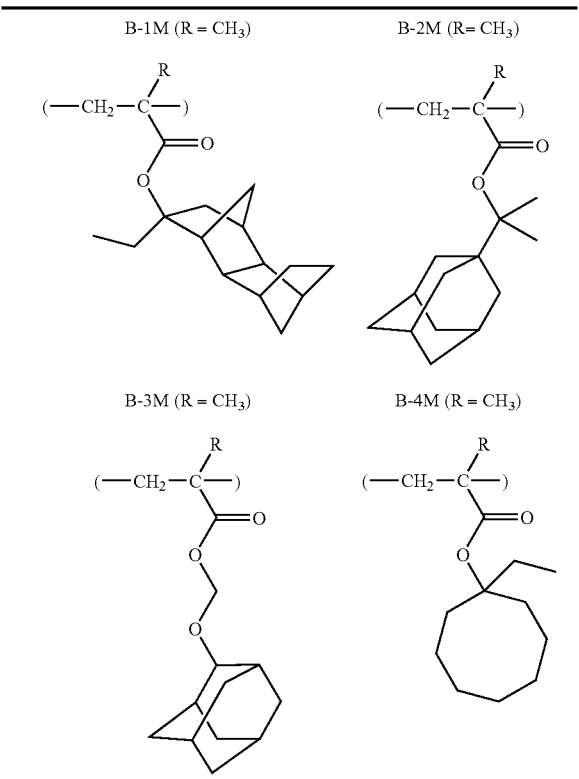

TABLE 3-continued

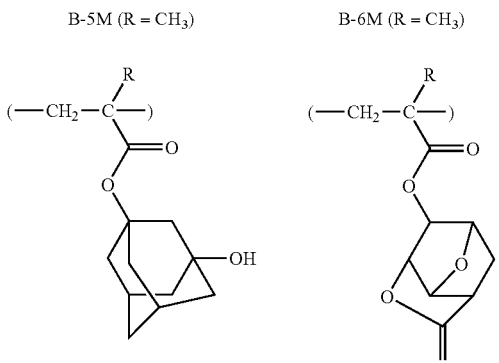

Preparation of Resist Compositions

Examples 1-1 to 1-21 & Comparative Examples 1-1 to 1-5

Resist compositions were prepared by using the above resin as the base resin, and dissolving the polymer, an acid generator, and an additive (Base or crosslinker) in a solvent (mixture of PGMEA and EL or CyHO) in accordance with the recipe shown in Table 4. These compositions were each filtered through a Teflon® filter having a pore diameter 0.2 μm, thereby giving inventive resist solutions (R-01 to 21) and comparative resist solutions (R-22 to 26). Note that the solvent contained 0.01 wt % of surfactant (Surfactant 1, Omnova Solutions, Inc.).

TABLE 4

|  |  | Resist | Resin (pbw) | PAG (pbw) | Additive (pbw) | Solvent 1 (pbw) | Solvent 2 (pbw) |
|---|---|---|---|---|---|---|---|
| Example | 1-1 | R-01 | Polymer 12 (80) | PAG-1 (8.0) | Base-1 (1.10) | PGMEA (540) | EL (1,280) |
|  | 1-2 | R-02 | Polymer 12 (80) | PAG-2 (11.2) | Base-1 (1.10) | PGMEA (540) | EL (1,280) |
|  | 1-3 | R-03 | Polymer 12 (80) | PAG-3 (7.2) | Base-1 (1.10) | PGMEA (540) | EL (1,280) |
|  | 1-4 | R-04 | Polymer 12 (80) | PAG-4 (8.2) | Base-1 (1.10) | PGMEA (540) | EL (1,280) |
|  | 1-5 | R-05 | Polymer 13 (80) | PAG-1 (8.0) | Base-1 (1.10) | PGMEA (540) | EL (1,280) |
|  | 1-6 | R-06 | Polymer 14 (80) | PAG-1 (8.0) | Base-1 (1.10) | PGMEA (540) | EL (1,280) |
|  | 1-7 | R-07 | Polymer 15 (80) | PAG-1 (8.0) | Base-1 (1.10) | PGMEA (540) | EL (1,280) |
|  | 1-8 | R-08 | Polymer 16 (80) | PAG-1 (8.0) | Base-1 (1.10) | PGMEA (540) | EL (1,280) |
|  | 1-9 | R-09 | Polymer 17 (80) | PAG-1 (8.0) | Base-1 (1.10) | PGMEA (540) | EL (1,280) |
|  | 1-10 | R-10 | Polymer 18 (80) | PAG-1 (8.0) | Base-1 (1.10) TMGU (10) | PGMEA (540) | EL (1,280) |
|  | 1-11 | R-11 | Polymer 19 (80) | PAG-1 (8.0) | Base-1 (1.10) | PGMEA (540) | EL (1,280) |
|  | 1-12 | R-12 | Polymer 20 (80) | PAG-1 (8.0) | Base-1 (1.10) | PGMEA (540) | EL (1,280) |
|  | 1-13 | R-13 | Polymer 23 (80) | PAG-1 (8.0) | Base-1 (1.10) | PGMEA (540) | EL (1,280) |
|  | 1-14 | R-14 | Polymer 24 (80) | PAG-1 (8.0) | Base-1 (1.10) | PGMEA (540) | EL (1,280) |
|  | 1-15 | R-15 | Polymer 25 (80) | PAG-1 (8.0) | Base-1 (1.10) | PGMEA (540) | EL (1,280) |
|  | 1-16 | R-16 | Polymer 26 (80) | PAG-1 (8.0) | Base-1 (1.10) | PGMEA (540) | EL (1,280) |
|  | 1-17 | R-17 | Polymer 27 (80) | PAG-1 (8.0) | Base-2 (1.23) | PGMEA (896) | CyHO (364) |
|  | 1-18 | R-18 | Polymer 27 (80) | PAG-1 (2.2) PAG-III (6.0) | — | PGMEA (896) | CyHO (364) |
|  | 1-19 | R-19 | Polymer 28 (80) | PAG-1 (8.0) | Base-2 (1.23) | PGMEA (896) | CyHO (364) |

TABLE 4-continued

|  | Resist | Resin (pbw) | PAG (pbw) | Additive (pbw) | Solvent 1 (pbw) | Solvent 2 (pbw) |
|---|---|---|---|---|---|---|
|  | 1-20 | R-20 | Polymer 29 (80) | PAG-1 (8.0) | Base-2 (1.23) | PGMEA (896) | CyHO (364) |
|  | 1-21 | R-21 | Polymer 30 (80) | PAG-1 (8.0) | Base-2 (1.23) | PGMEA (896) | CyHO (364) |
| Comparative | 1-1 | R-22 | Polymer 20 (80) | PAG-I (7.2) | Base-1 (1.10) | PGMEA (540) | EL (1,280) |
| Example | 1-2 | R-23 | Polymer 20 (80) | PAG-II (7.9) | Base-1 (1.10) | PGMEA (540) | EL (1,280) |
|  | 1-3 | R-24 | Polymer 25 (80) | PAG-I (7.2) | Base-1 (1.10) | PGMEA (540) | EL (1,280) |
|  | 1-4 | R-25 | Polymer 25 (80) | PAG-IV (7.9) | Base-1 (1.10) | PGMEA (540) | EL (1,280) |
|  | 1-5 | R-26 | Polymer 27 (80) | PAG-III (6.0) | Base-2 (1.23) | PGMEA (896) | CyHO (364) |

The acid generator, additive (base or crosslinker) and solvent shown in Table 4 have the following meanings.
PAG-1 to PAG-4: the acid generators in Synthesis Examples
PAG-I: triphenylsulfonium camphorsulfonate triphenylsulfonium 2,4,6-triisopropylbenzenesulfonate
PAG-III: triphenylsulfonium 2-(adamantane-1-carbonyloxy)-1,1,3,3,3-pentafluoropropane-1-sulfonate (described in JP-A 2007-145797)
PAG-IV: triphenylsulfonium adamantane-1-sulfonate
Base-1: tri(2-methoxymethoxyethyl)amine
Base-2: 2-morpholinoethyl laurate
TMGU: 1,3,4,6-tetramethoxymethylglycoluril
PGMEA: propylene glycol monomethyl ether acetate
CyHO: cyclohexanone
EL: ethyl lactate
Surfactant 1: 3-methyl-3-(2,2,2-trifluoroethoxymethyl)oxetane/tetrahydrofuran/2,2-dimethyl-1,3-propane diol copolymer (Omnova Solutions, Inc.)
Evaluation of Resolution, Depth of Focus and Pattern Profile on KrF Lithography Examples 2-1 to 2-15 & Comparative Examples 2-1 to 2-4

Each of inventive resist compositions (R-01 to 09, R-11 to 16) and comparative resist compositions (R-22 to 25) was spin coated on a 8-inch silicon wafer having silicon oxide (0.02 µm) deposited thereon and baked on a hot plate at 110° C. for 90 seconds to form a resist film of 0.33 µm thick. The coating and baking steps as well as the subsequent developing step were carried out on a coater/developer system Clean Track Act-8 (Tokyo Electron Ltd.).

The coated silicon wafer was exposed by means of an excimer laser scanner NSR-S203B (Nikon Corp., NA 0.68, normal illumination), post-exposure baked (PEB) at 110° C. for 90 seconds, and developed with a 2.38 wt % tetramethylammonium hydroxide aqueous solution. In this way, positive patterns were formed (Examples 2-1 to 2-15 & Comparative Examples 2-1 to 2-4).

The optimum exposure (Eop) was defined as the exposure dose (mJ/cm$^2$) which provided a 1:1 resolution at the top and bottom of a 0.18-µm line-and-space pattern. The resolution of the resist was defined as the minimum line width (µm) of a line-and-space pattern that was ascertained separate at the optimum exposure. The shape in cross section of the resolved resist pattern was examined under a scanning electron microscope (SEM). The depth of focus (DOF) was determined by offsetting the focal point and judging the resist to be satisfactory when the resist pattern shape was kept rectangular and the resist pattern film thickness was kept above 80% of that at accurate focusing. The results are shown in Table 5.

TABLE 5

|  |  | Resist composition | Eop (mJ/cm$^2$) | Resolution (µm) | DOF at 0.18 µm (µm) | Pattern profile |
|---|---|---|---|---|---|---|
| Example | 2-1 | R-01 | 35 | 0.17 | 0.6 | rectangular |
|  | 2-2 | R-02 | 40 | 0.18 | 0.6 | rectangular |
|  | 2-3 | R-03 | 30 | 0.16 | 0.6 | rectangular |
|  | 2-4 | R-04 | 36 | 0.17 | 0.7 | rectangular |
|  | 2-5 | R-05 | 36 | 0.17 | 0.7 | rectangular |
|  | 2-6 | R-06 | 36 | 0.16 | 0.6 | rectangular |
|  | 2-7 | R-07 | 37 | 0.18 | 0.7 | rectangular |
|  | 2-8 | R-08 | 33 | 0.17 | 0.7 | rectangular |
|  | 2-9 | R-09 | 35 | 0.18 | 0.6 | rectangular |
|  | 2-10 | R-11 | 36 | 0.18 | 0.6 | rectangular |
|  | 2-11 | R-12 | 35 | 0.16 | 0.8 | rectangular |
|  | 2-12 | R-13 | 38 | 0.17 | 0.7 | rectangular |
|  | 2-13 | R-14 | 32 | 0.16 | 0.8 | rectangular |
|  | 2-14 | R-15 | 35 | 0.17 | 0.7 | rectangular |
|  | 2-15 | R-16 | 33 | 0.16 | 0.8 | rectangular |
| Comparative Example | 2-1 | R-22 | 31 | 0.18 | 0.4 | Somewhat rounded top |
|  | 2-2 | R-23 | 30 | 0.18 | 0.5 | Somewhat rounded top |
|  | 2-3 | R-24 | 34 | 0.18 | 0.4 | Somewhat rounded top |
|  | 2-4 | R-25 | 32 | 0.18 | 0.5 | Somewhat rounded top |

The data of Examples in Table 5 demonstrate that the inventive resist compositions exhibit better resolution performance, depth of focus, and pattern profile when processed by KrF excimer laser lithography.

Evaluation of Resolution on EB Lithography

Examples 3-1 to 3-15 & Comparative Examples 3-1 to 3-4

A silicon wafer having chromium deposited on its surface was used as a photomask blank model. Each of the inventive resist compositions (R-01 to 09, R-11 to 16) or comparative resist compositions (R-22 to 25) was spin coated on the silicon wafer and baked on a hot plate at 110° C. for 4 minutes to form a resist film of 0.15 μm thick. Using an EB lithography system HL-800D (Hitachi Hitechnologies, Ltd.) at an accelerating voltage of 50 keV, exposure was performed on the resist film. The resist film was post-exposure baked (PEB) at 110° C. for 4 minutes and developed with a 2.38 wt % TMAH aqueous solution, obtaining a positive pattern.

The resist pattern was evaluated as follows. The optimum exposure (sensitivity, Eop) was defined as the exposure dose ($\mu C/cm^2$) which provided a 1:1 resolution at the top and bottom of a 0.20-μm line-and-space pattern. The resolution of the resist was defined as the minimum line width of a line-and-space pattern that was ascertained separate at the optimum exposure. The profile of the resolved resist pattern was evaluated by observing a cross section of the resist under SEM. The post-exposure delay (PED) in vacuum was evaluated by exposing the coated wafer on an EB lithography system, holding it in the vacuum system for 24 hours, thereafter effecting PEB and development. The size of lines of a 0.20-μm line-and-space pattern at Eop was measured and compared with that obtained from baking immediately after exposure, with a difference (nm) being reported in Table 6. The pattern profile on the Cr-deposited silicon wafer was evaluated, with the results being also shown in Table 6.

It is evident from Table 6 that when processed by EB lithography, the resist compositions of the invention are improved in resolution even on Cr film and minimized in line width variation and profile degradation even on prolonged PED. Thus the resist compositions of the invention are advantageously applicable to mask blanks having a chromium compound film deposited thereon.

Evaluation of Resolution, Exposure Latitude and Line Width Roughness on ArF Lithography Examples 4-1 to 4-5 & Comparative Example 4-1

On a silicon substrate, an antireflective coating solution (ARC-29A, Nissan Chemical Co., Ltd.) was coated and baked at 200° C. for 60 seconds to form an ARC of 78 nm thick. Each of inventive resist compositions (R-17 to 21) and comparative resist composition (R-26) was spin coated on the ARC-coated silicon substrate and baked on a hot plate at 100° C. for 60 seconds, forming a resist film of 100 nm thick. The wafer was exposed by means of an ArF excimer laser scanner NSR-S307E (Nikon Corp., NA 0.85, 4/5 annular illumination, 6% halftone phase shift mask), post-exposure baked (PEB) at 100° C. for 60 seconds, and developed with a 2.38 wt % tetramethylammonium hydroxide aqueous solution for 60 seconds.

The optimum exposure (Eop) was defined as the exposure dose ($mJ/cm^2$) which provided a 1:1 resolution at the top and bottom of a 80-nm grouped line-and-space pattern. The maximum resolution of the resist was defined as the minimum line width (nm) of a line-and-space pattern that was ascertained separated at the optimum exposure. For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude. The line width roughness (LWR) of a 80-nm

TABLE 6

| | | Resist composition | Eop ($\mu C/cm^2$) | Resolution (nm) | PED in vacuum (nm) | Pattern profile |
|---|---|---|---|---|---|---|
| Example | 3-1 | R-01 | 9.1 | 80 | 2.1 | rectangular |
| | 3-2 | R-02 | 10.5 | 80 | 2.4 | rectangular |
| | 3-3 | R-03 | 7.8 | 80 | 3.0 | rectangular |
| | 3-4 | R-04 | 8.7 | 75 | 2.1 | rectangular |
| | 3-5 | R-05 | 9.2 | 80 | 3.4 | rectangular |
| | 3-6 | R-06 | 9.3 | 75 | 3.3 | rectangular |
| | 3-7 | R-07 | 9.6 | 75 | 2.9 | rectangular |
| | 3-8 | R-08 | 8.8 | 80 | 3.1 | rectangular |
| | 3-9 | R-09 | 9.0 | 80 | 2.9 | rectangular |
| | 3-10 | R-11 | 9.8 | 80 | 3.3 | rectangular |
| | 3-11 | R-12 | 8.3 | 70 | 4.1 | rectangular |
| | 3-12 | R-13 | 8.9 | 70 | 3.9 | rectangular |
| | 3-13 | R-14 | 8.2 | 70 | 4.2 | rectangular |
| | 3-14 | R-15 | 8.7 | 75 | 3.9 | rectangular |
| | 3-15 | R-16 | 8.4 | 65 | 4.1 | rectangular |
| Comparative Example | 3-1 | R-22 | 8.7 | 110 | 7.2 | Somewhat rounded top |
| | 3-2 | R-23 | 10.2 | 95 | 7.0 | Somewhat rounded top |
| | 3-3 | R-24 | 9.0 | 100 | 7.8 | Somewhat rounded top |
| | 3-4 | R-25 | 10.7 | 95 | 6.8 | Somewhat rounded top | line-and-space pattern was measured using measurement SEM (S-9380 by Hitachi Hitechnologies, Ltd.). The results are shown in Table 7.

TABLE 7

| | | Resist composition | Eop (mJ/cm$^2$) | Maximum resolution (nm) | Exposure latitude (%) | LWR (nm) |
|---|---|---|---|---|---|---|
| Example | 4-1 | R-17 | 39 | 80 | 15.0 | 5.8 |
| | 4-2 | R-18 | 36 | 75 | 13.9 | 6.2 |
| | 4-3 | R-19 | 42 | 80 | 14.9 | 5.8 |
| | 4-4 | R-20 | 41 | 75 | 14.7 | 5.9 |
| | 4-5 | R-21 | 40 | 80 | 14.2 | 6.0 |
| Comparative Example | 4-1 | R-26 | 30 | 80 | 11.7 | 7.5 |

The data of Examples in Table 7 demonstrate that the inventive resist compositions exhibit good resolution performance, good exposure latitude and low LWR values when processed by ArF excimer laser lithography.

Japanese Patent Application No. 2008-309566 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (2):

$$\text{(2)}$$

wherein A is a monovalent hydrocarbon group having an aromatic ring or alicyclic hydrocarbon structure of at least 5 carbon atoms, $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$, and $R^4$ may bond together to form a ring with the sulfur atom, and n is an integer of 1 to 3.

2. An acid generator comprising the sulfonium salt of claim 1.

3. A chemically amplified positive resist composition comprising a base resin having a solubility in an alkali developer which changes under the action of an acid, an acid generator, and an organic solvent, said acid generator being capable of generating a sulfonic acid in response to high-energy radiation or heat, said sulfonic acid having the general formula (2a):

$$\text{(2a)}$$

wherein A is a monovalent hydrocarbon group having an aromatic ring or alicyclic hydrocarbon structure of at least 5 carbon atoms, and n is an integer of 1 to 3.

4. The chemically amplified resist composition of claim 3, which is subject to patternwise exposure to high-energy radiation selected from KrF laser radiation, ArF laser radiation, EUV and electron beam.

5. A photomask blank comprising a chromium compound film and the chemically amplified resist composition of claim 3 applied thereon.

6. A pattern forming process comprising the steps of heat treating the photomask blank of claim 5, subjecting the photomask blank to patternwise exposure to high-energy radiation through a photomask or patternwise exposure to high-energy beam optionally heat treating, and developing the exposed photomask blank with a developer.

7. The chemically amplified positive resist composition of claim 3, wherein said acid generator is a sulfonium salt having the general formula (2):

$$\text{(2)}$$

wherein A is a monovalent hydrocarbon group having an aromatic ring or alicyclic hydrocarbon structure of at least 5 carbon atoms, $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$, and $R^4$ may bond together to form a ring with the sulfur atom, and n is an integer of 1 to 3.

8. A chemically amplified negative resist composition comprising a base resin which is soluble in alkaline developer, an acid generator, a crosslinker for inducing crosslinkage under the action of an acid, and an organic solvent, said acid generator being capable of generating a sulfonic acid in response to high-energy radiation or heat, said sulfonic acid having the general formula (2a):

$$\text{(2a)}$$

wherein A is a monovalent hydrocarbon group having an aromatic ring or alicyclic hydrocarbon structure of at least 5 carbon atoms, and n is an integer of 1 to 3.

9. The chemically amplified negative resist composition of claim 8, wherein said acid generator is a sulfonium salt having the general formula (2):

$$\text{(2)}$$

wherein A is a monovalent hydrocarbon group having an aromatic ring or alicyclic hydrocarbon structure of at least 5 carbon atoms, $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$, and $R^4$ may bond together to form a ring with the sulfur atom, and n is an integer of 1 to 3.

10. The chemically amplified resist composition of claim 7, which is subject to patternwise exposure to high-energy radiation selected from KrF laser radiation, ArF laser radiation, EUV and electron beam.

11. A photomask blank comprising a chromium compound film and the chemically amplified resist composition of claim 7 applied thereon.

12. A pattern forming process comprising the steps of heat treating the photomask blank of claim 11, subjecting the photomask blank to patternwise exposure to high-energy radiation through a photomask or patternwise exposure to high-energy beam, optionally heat treating, and developing the exposed photomask blank with a developer.

* * * * *